(12) United States Patent
Cutler

(10) Patent No.: US 11,414,673 B2
(45) Date of Patent: Aug. 16, 2022

(54) HYPERSENSITIVE ABA RECEPTORS HAVING MODIFIED PP2C-BINDING INTERFACES

(71) Applicant: THE REGENTS OF THE UNIVERSITY OF CALIFORNIA, Oakland, CA (US)

(72) Inventor: Sean R. Cutler, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 105 days.

(21) Appl. No.: 16/484,403

(22) PCT Filed: Feb. 9, 2018

(86) PCT No.: PCT/US2018/017642
§ 371 (c)(1),
(2) Date: Aug. 7, 2019

(87) PCT Pub. No.: WO2018/148558
PCT Pub. Date: Aug. 16, 2018

(65) Prior Publication Data
US 2019/0359999 A1    Nov. 28, 2019

Related U.S. Application Data

(60) Provisional application No. 62/457,301, filed on Feb. 10, 2017.

(51) Int. Cl.
*C12N 15/82* (2006.01)
*C07K 14/415* (2006.01)
*C12N 9/16* (2006.01)

(52) U.S. Cl.
CPC ........ *C12N 15/8293* (2013.01); *C07K 14/415* (2013.01); *C12N 9/16* (2013.01); *C12N 2310/20* (2017.05); *C12Y 301/03016* (2013.01)

(58) Field of Classification Search
None
See application file for complete search history.

(56) References Cited

U.S. PATENT DOCUMENTS

| | | | | |
|---|---|---|---|---|
| 2014/0259226 | A1* | 9/2014 | Cutler | C12N 15/8273 800/298 |
| 2014/0325701 | A1* | 10/2014 | Cutler | A01N 41/06 800/278 |
| 2015/0074844 | A1* | 3/2015 | Zhu | C07K 14/415 800/270 |

OTHER PUBLICATIONS

Dorosh et al. (FEBS Open Biol., 4:496-509).*
Mosquna et al. (PNAS; 108:20838-20843; Published 2011).*
Smith et al. (Nature Biotechnology, 15:1222-1223, 1997).*
Bork et al. (TIG, 12:425-427, 1996).*
Doerks et al., (TIG, 14:248-250, 1998).*

\* cited by examiner

*Primary Examiner* — Vinod Kumar
(74) *Attorney, Agent, or Firm* — Kilpatrick Townsend & Stockton LLP

(57) ABSTRACT

Hypersensitive PYR/PYL receptor polypeptides comprising an amino acid substitution in a type 2 protein phosphatase (PP2C) binding interface are provided. Compositions and plants comprising the hypersensitive PYR/PYL receptor polypeptides and methods of producing plants comprising a hypersensitive PYR/PYL receptor polypeptide are also provided.

18 Claims, 4 Drawing Sheets
Specification includes a Sequence Listing.

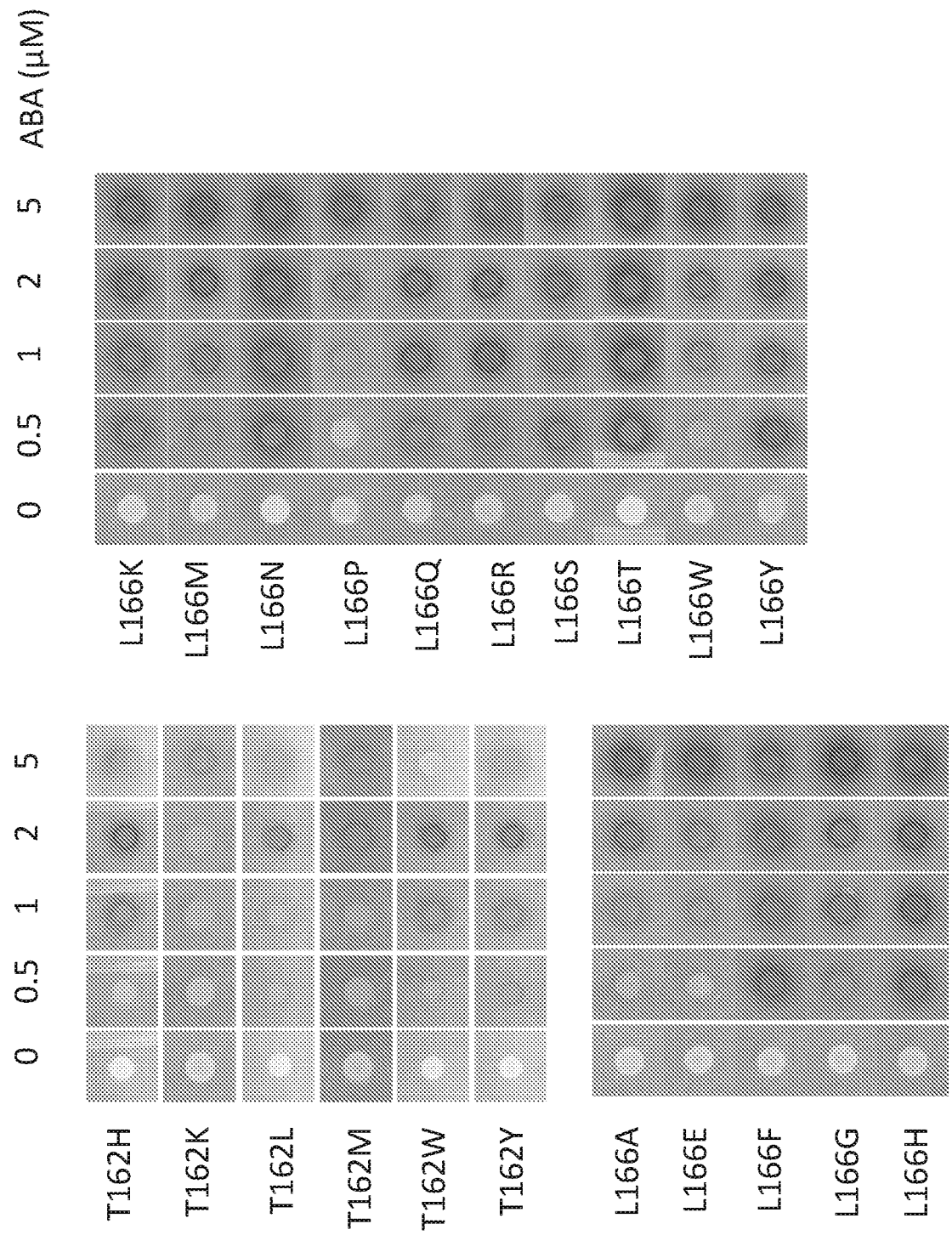

HYPERSENSITIVE ABA RECEPTORS HAVING MODIFIED PP2C-BINDING INTERFACES

This application is a U.S. National Phase application based on International Patent Application No. PCT/US2018/017642, filed Feb. 9, 2018, and claims priority to U.S. Provisional Patent Application No. 62/457,301, filed Feb. 10, 2017, the entire contents of which are hereby incorporated by reference.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 081906_1143781_223110US.txt, created on Mar. 19, 2018, 182,052 bytes, machine format IBM-PC, MS-Windows operating system, is hereby incorporated by reference in its entirety for all purposes.

BACKGROUND OF THE INVENTION

Abscisic acid (ABA) is a plant hormone that regulates signal transduction associated with abiotic stress responses (Cutler et al., *Annu. Rev. Plant Biol*, 2010, 61:651-679). The ABA signaling pathway has been exploited to improve plant stress response and associated yield traits via numerous approaches (Wang et al., *Plant J.*, 2005, 43:413-424). The direct application of ABA to plants improves their water use efficiency (Raedmacher et al., *BCPC Monograph*, 1987, 36:53-66); for this reason, the discovery of ABA agonists (e.g., Park et al., *Science*, 2009, 324:1068-1071) has received increasing attention, as such molecules may be beneficial for improving crop yield. A complementary approach to activating the ABA pathway involves increasing a plant's sensitivity to ABA via genetic methods. For example, conditional antisense of farnesyl transferase beta subunit gene, which increases a plant's ABA sensitivity, improves yield under moderate drought in both canola and *Arabidopsis* (Wang et al., supra).

It has been discovered that ABA elicits many of its cellular responses by binding to a soluble family of receptors called PYR/PYL proteins. PYR/PYL proteins belong to a large family of ligand-binding proteins named the START superfamily (Iyer et al., *Proteins Struct. Funct. Bioinforma.*, 2001, 43:134-144; Ponting et al., *Trends Biochem. Sci.*, 1999, 24:130-132). These proteins contain a conserved three-dimensional architecture consisting of seven anti-parallel beta sheets, which surround a central alpha helix to form a "helix-grip" motif; together, these structural elements form a ligand-binding pocket for binding ABA or other agonists.

Structural and functional studies have uncovered a series of conformational changes and critical contacts between PYR/PYL receptors and type II C protein phosphatases (PP2Cs) that are necessary for ABA-mediated PP2C inhibition by receptors. For example, when ABA or another agonist binds within the ligand-binding pockets of PYR/PYL proteins, it stabilizes a conformational change that allows the receptors to bind and inhibit a family of PP2Cs that normally repress ABA signaling (Weiner et al., *Curr. Opin. Plant Biol.*, 2010, 13:495-502). In particular, ABA binding leads to a large rearrangement in a flexible "gate" loop that flanks the ligand-binding pocket. Upon ABA binding, the gate loop adopts a closed conformation that is stabilized by several direct contacts between the loop and ABA. This agonist-bound, closed form of the gate allows PYR/PYL proteins to dock into, and inhibit, the active site of PP2Cs. The resulting inhibition in turn allows activation of downstream kinases in the SnRK2 class, which are responsible for the regulation of the activity of transcription factors, ion channels and other proteins involved in ABA responses (Weiner et al., supra). Thus, the stabilization of a closed gate conformation of the receptors is critical to their activation and PYR/PYL receptors are molecular switches at the apex of a signaling cascade that regulates diverse ABA responses.

In addition to the role that gate closure plays in receptor activation, other structural rearrangements also occur. For example, PYR1, PYL1, and PYL2 are homodimers in solution, but bind to PP2Cs as monomers. The homodimer interface overlaps with the PP2C binding interface and therefore an intact receptor homodimer cannot bind to and inhibit the PP2C. Thus, dimer formation is antagonistic to ABA signaling and receptor dimer-breaking is a necessary step in receptor activation. Additionally, a recognition module containing a central conserved tryptophan "lock" residue located on the PP2C inserts into a small pore formed in the ABA-bound receptors. Mutation of the tryptophan lock residue abolishes receptor-mediated inactivation of PP2C activity, demonstrating a role of the lock residue's insertion into the receptor's pore.

Over-expression of wild type or mutant ABA receptors in transgenic *Arabidopsis thaliana, Solanum lycopersicum* and *Oryza sativa* improves drought tolerance (see, e.g., Kim et al., *J. Exp. Bot.*, 2012, 63:1013-1024; Santiago et al., *Plant J.*, 2009, 60:575-588). ABA receptors with increased sensitivity relative to their wild type counterparts can elicit greater ABA responses when expressed in planta. Consistent with this. Pizzio et al., *Plant Physiol.* 163, 441-455 (2013) described the PYL4 mutation A194T mutant, which requires lower concentrations of ABA to elicit measured ABA responses in comparison to wild type PYL4. When this mutant is over-expressed in transgenic *Arabidopsis*, the plants have increased sensitivity to ABA relative to both wild type controls and PYL4 over-expression controls. Moreover, the 35S::PYL4$^{A194T}$ lines display better drought tolerance and water use than wild type or 35S::PYL4 overexpression lines. The A194T mutation is located in PYL4's carboxyl terminus, which is a part of the receptors that is highly variable in length and composition between receptors.

BRIEF SUMMARY OF THE INVENTION

Mutations in PYR/PYL receptor proteins have been identified that result in the receptor proteins being hypersensitive to ABA. In one aspect, isolated nucleic acids comprising polynucleotides encoding such mutated PYR/PYL receptor polypeptides are provided. In some embodiments, the isolated nucleic acid encodes a mutated PYR/PYL receptor polypeptide comprising one or more amino acid substitutions in a type 2 protein phosphatase (PP2C) binding interface at a position corresponding to K63, I82, I84, D154, M158, T162, L166, or K170 in PYR1 as set forth in SEQ ID NO:1, wherein the mutated PYR/PYL receptor polypeptide inhibits the activity of a PP2C in the presence of abscisic acid (ABA) to a greater extent than a control PYR/PYL receptor polypeptide in the presence of the same concentration of ABA, and wherein the mutated PYR/PYL receptor polypeptide does not inhibit the PP2C in the absence of ABA.

In some embodiments, the mutated PYR/PYL receptor polypeptide comprises one or more amino acid substitutions corresponding to the amino acid substitution K63D/E/Q, I82A/F/K/S, I84A/D/N/R/S/T, D154E/F/G/H/K/M/Q/R/W/Y M158A/D/G/H/N/W, T162H/K/L/M/W/Y, L166A/E/G/H/K/M/N/P/Q/R/S/T/W. or K170A/C/D/E/F/G/H/I/M/N/Q/R/S/T/V/Y in PYR1 as set forth in SEQ ID NO:1.

In some embodiments, the mutated PYR/PYL receptor polypeptide comprises an amino acid substitution corresponding to K63/D/E/Q.

In some embodiments, the mutated PYR/PYL receptor polypeptide comprises an amino acid substitution corresponding to I82A/F/K/S.

In some embodiments, the mutated PYR/PYL receptor polypeptide comprises an amino acid substitution corresponding to I84A/D/N/R/S/T.

In some embodiments, the mutated PYR/PYL receptor polypeptide comprises an amino acid substitution corresponding to D154E/F/G/H/K/M/Q/R/W/Y.

In some embodiments, the mutated PYR/PYL receptor polypeptide comprises an amino acid substitution corresponding to M158A/D/G/H/N/W. In some embodiments, the mutated PYR/PYL receptor polypeptide comprises an amino acid substitution corresponding to M158D/G/H/W.

In some embodiments, the mutated PYR/PYL receptor polypeptide comprises an amino acid substitution corresponding to T162H/K/I/M/W/Y. In some embodiments, the mutated PYR/PYL receptor polypeptide comprises an amino acid substitution corresponding to T162Y.

In some embodiments, the mutated PYR/PYL receptor polypeptide comprises an amino acid substitution corresponding to L166A/E/G/H/K/M/N/P/Q/R/S/T/W/Y. In some embodiments, the mutated PYR/PYL receptor polypeptide comprises an amino acid substitution corresponding to L166G/H/K/N/Q/R/S/T.

In some embodiments, the mutated PYR/PYL receptor polypeptide comprises an amino acid substitution corresponding to K170A/C/D/E/F/G/H/I/M/N/Q/R/S/T/V/Y. In some embodiments, the mutated PYR/PYL receptor polypeptide comprises an amino acid substitution corresponding to K170A/C/D/E/F/G/I/M/S/T/V/Y.

In some embodiments, the mutated PYR/PYL receptor polypeptide is substantially identical to (e.g., at least 50%, 55%, 60%, 65%, 70%, 75%, 80%, 85%, 90%, 91%, 92%, 93%, 94% 95%, 96%, 97%, 98%, or 99% identical to) any of SEQ ID NOs:1-89.

In some embodiments, the PP2C is a Clade A PP2C. In some embodiments, the PP2C is HAB1.

In some embodiments, the polynucleotide encodes a fusion protein, the fusion protein comprising the mutated PYR/PYL receptor polypeptide and a fusion partner protein.

In some embodiments, the fusion partner protein is a transcriptional activation or modulation domain. In some embodiments, the transcriptional activator is VP16 or VP64. In some embodiments, the fusion protein further comprises a nuclear localization signal sequence.

Also provided are cells comprising such isolated nucleic acids. in some embodiments, the cell is a non-plant eukaryotic cell.

Further provided are plants (e.g. a transgenic or non-transgenic plant) comprising a polynucleotide encoding a PYR/PYL receptor polypeptide as described above or elsewhere herein, e.g., comprising an amino acid substitution corresponding to K63, I82, I84, D154, M158, T162, L166, or K170 in PYR1 as set forth in SEQ ID NO:1, wherein the mutated PYR/PYL receptor polypeptide inhibits the activity of a PP2C (e.g., a Clade A PP2C, e.g., HAB1) in the presence of abscisic acid (ABA) to a greater extent than a control PYR/PYL receptor polypeptide in the presence of the same concentration of ABA, and the mutated PYR/PYL receptor polypeptide does not inhibit the activity of the PP2C in the absence of ABA. In some embodiments, the polynucleotide is operably linked to a heterologous promoter. In some embodiments, the polynucleotide is operably linked to a native (non-heterologous) promoter. In some embodiments, the mutated PYR/PYL receptor polypeptide comprises one or more amino acid substitutions corresponding to the amino acid substitution K63D/E/Q, I82A/F/K/S, I84A/D/N/R/S/T, D154E/F/G/H/K/M/Q/R/W/Y M158A/D/G/H/N/W. T162H/K/L/M/W/Y, L166A/E/G/H/K/M/N/P/Q/R/S/T/W, or K170A/C/D/E/F/G/H/I/M/N/Q/R/S/T/V/Y in PYR1 as set forth in SEQ ID NO:1. In some embodiments, the mutated PYR/PYL receptor polypeptide comprises an amino acid substitution corresponding to K63/D/E/Q. In some embodiments, the mutated PYR/PYL receptor polypeptide comprises an amino acid substitution corresponding to I82A/F/K/S. In some embodiments, the mutated PYR/PYL receptor polypeptide comprises an amino acid substitution corresponding to I84A/D/N/R/S/T. In some embodiments, the mutated PYR/PYL receptor polypeptide comprises an amino acid substitution corresponding to D154E/F/G/H/K/M/Q/R/W/Y. In some embodiments, the mutated PYR/PYL receptor polypeptide comprises an amino acid substitution corresponding to M158A/D/G/H/N/W. In some embodiments, the mutated PYR/PYL receptor polypeptide comprises an amino acid substitution corresponding to M158D/G/H/W. In some embodiments, the mutated PYR/PYL receptor polypeptide comprises an amino acid substitution corresponding to T162H/K/L/M/W/Y. In some embodiments, the mutated PYR/PYL receptor polypeptide comprises an amino acid substitution corresponding to T162Y. In some embodiments, the mutated PYR/PYL receptor polypeptide comprises an amino acid substitution corresponding to L166A/E/G/H/K/M/N/P/Q/R/S/T/W/Y. In some embodiments, the mutated PYR/PYL receptor polypeptide comprises an amino acid substitution corresponding to L166G/H/K/N/Q/R/S/T. In some embodiments, the mutated PYR/PYL receptor polypeptide comprises an amino acid substitution corresponding to K170A/C/D/E/F/G/H/I/M/N/Q/R/S/T/V/Y. In some embodiments, the mutated PYR/PYL receptor polypeptide comprises an amino acid substitution corresponding to K170A/C/D/E/F/G/I/M/S/T/V/Y. In some embodiments, the mutated PYR/PYL receptor polypeptide is substantially identical to (e.g., at least 50%, 55%, 60%, 65%, 70%, 75%, 80%, 85%, 90%, 91%, 92%, 93%, 94% 95%, 96%, 97%, 98%, or 99% identical to) any of SEQ ID NOs:1-89.

Also provided herein are plants (e.g., including but not limited to a maize plant) comprising an in situ mutated PYR/PYL receptor polypeptide comprising an amino acid substitution corresponding to corresponding to K63, I82, I84, D154, M158, T162, L166, or K170 in PYR1 as set forth in SEQ ID NO:1, wherein the mutated PYR/PYL receptor polypeptide inhibits the activity of a PP2C (e.g., a Clade A PP2C, e.g., HAB1) in the presence of abscisic acid (ABA) to a greater extent than a control PYR/PYL receptor polypeptide in the presence of the same concentration of ABA, and the mutated PYR/PYL receptor polypeptide does not inhibit the activity of the PP2C in the absence of ABA. In some embodiments, the mutated PYR/PYL receptor polypeptide comprises one or more amino acid substitutions corresponding to the amino acid substitution K63D/E/Q, I82A/F/K/S, I84A/D/N/R/S/T, D54E/F/G/H/K/M/Q/R/W/Y M158A/D/G/H/N/W, T162H/K/L/M/W/Y, L166A/E/G/H/

K/M/N/P/Q/R/S/T/W, or K170A/C/D/E/F/G/H/I/M/N/Q/R/S/T/V/Y in PYR1 as set forth in SEQ ID NO:1. In some embodiments, the mutated PYR/PYL receptor polypeptide comprises an amino acid substitution corresponding to K63/D/E/Q. In some embodiments, the mutated PYR/PYL receptor polypeptide comprises an amino acid substitution corresponding to I82A/F/K/S. In some embodiments, the mutated PYR/PYL receptor polypeptide comprises an amino acid substitution corresponding to I84A/D/N/R/S/T. In some embodiments, the mutated PYR/PYL receptor polypeptide comprises an amino acid substitution corresponding to D154E/F/G/H/K/M/Q/R/W/Y. In some embodiments, the mutated PYR/PYL receptor polypeptide comprises an amino acid substitution corresponding to M158A/D/G/H/N/W. In some embodiments, the mutated PYR/PYL receptor polypeptide comprises an amino acid substitution corresponding to M158D/G/H/W. In some embodiments, the mutated PYR/PYL receptor polypeptide comprises an amino acid substitution corresponding to T162H/K/L/M/W/Y. In some embodiments, the mutated PYR/PYL receptor polypeptide comprises an amino acid substitution corresponding to T162Y. In some embodiments, the mutated PYR/PYL receptor polypeptide comprises an amino acid substitution corresponding to L166A/E/G/H/K/M/N/P/Q/R/S/T/W/Y. In some embodiments, the mutated PYR/PYL receptor polypeptide comprises an amino acid substitution corresponding to L166G/H/K/N/Q/R/S/T. In some embodiments, the mutated PYR/PYL receptor polypeptide comprises an amino acid substitution corresponding to K170A/C/D/E/F/G/H/I/M/N/Q/R/S/T/V/Y. In some embodiments, the mutated PYR/PYL receptor polypeptide comprises an amino acid substitution corresponding to K170A/C/D/E/F/G/I/M/S/T/V/Y. In some embodiments, the mutated PYR/PYL receptor polypeptide is substantially identical to (e.g., at least 50%, 55%, 60%, 65%, 70%, 75%, 80%, 85%, 90%, 91%, 92%, 93%, 94% 95%, 96%, 97%, 98%, or 99% identical to) any of SEQ ID NOs:1-89.

Also provided herein are expression cassettes comprising a promoter operably linked to the polynucleotide encoding a PYR/PYL receptor polypeptide as described above or elsewhere herein, e.g., comprising an amino acid substitution corresponding to K63, I82, I84, D154, M158, T162, L166, or K170 in PYR1 as set forth in SEQ ID NO:1, wherein the mutated PYR/PYL receptor polypeptide inhibits the activity of a PP2C (e.g., a Clade A PP2C, e.g., HAB1) in the presence of abscisic acid (ABA) to a greater extent than a control PYR/PYL receptor polypeptide in the presence of the same concentration of ABA, and the mutated PYR/PYL receptor polypeptide does not inhibit the activity of the PP2C in the absence of ABA. In some embodiments, the promoter is heterologous to the polynucleotide.

In some embodiments, the promoter is inducible. In some embodiments, the promoter is a stress-inducible promoter.

Also provided is an expression vector comprising the expression cassette as described above or elsewhere herein.

Further provided are plants comprising an expression cassette as described above or elsewhere herein, wherein the plant has increased sensitivity to abscisic acid compared to a control plant lacking the expression cassette. Also provided is a plant cell from the plant.

Also provided is a seed, flower, leaf, fruit, processed food, or food ingredient from a plant comprising a hypersensitive PYR/PYL receptor polypeptide as described herein.

Further provided herein are methods of producing a plant having increased sensitivity to ABA. In some embodiments, the method comprises: introducing an expression cassette comprising a polynucleotide encoding a hypersensitive PYR/PYL receptor polypeptide as described herein into a plurality of plants; and selecting a plant that expresses the polynucleotide from the plurality of plants.

In some embodiments, the method comprises: introducing a mutation into a polynucleotide encoding a hypersensitive PYR/PYL polypeptide as described herein, e.g., wherein the mutation results in a polynucleotide encoding an amino acid substitution corresponding to K63, I82, I84, D154, M158, T162, L166, or K170 in PYR1 as set forth in SEQ ID NO:1. In some embodiments, the mutation results in a polynucleotide encoding an amino acid substitution corresponding to K63D/E/Q, I82A/F/K/S, I84A/D/N/R/S/T, D154E/F/G/H/K/M/Q/R/W/Y M158A/D/G/H/N/W. T162H/K/L/M/W/Y, L166A/E/G/H/K/M/N/P/Q/R/S/T/W, or K170AC/D/E/F/G/H/I/M/N/Q/R/S/T/V/Y in PYR1 as set forth in SEQ ID NO:1. In some embodiments, the introducing occurs in situ in the genome of a plant cell. In some embodiments, the introducing comprises clustered regularly interspaced short palindromic repeats (CRISPR)/Cas genome editing.

BRIEF DESCRIPTION OF THE DRAWINGS

FIGS. 1A-1D. Characterization of hypersensitive PYR/PYL mutants. Single amino acid substitution mutations in PYR1 at PYR/PYL receptor—type 2 protein phosphatase (PP2C) interface residues were constructed. The mutated polypeptides were tested for interactions with the PP2C HAB1 in a yeast two-hybrid assay under different ABA concentrations (0, 0.5, 1, 2, or 5 µM ABA), with darker spots indicating increased interaction. (A) Wild-type PYR1, K63 mutations, I82 mutations, and I84 mutations. (B) D155 mutations and M158 mutations. (C) T162 mutations and L166 mutations. (D) K170 mutations.

DEFINITIONS

Figure 1A:
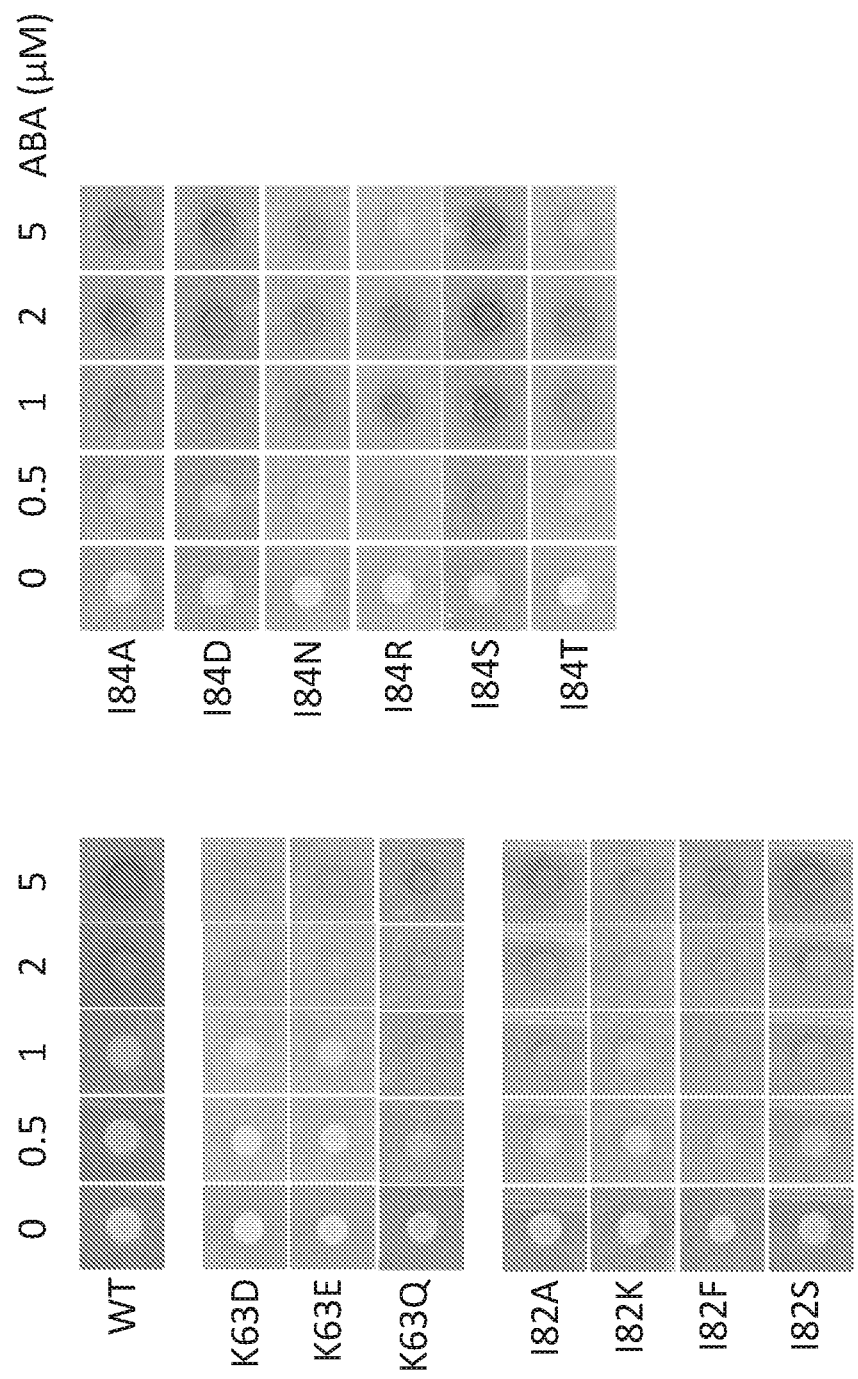

The term "PYR/PYL receptor polypeptide" refers to a protein characterized in part by the presence of one or more or all of a polyketide cyclase domain 2 (PF10604), a polyketide cyclase domain 1 (PF03364), and a Bet V I domain (PF03364), which in wild-type form mediates abscisic acid (ABA) and ABA analog signaling. A wide variety of PYR/PYL receptor polypeptide sequences are known in the art. In some embodiments, a PYR/PYL receptor polypeptide comprises a polypeptide that is substantially identical to PYR1 (SEQ ID NO:1), PYL1 (SEQ ID NO:2), PYL2 (SEQ ID NO:3), PYL3 (SEQ ID NO:4), PYL4 (SEQ ID NO:5), PYL5 (SEQ ID NO:6), PYL6 (SEQ ID NO:7), PYL7 (SEQ ID NO:8), PYL8 (SEQ ID NO:9), PYL9 (SEQ ID NO:10), PYL10 (SEQ ID NO:11), PYL1 (SEQ ID NO:12), PYL12 (SEQ ID NO:13), or PYL13 (SEQ ID NO:14), or to any of SEQ ID NOs:15-89.

The term "type 2 protein phosphatase binding interface" or "PP2C binding interface" refers to an amino acid residue of a PYR/PYL receptor polypeptide which is located within 5 Å of PP2C when ABA, the PYR/PYL receptor polypeptide, and the PP2C are bound in a ternary complex. Proximity of an amino acid residue to PP2C when the PP2C is bound to a PYR/PYL receptor can be determined, e.g., by protein crystallography.

A "wild-type PYR/PYL receptor polypeptide" refers to a naturally occurring PYR/PYL receptor polypeptide that mediates abscisic acid (ABA) and ABA analog signaling.

A "mutated PYR/PYL receptor polypeptide" refers to a PYR/PYL receptor polypeptide that is a variant from a naturally-occurring (i.e., wild-type) PYR/PYL receptor polypeptide. As used herein, a mutated PYR/PYL receptor polypeptide comprises one, two, three, four, or more amino acid substitutions relative to a corresponding wild-type PYR/PYL receptor polypeptide while retaining ABA-responsiveness of the receptor. In this context, a "mutated" polypeptide can be generated by any method for generating non-wild type nucleotide sequences.

In some embodiments, a mutated PYR/PYL receptor polypeptide is hypersensitive, meaning the mutant receptor polypeptide is activated by ABA (e.g., inhibits the activity of a PP2C in the presence of ABA) more strongly than a corresponding homologous wild-type receptor (or at least compared to an otherwise identical PYR/PYL polypeptide having the wild-type amino acid at the mutated position described herein) would be activated by the same concentration of ABA, or that the mutant receptor polypeptide is activated by a lower (e.g., half or less of the) concentration of ABA than activates the corresponding homologous wild-type receptor, or both. For example, in some embodiments, a hypersensitive PYR/PYL polypeptide inhibits the activity of PP2C in the presence of a low amount of ABA (e.g., 0.25 µM ABA or 0.5 µM ABA) to a greater extent than a corresponding homologous wild-type PYR/PYL receptor. In some embodiments, a hypersensitive mutant PYR/PYL polypeptide is activated by ABA more strongly than a corresponding homologous wild-type receptor (e.g., inhibits the activity of a PP2C in the presence of ABA to a greater extent than the corresponding homologous wild-type receptor), but does not exhibit detectable activity in the absence of ABA. In some embodiments, a mutant PYR/PYL receptor polypeptide as described herein does not exhibit detectable activity if the mutated PYR/PYL receptor polypeptide does not exhibit detectable binding to a PP2C in the absence of ABA in an enzymatic phosphatase assay. In some embodiments, the enzymatic phosphatase assay comprises incubating the PYR/PYL receptor polypeptide with the PP2C in the presence of a colorimetric detection reagent (e.g., para-nitrophenylphosphate). See. e.g., WO 2011/139798, incorporated by reference herein.

An "amino acid substitution" refers to replacing the naturally occurring amino acid residue in a given position (e.g., the naturally occurring amino acid residue that occurs in a wild-type PYR/PYL receptor polypeptide) with an amino acid residue other than the naturally-occurring residue. For example, the naturally occurring amino acid residue at position 84 of the wild-type PYR1 receptor polypeptide sequence (SEQ ID NO:1) is isoleucine (I84); accordingly, an amino acid substitution at I84 refers to replacing the naturally occurring isoleucine with any amino acid residue other than isoleucine.

An amino acid residue "corresponding to an amino acid residue [X] in [specified sequence," or an amino acid substitution "corresponding to an amino acid substitution [X] in [specified sequence]" refers to an amino acid in a polypeptide of interest that aligns with the equivalent amino acid of a specified sequence. Generally, as described herein, the amino acid corresponding to a position of a specified PYR/PYL receptor polypeptide sequence can be determined using an alignment algorithm such as BLAST. In some embodiments of the present invention, "correspondence" of amino acid positions is determined by aligning to a region of the PYR/PYL receptor polypeptide comprising SEQ ID NO:1, as discussed further herein. When a PYR/PYL receptor polypeptide sequence differs from SEQ ID NO:1 (e.g., by changes in amino acids or addition or deletion of amino acids), it may be that a particular mutation associated with hypersensitive activity of the PYR/PYL receptor will not be in the same position number as it is in SEQ ID NO:1. For example, amino acid position I88 of PYL2 (SEQ ID NO:3) aligns with amino acid position I84 of PYR1 (SEQ ID NO:1), as can be readily illustrated in an alignment of the two sequences. In this example, amino acid position 88 in SEQ ID NO:3 corresponds to position 84 in SEQ ID NO:1.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The phrase "substantial identity" or "substantially identical." used in the context of two nucleic acids or polypeptides, refers to a sequence that has at least 50% sequence identity with a reference sequence. Alternatively, percent identity can be any integer from 50% to 100%. In some embodiments, a sequence is substantially identical to a reference sequence if the sequence has at least 50%, 55%, 60%, 65%, 70%, 75%, 80%, 85%, 90%, 91%, 92%, 93%, 94%, 95%, 96%, 97%, 98%, or 99% sequence identity to the reference sequence as determined using the methods described herein; preferably BLAST using standard parameters, as described below. Embodiments of the present invention provide for nucleic acids encoding polypeptides that are substantially identical to any of SEQ ID NO:1-89.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, Proc. Nat'l. *Acad. Sci.* USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990). *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=-2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci.* USA 89:10915 (1989)).

The BLAST algorithm also performs a statistical analysis of the similarity between two sequences (see. e.g., Karlin & Altschul, Proc. Nat'l. *Acad. Sci.* USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

The term "promoter," as used herein, refers to a polynucleotide sequence capable of driving transcription of a coding sequence in a cell. Thus, promoters used in the polynucleotide constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "plant promoter" is a promoter capable of initiating transcription in plant cells. A "constitutive promoter" is one that is capable of initiating transcription in nearly all tissue types, whereas a "tissue-specific promoter" initiates transcription only in one or a few particular tissue types.

A polynucleotide sequence is "heterologous" to an organism or a second polynucleotide sequence if it originates from a foreign species, or, if from the same species, is modified from its original form. For example, when a promoter is said to be operably linked to a heterologous coding sequence, it means that the coding sequence is derived from one species whereas the promoter sequence is derived another, different species; or, if both are derived from the same species, the coding sequence is not naturally associated with the promoter (e.g., is a genetically engineered coding sequence, e.g., from a different gene in the same species, or an allele from a different ecotype or variety).

An "expression cassette" refers to a nucleic acid construct that, when introduced into a host cell, results in transcription and/or translation of an RNA or polypeptide, respectively. Antisense or sense constructs that are not or cannot be translated are expressly included by this definition. In the case of both expression of transgenes and suppression of endogenous genes (e.g., by antisense, or sense suppression) one of skill will recognize that the inserted polynucleotide sequence need not be identical, but may be only substantially identical to a sequence of the gene from which it was derived. As explained herein, these substantially identical variants are specifically covered by reference to a specific nucleic acid sequence.

The term "host cell" refers to any cell capable of replicating and/or transcribing and/or translating a heterologous polynucleotide. Thus, a "host cell" refers to any prokaryotic cell (including but not limited to *E. coli*) or eukaryotic cell (including but not limited to yeast cells, mammalian cells, avian cells, amphibian cells, plant cells, fish cells, and insect cells), whether located in vitro or in vivo. For example, host cells may be located in a transgenic animal or transgenic plant. prokaryotic cell (including but not limited to *E. coli*) or eukaryotic cells (including but not limited to yeast cells, mammalian cells, avian cells, amphibian cells, plant cells, fish cells, and insect cells). Host cells can be for example, transformed with the heterologous polynucleotide.

The term "plant" includes whole plants, shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid, and hemizygous.

DETAILED DESCRIPTION OF THE INVENTION

I. Introduction

As detailed herein, a collection of PYR1 mutants having all possible single amino acid substitutions in residues of the receptor-PP2C interface were screened to identify mutants that lower the concentration of ABA required to induce a detectable interaction between PYR1 and the PP2C HAB1. Based on these results, we describe mutations in highly conserved residues of the receptor-PP2C interface that substantially increase the receptor's sensitivity to ABA.

Thus, in one aspect, the disclosure relates to mutated PYR/PYL receptor polypeptides that are hypersensitive, i.e., the mutated receptors are more responsive to the ABA compared to a corresponding wild-type PYR/PYL polypeptide. In some embodiments, the hypersensitive PYR/PYL mutants described herein are not constitutively active, i.e., they do not activate the ABA signaling pathway in the absence of ABA. Hypersensitive PYR/PYL receptor mutants are beneficial for finely regulating the activation of ABA signaling and phenotypes associated with ABA responsiveness, such as stress tolerance (e.g., drought tolerance).

In another aspect, expression in a plant of one or more hypersensitive mutant PYR/PYl receptor polypeptides as described here will result in a plant with increased ABA sensitivity, and in some embodiments, higher stress tolerance or other phenotypes associated with ABA responsiveness.

Also provided herein are methods and reagents for producing a plant (e.g., a maize plant) having increased sensitivity to abscisic acid. In some embodiments, the method comprises introducing a mutation into a polynucleotide encoding a PYR/PYL polypeptide, wherein the mutation is introduced in situ in the genome of the plant using RNA directed genome modification methods.

II. Hypersensitive PYR/PYL Receptor Polypeptides

A wide variety of wild-type (naturally occurring) PYR/PYL polypeptide sequences are known in the art. Although PYR1 was originally identified as an abscisic acid (ABA) receptor in Arabidopsis, in fact PYR1 is a member of a group of at least 14 proteins (PYR/PYL proteins) in the same protein family in Arabidopsis that also mediate ABA signaling. This protein family is also present in other plants (see, e.g., SEQUENCE LISTING) and is characterized in part by the presence of one or more or all of a polyketide cyclase domain 2 (PF10604), a polyketide cyclase domain 1 (PF03364), and a Bet V I domain (PF00407). START/Bet v 1 superfamily domain are described in, for example, Radauer, BMC Evol. Biol. 8:286 (2008). In some embodiments, a wild-type PYR/PYL receptor polypeptide comprises any of SEQ ID NOs:1-89. In some embodiments, a wild-type PYR/PYL receptor polypeptide is substantially identical to (e.g., at least 50%, 55%, 60%, 65%, 70%, 75%, 80%, 85%, 90%, 91%, 92%, 93%, 94% 95%, 96%, 97%, 98%, or 99% identical to) any of SEQ ID NOs:1-89.

PYR/PYL receptor proteins have a conserved START-domain ligand-binding pocket flanked by two loops called the "gate" and the "latch" (Melcher, K. et al., Nature 462 (2009)). ABA binds to a PYR/PYL receptor protein at the ligand-binding pocket and ABA binding induces closure of the loops to seal ABA inside the ligand-binding pocket. The ligand-binding pocket of a PYR/PYL receptor polypeptide comprises amino acid residues that are in close proximity (e.g., within about 5 Å) to a PYR/PYL ligand (e.g., ABA) or a ligand-contacting water molecule when the ligand is bound to the PYR/PYL receptor. There are 25 residues that make up the PYR1 ligand-binding pocket. The residues of the ligand-binding pocket are also highly conserved among other PYR/PYL family members.

PYR/PYL receptor proteins directly bind to type 2 protein phosphatases (PP2Cs) and thus also contain a PP2C binding interface. The PP2C binding interface of a PYR/PYL receptor polypeptide comprises amino acid residues that are in close proximity (e.g., within about 5 Å) to PP2C when PP2C, the PYR/PYL receptor, and ABA are all bound together in a ternary complex. There are 25 residues that make up the PYR1 PP2C binding interface. The residues of the PP2C binding interface are also highly conserved among other PYR/PYL family members.

Hypersensitive PYR/PYL receptor polypeptides are non-naturally-occurring variants from naturally occurring (i.e., wild-type) PYR/PYL receptor polypeptides, wherein the variant (mutant) PYR/PYL receptor polypeptide is able to bind to and/or inhibit the activity of a PP2C in the presence of abscisic acid to a greater extent than a control PYR/PYL receptor polypeptide in the presence of the same concentration of ABA. In some embodiments, a hypersensitive variant (mutant) PYR/PYL polypeptide as described herein does not exhibit detectable binding to a PP2C (e.g., HAB1) in the absence of ABA (e.g., as measured in a two-hybrid assay). In some embodiments, a hypersensitive variant (mutant) PYR/PYL polypeptide as described herein does not inhibit PP2C (e.g., HAB1) activity in the absence of ABA (e.g., as measured in an enzymatic assay with a variant PYR/PYL polypeptide and PP2C and determining that there is not a detectable decrease in phosphatase activity as compared to PP2C alone).

In some embodiments, the PP2C to which a hypersensitive PYR/PYL receptor polypeptide as described herein binds and/or inhibits is a PP2C within the "clade A" cladogram. See, e.g., Antoni et al., Plant Physiology, 2012, 158:970-980. In some embodiments, the PP2C is HAB1, ABI1, ABI2, or PP2CA. In some embodiments, the PP2C is HAB1.

Hypersensitive active PYR/PYL receptor polypeptides as described herein comprise one or more amino acid substitutions compared to a wild type PYR/PYL receptor polypeptide. In some embodiments, a hypersensitive PYR/PYL receptor polypeptide is substantially identical to (e.g., at least 50%, 55%, 60%, 65%, 70%, 75%, 80%, 85%, 90%, 91%, 92%, 93%, 94% 95%, 96%, 97%, 98%, or 99% identical to) any of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, or 89 and comprises 1, 2, 3, 4, or more mutations (e.g., amino acid substitutions) as described herein.

In some embodiments, a hypersensitive PYR/PYL receptor polypeptide comprises a mutation (e.g., substitution) at one or more positions corresponding to K63, I82, I84, D154, M158, T162, L166, or K170 as set forth in SEQ ID NO:1. In some embodiments, a hypersensitive PYR/PYL receptor polypeptide comprises mutations (e.g., substitutions) at two, three, four, five or more positions corresponding to K63, I82, I84, D154, M158, T162, L166, or K170 as set forth in SEQ ID NO:1. Any of these one or more mutations can be made in any wild-type PYR/PYL polypeptide, for example, in the polypeptides of any of SEQ ID NOs:1-89, or in polypeptides substantially identical to any of SEQ ID NOs:1-89, or in polypeptides comprising any of SEQ ID NOs:90-100.

In some embodiments, a hypersensitive PYR/PYL receptor polypeptide comprises a mutation (e.g., substitution) at position K63 (corresponding to the position in SEQ ID NO:1). For position K63, hypersensitive mutations will include K63D, K63E, and K63Q substitutions. In some embodiments, a hypersensitive PYR/PYL receptor polypeptide comprises a K63D substitution. In some embodiments, a hypersensitive PYR/PYL receptor polypeptide comprises a K63E substitution. In some embodiments, a hypersensitive PYR/PYL receptor polypeptide comprises a K63Q substitution. Any of these mutations can be made in any wild-type PYR/PYL polypeptide, for example, in the polypeptides of any of SEQ ID NOs:1-89, or in polypeptides substantially identical to any of SEQ ID NOs:1-89, or in polypeptides comprising any of SEQ ID NOs:90-100.

In some embodiments, a hypersensitive PYR/PYL receptor polypeptide comprises a mutation (e.g., substitution) at position I82 (corresponding to the position in SEQ ID NO:1). For position I82, hypersensitive mutations will include I82A, I82F, I82K, and I82S substitutions. In some embodiments, a hypersensitive PYR/PYL receptor polypeptide comprises an I82A substitution. In some embodiments, a hypersensitive PYR/PYL receptor polypeptide comprises an I82F substitution. In some embodiments, a hypersensitive PYR/PYL receptor polypeptide comprises a I82K substitution. In some embodiments, a hypersensitive PYR/PYL receptor polypeptide comprises an I82S substitution. Any of these mutations can be made in any wild-type PYR/PYL polypeptide, for example, in the polypeptides of any of SEQ ID NOs:1-89, or in polypeptides substantially identical to any of SEQ ID NOs:1-89, or in polypeptides comprising any of SEQ ID NOs:90-100.

In some embodiments, a hypersensitive PYR/PYL receptor polypeptide comprises a mutation (e.g., substitution) at position I84 (corresponding to the position in SEQ ID NO:1). For position I84, hypersensitive mutations will include I84A, I84D, I84N, I84R, I84S, and I84T substitutions. In some embodiments, a hypersensitive PYR/PYL receptor polypeptide comprises an I84A substitution. In some embodiments, a hypersensitive PYR/PYL receptor polypeptide comprises an I84D substitution. In some embodiments, a hypersensitive PYR/PYL receptor polypeptide comprises an I84N substitution. In some embodiments, a hypersensitive PYR/PYL receptor polypeptide comprises an I84R substitution. In some embodiments, a hypersensitive PYR/PYL receptor polypeptide comprises an I84S substitution. In some embodiments, a hypersensitive PYR/PYL receptor polypeptide comprises an I84T substitution. Any of these mutations can be made in any wild-type PYR/PYL polypeptide, for example, in the polypeptides of any of SEQ ID NOs:1-89, or in polypeptides substantially identical to any of SEQ ID NOs:1-89, or in polypeptides comprising any of SEQ ID NOs:90-100. In some embodiments, a hypersensitive PYR/PYL receptor polypeptide does not comprise an I84E, an I84H, an I84K, an I84P, or an I84Q substitution.

In some embodiments, a hypersensitive PYR/PYL receptor polypeptide comprises a mutation (e.g., substitution) at position D154 (corresponding to the position in SEQ ID NO:1). For position D154, hypersensitive mutations will include D154E, D154F, D154G, D154H, D154K, D154M, D154Q, D154R, D154W, and D154Y substitutions. In some embodiments, a hypersensitive PYR/PYL receptor polypeptide comprises a D154E substitution. In some embodiments, a hypersensitive PYR/PYL receptor polypeptide comprises a D154F substitution. In some embodiments, a hypersensitive PYR/PYL receptor polypeptide comprises a D154H substitution. In some embodiments, a hypersensitive PYR/PYL receptor polypeptide comprises a D154K substitution. In some embodiments, a hypersensitive PYR/PYL receptor polypeptide comprises a D154M substitution. In some embodiments, a hypersensitive PYR/PYL receptor polypeptide comprises a D154Q substitution. In some embodiments, a hypersensitive PYR/PYL receptor polypeptide comprises a D154R substitution. In some embodiments, a hypersensitive PYR/PYL receptor polypeptide comprises a D154W substitution. In some embodiments, a hypersensitive PYR/PYL receptor polypeptide comprises a D154Y substitution. Any of these mutations can be made in any wild-type PYR/PYL polypeptide, for example, in the polypeptides of any of SEQ ID NOs:1-89, or in polypeptides substantially identical to any of SEQ ID NOs:1-89, or in polypeptides comprising any of SEQ ID NOs:90-100.

In some embodiments, a hypersensitive PYR/PYL receptor polypeptide comprises a mutation (e.g., substitution) at position M158 (corresponding to the position in SEQ ID NO:1). For position M158, hypersensitive mutations will include M58A, M158D, M158G, M158H, M158N, and M158W substitutions. In some embodiments, a hypersensitive PYR/PYL receptor polypeptide comprises an M158A substitution. In some embodiments, a hypersensitive PYR/PYL receptor polypeptide comprises an M158D substitution. In some embodiments, a hypersensitive PYR/PYL receptor polypeptide comprises an M158G substitution. In some embodiments, a hypersensitive PYR/PYL receptor polypeptide comprises an M158H substitution. In some embodiments, a hypersensitive PYR/PYL receptor polypeptide comprises an M158N substitution. In some embodiments, a hypersensitive PYR/PYL receptor polypeptide comprises an M158W substitution. In some embodiments, a hypersensitive PYR/PYL receptor polypeptide comprises an M158D/G/H/W substitution. Any of these mutations can be made in any wild-type PYR/PYL polypeptide, for example, in the polypeptides of any of SEQ ID NOs:1-89, or in polypeptides substantially identical to any of SEQ ID NOs:1-89, or in polypeptides comprising any of SEQ ID NOs:90-100. In some embodiments, a hypersensitive PYR/PYL receptor polypeptide does not comprise an M158C, an M158I, an M158S, an M158T. or an M158V substitution.

In some embodiments, a hypersensitive PYR/PYL receptor polypeptide comprises a mutation (e.g., substitution) at position T162 (corresponding to the position in SEQ ID NO:1). For position T162, hypersensitive mutations will include T162H, T162K, T162L, T162M, T162W, and T162Y substitutions. In some embodiments, a hypersensitive PYR/PYL receptor polypeptide comprises a T162H substitution. In some embodiments, a hypersensitive PYR/PYL receptor polypeptide comprises an T162K substitution. In some embodiments, a hypersensitive PYR/PYL receptor polypeptide comprises a T162L substitution. In some embodiments, a hypersensitive PYR/PYL receptor polypeptide comprises a T162M substitution. In some embodiments, a hypersensitive PYR/PYL receptor polypeptide comprises a T162W substitution. In some embodiments, a hypersensitive PYR/PYL receptor polypeptide comprises a T162Y substitution. Any of these mutations can be made in any wild-type PYR/PYL polypeptide, for example, in the polypeptides of any of SEQ ID NOs:1-89, or in polypeptides substantially identical to any of SEQ ID NOs:1-89, or in polypeptides comprising any of SEQ ID NOs:90-100. In some embodiments, a hypersensitive PYR/PYL receptor polypeptide does not comprise a T162F substitution.

In some embodiments, a hypersensitive PYR/PYL receptor polypeptide comprises a mutation (e.g., substitution) at position L166 (corresponding to the position in SEQ ID NO:1). For position L166, hypersensitive mutations will include L166A, L166E, L166G, L166H, L166K, L166M, L166N, L166P, L166Q, L166R, L166S, L166T, and L166W substitutions. In some embodiments, a hypersensitive PYR/PYL receptor polypeptide comprises an L166A substitution. In some embodiments, a hypersensitive PYR/PYL receptor polypeptide comprises an L166E substitution. In some embodiments, a hypersensitive PYR/PYL receptor polypeptide comprises an L166G substitution. In some embodiments, a hypersensitive PYR/PYL receptor polypeptide comprises an L166H substitution. In some embodiments, a hypersensitive PYR/PYL receptor polypeptide comprises an L166K substitution. In some embodiments, a hypersensitive PYR/PYL receptor polypeptide comprises an L166M substitution. In some embodiments, a hypersensitive PYR/PYL receptor polypeptide comprises an L166N substitution. In some embodiments, a hypersensitive PYR/PYL receptor polypeptide comprises an L166P substitution. In some embodiments, a hypersensitive PYR/PYL receptor polypeptide comprises an L166Q substitution. In some embodiments, a hypersensitive PYR/PYL receptor polypeptide comprises an L166R substitution. In some embodiments, a hypersensitive PYR/PYL receptor polypeptide comprises an L166S substitution. In some embodiments, a hypersensitive PYR/PYL receptor polypeptide comprises an L166T substitution. In some embodiments, a hypersensitive PYR/PYL receptor polypeptide comprises an L166W substitution. In some embodiments, a hypersensitive PYR/PYL receptor polypeptide comprises a L166G/H/K/N/Q/R/S/T substitution. Any of these mutations can be made in any wild-type PYR/PYL polypeptide, for example, in the polypeptides of any of SEQ ID NOs:1-89, or in polypeptides substantially identical to any of SEQ ID NOs:1-89, or in polypeptides comprising any of SEQ ID NOs:90-100. In some embodiments, a hypersensitive PYR/PYL receptor polypeptide does not comprise an L166F or L166Y substitution.

In some embodiments, a hypersensitive PYR/PYL receptor polypeptide comprises a mutation (e.g., substitution) at position K170 (corresponding to the position in SEQ ID NO:1). For position K170, hypersensitive mutations will include K170A, K170C, K170D, K170E, K170F, K170G, K170H, K170I, K170M, K170N, K170Q, K170R, K170S, K170T, K170V, and K170Y substitutions. In some embodiments, a hypersensitive PYR/PYL receptor polypeptide comprises a K170A substitution. In some embodiments, a hypersensitive PYR/PYL receptor polypeptide comprises a K170C substitution. In some embodiments, a hypersensitive PYR/PYL receptor polypeptide comprises a K170D substitution. In some embodiments, a hypersensitive PYR/PYL receptor polypeptide comprises a K170E substitution. In some embodiments, a hypersensitive PYR/PYL receptor polypeptide comprises a K170F substitution. In some embodiments, a hypersensitive PYR/PYL receptor polypeptide comprises a K170G substitution. In some embodiments, a hypersensitive PYR/PYL receptor polypeptide comprises a K170H substitution. In some embodiments, a hypersensitive PYR/PYL receptor polypeptide comprises a K170I substitution. In some embodiments, a hypersensitive PYR/PYL receptor polypeptide comprises a K170M substitution. In some embodiments, a hypersensitive PYR/PYL receptor polypeptide comprises a K170N substitution. In some embodiments, a hypersensitive PYR/PYL receptor polypeptide comprises a K170Q substitution. In some embodiments, a hypersensitive PYR/PYL receptor polypeptide comprises a K170R substitution. In some embodiments, a hypersensitive PYR/PYL receptor polypeptide comprises a K170S substitution. In some embodiments, a hypersensitive PYR/PYL receptor polypeptide comprises a K170T substitution. In some embodiments, a hypersensitive PYR/PYL receptor polypeptide comprises a K170V substitution. In some embodiments, a hypersensitive PYR/PYL receptor polypeptide comprises a K170Y substitution. In some embodiments, a hypersensitive PYR/PYL receptor polypeptide comprises a K170A/C/D/E/F/G/I/M/S/T/V/Y substitution. Any of these mutations can be made in any wild-type PYR/PYL polypeptide, for example, in the polypeptides of any of SEQ ID NOs:1-89, or in polypeptides substantially identical to any of SEQ ID NOs:1-89, or in polypeptides comprising any of SEQ ID NOs:90-100. In some embodiments, a hypersensitive PYR/PYL receptor polypeptide does not comprise a K159W substitution.

Any of the mutations described herein can be made in any wild-type PYR/PYL polypeptide, for example, in the polypeptides of any of SEQ ID NOs:1-89 or in polypeptides substantially identical to any of SEQ ID NOs:1-89 or comprising any of SEQ ID NOs:90-100. Analogous amino acid substitutions can be made, for example, in PYR/PYL receptors other than PYR1 by aligning the PYR/PYL receptor polypeptide sequence to be mutated with the PYR1 receptor polypeptide sequence as set forth in SEQ ID NO:1. As a non-limiting example, an amino acid substitution in PYL2 that is analogous to the amino acid substitution I84 in PYR1 as set forth in SEQ ID NO:1 can be determined by aligning the amino acid sequences of PYL2 (SEQ ID NO:3) and PYR1 (SEQ ID NO:1) and identifying position I88 in PYL2 as aligning with amino acid position I84 of PYR1 (SEQ ID NO:1). It will be appreciated that the polypeptides can be further mutated (e.g., with conservative mutations, e.g., outside active sites) without substantially affecting activity.

The extent to which one or more amino acid substitutions in the PYR/PYL receptor activity renders the receptor hypersensitive to ABA can be quantitatively measured, for example by assaying phosphatase activity in the presence of ABA and the PYR/PYL receptor comprising one or more amino acid substitutions and comparing the phosphatase activity to that of a control PYR/PYL receptor. A control PYR/PYL receptor will typically be the wild-type PYR/PYL polypeptide most similar to the mutated PYR/PYL polypeptide. In some embodiments, e.g., when the starting protein is not a wild-type PYR/PYL polypeptide, the control PYR/PYL polypeptide can be substantially identical (e.g., at least 90, 95, or 98% identical) to the test PYR/PYL polypeptide (i.e., suspected of being hypersensitive) and having the wild-type amino acid at the corresponding position. For example, if the mutant PYR/PYL receptor has a mutation of I84X, where X is any non-I amino acid, the control would have I84 at the same position but would otherwise be identical to the mutant PYR/PYL receptor.

In some embodiments, a mutated PYR/PYL receptor polypeptide comprises two or more amino acid substitutions as described herein. In some embodiments, the mutated PYR/PYL receptor polypeptide comprises an amino acid substitution at two or more positions corresponding to K63X, I82X, I84X, D154X, M158X, T162X, L166X, or K170X in PYR1 as set forth in SEQ ID NO:1, where X is an amino acid described herein that confers hypersensitivity (e.g., as described in the Example section below).

Consensus Sequences

PYR/PYL receptor proteins can be described by reference to sequence alignments that identify conserved amino acid or motifs (i.e., where alteration in sequences may alter protein function) and regions where variation occurs in alignment of sequences (i.e., where variation of sequence is not likely to significantly affect protein activity). SEQ ID NOs:90-100 provide consensus sequences useful for identifying wild-type PYR/PYL receptor polypeptides. The consensus sequences of SEQ ID NOs:90-92 were generated by aligning all 14 members of the *Arabidopsis* PYR/PYL receptor protein family. In the consensus sequences of SEQ ID NOs:90-92, the capitalized letter represents an amino acid residue that is absolutely conserved among all 14 members of the *Arabidopsis* PYR/PYL receptor protein family, while "x" represents an amino acid residue that is not absolutely conserved among all 14 family members and which can be any amino acid. It will be appreciated that when selecting an amino acid to insert at a position marked by an "x" that in some embodiments, the amino acid is selected from those amino acids found at the corresponding position in a wild-type or mutated PYR/PYL protein.

```
PYR1 to PYL13
                                        (SEQ ID NO: 90)
CxSxxxxxxxAPxxxxWxxxxxFxxPxxxxxFxxxC (SEQ ID NO: 91)
GxxRxVxxxSxxPAxxSxExLxxxD (SEQ ID NO: 92)
ESxxVDxPxGxxxxxTxxFxxxxxxxNLxxL
```

Consensus sequence CxSxxxxxxxAPxxxxWxxxxxFxxPxxxxxFxxxC (SEQ ID NO:90) comprises the region corresponding to amino acids 30 to 65 of PYR1 (SEQ ID NO:1). Consensus sequence GxxRxVxxxSxxPAxxSxExLxxxD (SEQ ID NO:191) comprises the region corresponding to amino acids 76 to 100 of PYR1 (SEQ ID NO:1). ESxxVDxPxGxxxxxTxxFxxxxxxxNLxxL (SEQ ID NO:92) comprises the region corresponding to amino acids 141 to 171 of PYR1 (SEQ ID NO:1).

In some embodiments, more specific consensus sequences can be represented by aligning subsets of the 14 members of the *Arabidopsis* PYR/PYL proteins, as shown below. The consensus sequences of SEQ ID NOs:93-95 were generated by aligning the *Arabidopsis* PYR/PYL receptor proteins PYR1, PYL1, PYL2, PYL3, PYL4A, PYL5, and PYL6. The consensus sequences of SEQ ID NOs:96-98 were generated by aligning the *Arabidopsis* PYR/PYL receptor proteins PYL7, PYL8, PYL9, and PYL10. The consensus sequences of SEQ ID NOs:99-100 were generated by aligning the *Arabidopsis* PYR/PYL receptor proteins PYL11, PYL12, and PYL13.

```
PYR1-PYL6
                                        (SEQ ID NO: 93)
HxxxxxxxxCxSxxxxxxxAPxxxxWxxxxxFxxPxxYKxFxxxC (SEQ ID NO: 94)
VGRxVxVxSGLPAxxSxExLxxxDxxxxxxxxFxxxGGxHRLxNYxSVT
```

```
                                        (SEQ ID NO: 95)
VxESYxVDxPxGNxxxxTxxFxDxxxxxNLQxL PYL7-PYL10
                                        (SEQ ID NO: 96)
HxHxxxxxQCxSxLVKxIxAPxHxVWSxVRRFDxPQKYKPFxSRCxVxGx (SEQ ID NO: 97)
ExGxxREVxxKSGLPATxSTExLExLDDxEHILxIxIxGGDHRLKNYSSx
xxxHxExIxGxxGTx (SEQ ID NO: 98)
xxESFVVDVPxGNTKxxTCxFVExLIxCNLxSLAxxxERL PYL11-PYL13
                                        (SEQ ID NO: 99)
CxSxxVxTIxAPLxLVWSILRxFDxPxxxxxFVKxCxxxSGxGG (SEQ ID NO: 100)
GSVRxVTxVSxxPAxFSxERLxELDDESHVMxxSIIGxHRLVNYxSKT
```

In some embodiments, a hypersensitive PYR/PYL receptor polypeptide comprises one or more of SEQ ID NOs:90, 91, 92, 93, 94, 95, 96, 97, 98, 99, or 100 and comprises 1, 2, 3, 4, or more mutations (e.g., amino acid substitutions) as described herein (e.g., at a position corresponding to K63, I82, I84, D154, M158, T162, L166, or K170 as set forth in SEQ ID NO:1).

Embodiments of the present invention provide for use of the above proteins and/or nucleic acid sequences, encoding such polypeptides, in the methods and compositions (e.g., expression cassettes, transgenic plants, plants with in situ PYR/PYL modifications, etc.) of the present invention. The isolation of a polynucleotide sequence encoding a plant wild-type PYR/PYL receptor (e.g., from plants where PYR/PYL sequences have not yet been identified) may be accomplished by a number of techniques. For instance, oligonucleotide probes based on the PYR/PYL coding sequences disclosed (e.g., as listed in the SEQUENCE LISTING) here can be used to identify the desired wild-type PYR/PYL gene in a cDNA or genomic DNA library. To construct genomic libraries, large segments of genomic DNA are generated by random fragmentation, e.g., using restriction endonucleases, and are ligated with vector DNA to form concatemers that can be packaged into the appropriate vector. To prepare a cDNA library, mRNA is isolated from the desired tissue, such as a leaf from a particular plant species, and a cDNA library containing the gene transcript of interest is prepared from the mRNA. Alternatively, cDNA may be prepared from mRNA extracted from other tissues in which PYR/PYL gene is expressed.

The cDNA or genomic library can then be screened using a probe based upon the sequence of a PYR/PYL gene disclosed here. Probes may be used to hybridize with genomic DNA or cDNA sequences to isolate homologous genes in the same or different plant species. Alternatively, antibodies raised against a polypeptide can be used to screen an mRNA expression library.

Alternatively, the nucleic acids encoding PYR/PYL can be amplified from nucleic acid samples using amplification techniques. For instance, polymerase chain reaction (PCR) technology can be used to amplify the coding sequences of PYR/PYL directly from genomic DNA, from cDNA, from genomic libraries or cDNA libraries. PCR and other in vitro amplification methods may also be useful, for example, to clone polynucleotide sequences encoding PYR/PYL to be expressed, to make nucleic acids to use as probes for detecting the presence of the desired mRNA in samples, for nucleic acid sequencing, or for other purposes. For a general overview of PCR see *PCR Protocols: A Guide to Methods and Applications* (Innis, M., Gelfand, D., Sninsky, J. and White, T., eds.), *Academic Press*, San Diego (1990). Appropriate primers and probes for identifying sequences from plant tissues are generated from comparisons of the sequences provided here with other related genes.

In some embodiments, the partial or entire genome of a number of plants has been sequenced and open reading frames identified. By a BLAST search, one can identify the coding sequence for wild-type PYR/PYL in various plants.

III. Methods of Making Hypersensitive PYR/PYL Receptor Polypeptides

In another aspect, methods of making ABA hypersensitive PYR/PYL receptor polypeptides comprising one or more amino acid substitutions as described herein are provided. In some embodiments, the method comprises mutagenizing a wild-type PYR/PYL receptor and determining whether the mutagenized PYR/PYL receptor is hypersensitive to ABA.

Mutated PYR/PYL receptor polypeptides can be constructed by mutating the DNA sequences that encode the corresponding wild-type PYR/PYL receptor polypeptide (e.g., a wild-type PYR/PYL polypeptide of any of SEQ ID NOs:1-89 or having any of SEQ ID NOs:90-100, or a corresponding variant from which a mutant PYR/PYL receptor polypeptide as described herein is derived), such as by using site-directed or random mutagenesis. Nucleic acid molecules encoding the wild-type PYR/PYL receptor polypeptide can be mutated by a variety of polymerase chain reaction (PCR) techniques well-known to one of ordinary skill in the art. (See. e.g., PCR Strategies (M. A. Innis, D. H. Gelfand, and J. J. Sninsky eds., 1995, Academic Press. San Diego, Calif.) at Chapter 14; *PCR Protocols: A Guide to Methods and Applications* (M. A. Innis, D. H. Gelfand, J. J. Sninsky, and T. J. White eds., Academic Press, NY, 1990).

As a non-limiting example, mutagenesis may be accomplished using site-directed mutagenesis, in which point mutations, insertions, or deletions are made to a DNA template. Kits for site-directed mutagenesis are commercially available, such as the QuikChange Site-Directed Mutagenesis Kit (Stratagene). Briefly, a DNA template to be mutagenized is amplified by PCR according to the manufacturer's instructions using a high-fidelity DNA polymerase (e.g., Pfu Turbo™) and oligonucleotide primers containing the desired mutation. Incorporation of the oligonucleotides generates a mutated plasmid, which can then be transformed into suitable cells (e.g., bacterial or yeast cells) for subsequent screening to confirm mutagenesis of the DNA.

As another non-limiting example, mutagenesis may be accomplished by means of error-prone PCR amplification (ePCR), which modifies PCR reaction conditions (e.g., using error-prone polymerases, varying magnesium or manganese concentration, or providing unbalanced dNTP ratios) in order to promote increased rates of error in DNA replication. Kits for ePCR mutagenesis are commercially available, such as the GeneMorph® PCR Mutagenesis kit (Stratagene) and Diversify®® PCR Random Mutagenesis Kit (Clontech). Briefly, DNA polymerase (e.g., Taq polymerase), salt (e.g., MgCl2, MgSO4, or MnSO4), dNTPs in unbalanced ratios, reaction buffer, and DNA template are combined and subjected to standard PCR amplification according to manufacturer's instructions. Following ePCR amplification, the reaction products are cloned into a suitable vector to construct a mutagenized library, which can then be transformed into suitable cells (e.g., yeast cells) for subsequent screening (e.g., via a two-hybrid screen) as described below.

Alternatively, mutagenesis can be accomplished by recombination (i.e. DNA shuffling). Briefly, a shuffled mutant library is generated through DNA shuffling using in vitro homologous recombination by random fragmentation of a parent DNA followed by reassembly using PCR, resulting in randomly introduced point mutations. Methods of performing DNA shuffling are known in the art (see. e.g., Stebel, S. C. et al., *Methods Mol Biol* 352:167-190 (2007)).

Optionally, multiple rounds of mutagenesis may be performed in order to improve the efficiency of mutant proteins isolated. Thus, in some embodiments, PYR/PYL mutants isolated from ePCR and subsequent screening may be pooled and used as templates for later rounds of mutagenesis.

In some embodiments, the variants are generated by exposing a plant of plant seeds or cells to a mutagen selecting the plant or cell carrying a hypersensitive PYR/PYL polypeptide as described herein by phenotype or genotype. Examples of mutagens include. e.g., chemical mutagens (e.g., EMS) or radiological mutagens. Variants having a desired mutation can be selected based on phenotype of genotype (e.g., by using TILLING techniques).

In some embodiments, the method comprises mutagenizing a wild-type PYR/PYL receptor in situ and determining whether the mutagenized PYR/PYL receptor is hypersensitive to ABA. Mutated PYR/PYL receptor polypeptides can be constructed by mutating the DNA sequences that encode the corresponding wild-type PYR/PYL receptor polypeptide (e.g., a wild-type PYR/PYL polypeptide of any of SEQ ID NOs:1-89, having any of SEQ ID NOs:90-100, or a corresponding variant from which the mutant PYR/PYL receptor polypeptide of the invention is derived), such as by using site-directed or random mutagenesis.

IV. Screening for Hypersensitive PYR/PYL Receptor Polypeptides

The hypersensitivity of the mutant PYR/PYL receptors described herein can be measured in several alternative ways. When expressed in yeast, most wild-type PYR/PYL receptors will only bind to the type 2 protein phosphatase (PP2C) HAB1 ("Homology to ABI1") or other PP2Cs when the appropriate yeast cells are grown in the presence of ABA. Thus, in some embodiments, hypersensitivity can be measured by determining the ability of a PYR/PYL mutant receptor, expressed in yeast, to bind to and inactivate PP2C in yeast in the presence of ABA to a greater extent than a control PYR/PYL receptor expressed in yeast in the presence of ABA. In some embodiments, the hypersensitive mutant PYR/PYL receptor comprises mutations that result in the mutated receptor inhibiting the activity of the PP2C in a phosphatase assay in the presence of ABA (e.g., ABA at a concentration of 0.5 µM, 1 µM, 2 µM, or 5 µM) at least about 10%, at least about 20%, at least about 30%, at least about 40%, at least about 50%, at least about 60%, at least about 70%, at least about 80% or more as compared to a wild-type or other control PYR/PYL receptor in the presence of the same concentration of ABA. Several test concentrations ranging from low nM to low µM (e.g., 0.5 µM, 1 µM, 2 µM, or 5 µM) could be conducted to infer $IC_{50}$ values and the $IC_{50}$ values of hypersensitive mutants are lower than appropriate wild type controls.

Alternatively, cell-based or plant-based methods of screening can be used. For example, cells that naturally express a wild-type PYR/PYL receptor polypeptide or that recombinantly express a wild-type or mutated PYR/PYL receptor polypeptide can be used. In some embodiments, the cells used are plant cells, animal cells, bacterial cells, fungal cells, including but not limited to yeast cells, insect cells, or mammalian cells. In general terms, the screening methods involve comparing the activity of a mutated PYR/PYL receptor polypeptide to the activity of a wild-type PYR/PYL receptor polypeptide in the presence of ABA, e.g., by comparing ABA-regulated gene expression in the wild-type and mutant PYR/PYL receptor-expressing cells or plants.

One exemplary assay involves testing whether a mutated PYR/PYL receptor can bind to a type 2 protein phosphatase (PP2C) (e.g. HAB1) in the presence of ABA. Binding assays can involve contacting a mutated PYR/PY1 receptor polypeptide with a PP2C and allowing sufficient time for the PYR/PYL receptor and PP2C to form a binding complex. Any binding complexes formed can be detected using any of a number of established analytical techniques. Protein binding assays include, but are not limited to, methods that measure co-precipitation or co-migration on non-denaturing SDS-polyacrylamide gels, and co-migration on Western blots (see, e.g., Bennet. J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89. Other binding assays involve the use of mass spectrometry or NMR techniques to identify molecules bound to the PYR/PYL polypeptide. The PYR/PYL polypeptide protein utilized in such assays can be naturally expressed, cloned or synthesized.

In some embodiments, mammalian or yeast two-hybrid approaches (see, e.g., Bartel, P. L. et. al. *Methods Enzymol.* 254:241 (1995)) can be used to identify polypeptides or other molecules that interact or bind when expressed together in a cell. In some embodiments, a hypersensitive PYR/PYL polypeptide is identified in a two-hybrid assay between a PYR/PYL polypeptide and a PP2C polypeptide, wherein the PYR/PYL polypeptide and the PP2C bind in the presence of ABA.

In another exemplary assay, the level of activity of a mutated PYR/PYL receptor polypeptide can be determined using an enzymatic phosphatase assay, in which the PYR/PYL receptor and PP2C are incubated in the presence of ABA. In this type of assay, a decrease in phosphatase activity in the presence of ABA to a greater extent than occurred for a control PYR/PYL receptor is indicative of hypersensitive PYR/PYL receptor. A decrease in phosphatase activity can be determined and quantified using any detection reagent known in the art, e.g., a colorimetric detection reagent such as para-nitrophenylphosphate.

Hypersensitive PYR/PYL receptor polypeptides that are initially identified by any of the foregoing screening methods can be further tested to validate the apparent activity and/or determine other biological effects of the hypersensitive PYR/PYL receptor polypeptide. In some cases, the PYR/PYL receptor polypeptide is tested for the ability to affect plant stress (e.g., drought tolerance and/or high salt tolerance), seed germination, or another phenotype affected by ABA. A number of such assays and phenotypes are known in the art and can be employed according to the methods of the invention.

V. Recombinant Expression Vectors

Once a polynucleotide encoding a mutated PYR/PYL receptor polypeptide is obtained, it can also be used to prepare an expression cassette for expressing the mutated PYR/PYL receptor polypeptide in a transgenic plant, directed by a heterologous promoter. Increased expression of mutated PYR/PYL polynucleotide is useful, for example, to produce plants that selectively activate PYR/PYL receptors, thus enhancing stress tolerance.

Any of a number of means well known in the art can be used to drive mutated PYR/PYL activity or expression in plants. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. Alternatively, the mutated PYR/PYL polynucleotide can be expressed specifically in certain cell and/or tissue types within one or more organs (e.g., guard cells in leaves using a guard cell-specific promoter). Alternatively, the mutated PYR/PYL polynucleotide can be expressed constitutively (e.g., using the CaMV 35S promoter).

To use a polynucleotide sequence for a mutated PYR/PYL receptor polypeptide in the above techniques, recombinant DNA vectors suitable for transformation of plant cells are prepared. Techniques for transforming a wide variety of higher plant species are well known and described in the technical and scientific literature. See, e.g., Weising et al. *Ann. Rev. Genet.* 22:421-477 (1988). A DNA sequence coding for the mutated PYR/PYL receptor polypeptide preferably will be combined with transcriptional and translational initiation regulatory sequences which will direct the transcription of the sequence from the gene in the intended tissues of the transformed plant.

For example, a plant promoter fragment may be employed to direct expression of the mutated PYR/PYL polynucleotide in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the mutated PYR/PYL receptor protein in a specific tissue (tissue-specific promoters) or may be otherwise under more precise environmental control (inducible promoters). Examples of tissue-specific promoters under developmental control include promoters that initiate transcription only in certain tissues, such as leaves or guard cells (including but not limited to those described in WO 2005/085449; U.S. Pat. No. 6,653,535; Li et al., Sci China C *Life Sci.* 2005 April; 48(2):181-6; Husebye, et al., *Plant Physiol*, April 2002, Vol. 128, pp. 1180-1188; and Plesch, et al., *Gene*, Volume 249, Number 1, 16 May 2000, pp. 83-89(7)). Examples of environmental conditions that may affect transcription by inducible promoters include anaerobic conditions, elevated temperature, or the presence of light.

If proper protein expression is desired, a polyadenylation region at the 3'-end of the coding region should be included. The polyadenylation region can be derived from a naturally occurring PYR/PYL gene, from a variety of other plant genes, or from T-DNA.

The vector comprising the sequences (e.g., promoters or PYR/PYL coding regions) will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorsulfuron or Basta.

In some embodiments, the mutated PYR/PYL nucleic acid sequence is expressed recombinantly in plant cells. A variety of different expression constructs, such as expression cassettes and vectors suitable for transformation of plant cells, can be prepared. Techniques for transforming a wide variety of higher plant species are well known and described in the technical and scientific literature. See. e.g., Weising et al. *Ann. Rev. Genet.* 22:421-477 (1988). A DNA sequence coding for a PYR/PYL protein can be combined with cis-acting (promoter) and trans-acting (enhancer) transcriptional regulatory sequences to direct the timing, tissue type and levels of transcription in the intended tissues of the transformed plant. Translational control elements can also be used.

Embodiments of the present invention also provide for a mutated PYR/PYL nucleic acid operably linked to a promoter which, in some embodiments, is capable of driving the transcription of the PYR/PYL coding sequence in plants. The promoter can be, e.g., derived from plant or viral sources. The promoter can be, e.g., constitutively active, inducible, or tissue specific. In the construction of recombinant expression cassettes, vectors, or transgenics as described herein, different promoters can be chosen and employed to differentially direct gene expression, e.g., in some or all tissues of a plant or animal.

Constitutive Promoters

A fragment can be employed to direct expression of a mutated PYR/PYL nucleic acid in all transformed cells or tissues, e.g., as those of a regenerated plant. The term "constitutive regulatory element" means a regulatory element that confers a level of expression upon an operatively linked nucleic molecule that is relatively independent of the cell or tissue type in which the constitutive regulatory element is expressed. A constitutive regulatory element that is expressed in a plant generally is widely expressed in a large number of cell and tissue types. Promoters that drive expression continuously under physiological conditions are referred to as "constitutive" promoters and are active under most environmental conditions and states of development or cell differentiation.

A variety of constitutive regulatory elements useful for ectopic expression in a transgenic plant are well known in the art. The cauliflower mosaic virus 35S (CaMV 35S) promoter, for example, is a well-characterized constitutive regulatory element that produces a high level of expression in all plant tissues (Odell et al., *Nature* 313:810-812 (1985)). The CaMV 35S promoter can be particularly useful due to its activity in numerous diverse plant species (Benfey and Chua, *Science* 250:959-966 (1990); Futterer et al., *Physiol. Plant* 79:154 (1990); Odell et al., supra, 1985). A tandem 35S promoter, in which the intrinsic promoter element has been duplicated, confers higher expression levels in comparison to the unmodified 35S promoter (Kay et al., *Science* 236:1299 (1987)). Other useful constitutive regulatory elements include, for example, the cauliflower mosaic virus 19S promoter; the Figwort mosaic virus promoter; and the nopaline synthase (nos) gene promoter (Singer et al., *Plant Mol. Biol.* 14:433 (1990): An, *Plant Physiol.* 81:86 (1986)).

Additional constitutive regulatory elements including those for efficient expression in monocots also are known in the art, for example, the pEmu promoter and promoters based on the rice Actin-1 5' region (Last et al., *Theor. Appl. Genet.* 81:581 (1991); Mcelroy et al., *Mol. Gen. Genet.* 231:150 (1991); Mcelroy et al., *Plant Cell* 2:163 (1990)). Chimeric regulatory elements, which combine elements from different genes, also can be useful for ectopically expressing a nucleic acid molecule encoding a mutated PYR/PYL receptor protein (Comai et al., *Plant Mol. Biol.* 15:373 (1990)).

Other examples of constitutive promoters include the 1'- or 2'-promoter derived from T-DNA of *Agrobacterium tumafaciens* (see, e.g., Mengiste (1997) supra; O'Grady (1995) *Plant Mol. Biol.* 29:99-108); actin promoters, such as the *Arabidopsis* actin gene promoter (see, e.g., Huang (1997) *Plant Mol. Biol.* 1997 33:125-139); alcohol dehydrogenase (Adh) gene promoters (see. e.g., Millar (1996) *Plant Mol. Biol.* 31:897-904); ACT11 from *Arabidopsis* (Huang et al. *Plant Mo. Biol.* 33:125-139 (1996)), Cat3 from *Arabidopsis* (GenBank No. U43147, Zhong et al., *Mol. Gen. Genet.* 251:196-203 (1996)), the gene encoding stearoyl-acyl carrier protein desaturase from *Brassica napus* (Genbank No. X74782, Solocombe et al. *Plant Physiol.* 104:1167-1176 (1994)), GPc1 from maize (GenBank No. X15596, Martinez et al. *J. Mol. Biol* 208:551-565 (1989)), Gpc2 from maize (GenBank No. U45855, Manjunath et al., *Plant Mol. Biol.* 33:97-112 (1997)), other transcription initiation regions from various plant genes known to those of skill. See also Holtorf *Plant Mol. Biol.* 29:637-646 (1995).

Inducible Promoters

Alternatively, a plant promoter may direct expression of the mutated PYR/PYL polynucleotide under the influence of changing environmental conditions or developmental conditions. Examples of environmental conditions that may affect transcription by inducible promoters include anaerobic conditions, elevated temperature, drought, or the presence of light. Such promoters are referred to herein as "inducible" promoters. In some embodiments, an inducible promoter is one that is induced by one or more environmental stressors, including but not limited to, drought, freezing cold, and high salt. For example, the invention can incorporate a drought-specific promoter such as a drought-inducible promoter of maize (e.g., the maize rab17 drought-inducible promoter (Vilardell et al. (1991) *Plant Mol. Biol.* 17:985-993; Vilardell et al. (1994) *Plant Mol. Biol.* 24:561-569)); or alternatively a cold, drought, and high salt inducible promoter from potato (Kirch (1997) *Plant Mol. Biol.* 33:897-909) or from *Arabidopsis* (e.g., the rd29A promoter (Kasuga et al. (1999) *Nature Biotechnology* 17:287-291). Other environmental stress-inducible promoters include promoters from the following genes: Rab21, Wsi18, Lea3, Uge1, Dip1, and R1G1B in rice (Yi et al. (2010) *Planta* 232:743-754).

In some embodiments, a plant promoter is a stress-inducible promoter (e.g., a drought-, cold-, or salt-inducible promoter) that comprises a dehydration-responsive element (DRE) and/or an ABA-responsive element (ABRE), including but not limited to the rd29A promoter.

Alternatively, plant promoters that are inducible upon exposure to plant hormones, such as auxins, are used to express the mutated PYR/PYL polynucleotide. For example, the invention can use the auxin-response elements El promoter fragment (AuxREs) in the soybean (*Glycine max* L.) (Liu (1997) *Plant Physiol.* 115:397-407); the auxin-responsive *Arabidopsis* GST6 promoter (also responsive to salicylic acid and hydrogen peroxide) (Chen (1996) *Plant J.* 10: 955-966); the auxin-inducible parC promoter from tobacco (Sakai (1996) 37:906-913): a plant biotin response element (Streit (1997) *Mol. Plant Microbe Interact.* 10:933-937); and, the promoter responsive to the stress hormone abscisic acid (Sheen (1996) *Science* 274:1900-1902).

Plant promoters inducible upon exposure to chemicals reagents that may be applied to the plant, such as herbicides or antibiotics, are also useful for expressing the mutated PYR/PYL polynucleotide. For example, the maize In2-2 promoter, activated by benzenesulfonamide herbicide safeners, can be used (De Veylder (1997) *Plant Cell Physiol.* 38:568-577); application of different herbicide safeners induces distinct gene expression patterns, including expression in the root, hydathodes, and the shoot apical meristem. A PYR/PYL coding sequence can also be under the control of, e.g., a tetracycline-inducible promoter, e.g., as described with transgenic tobacco plants containing the Avena saliva L. (oat) arginine decarboxylase gene (Masgrau (1997) *Pant J.* 11:465-473): or, a salicylic acid-responsive element (Stange (1997) *Plant J.* 11:1315-1324; Uknes et al., *Plant Cell* 5:159-169 (1993); Bi et al., *Plant J.* 8:235-245 (1995)).

Examples of useful inducible regulatory elements include copper-inducible regulatory elements (Mett et al., *Proc. Natl. Acad. Sci. USA* 90:4567-4571 (1993); Furst et al., *Cell* 55:705-717 (1988)); tetracycline and chlor-tetracycline-inducible regulatory elements (Gatz et al., *Plant J.* 2:397-404 (1992); Röder et al., *Mol. Gen. Genet.* 243:32-38 (1994); Gatz, *Meth. Cell Biol.* 50:411-424 (1995)); ecdysone inducible regulatory elements (Christopherson et al., *Proc. Natl. Acad. Sci. USA* 89:6314-6318 (1992): Kreutzweiser et al., *Ecotoxicol. Environ. Safety* 28:14-24 (1994)); heat shock inducible regulatory elements (Takahashi et al., *Plant Physiol.* 99:383-390 (1992); Yabe et al., *Plant Cell Physiol.* 35:1207-1219 (1994): Ueda et al., *Mol. Gen. Genet.* 250: 533-539 (1996)); and lac operon elements, which are used in combination with a constitutively expressed lac repressor to confer, for example. IPTG-inducible expression (Wilde et al., *EMBO J.* 11:1251-1259 (1992)). An inducible regulatory element useful in the transgenic plants of the invention also can be, for example, a nitrate-inducible promoter derived from the spinach nitrite reductase gene (Back et al., *Plant Mol. Biol.* 17:9 (1991)) or a light-inducible promoter, such as that associated with the small subunit of RuBP carboxylase or the LHCP gene families (Feinbaum et al. *Mol. Gen. Genet.* 226:449 (1991); Lam and Chua, *Science* 248:471 (1990)).

Tissue-Specific Promoters

Alternatively, the plant promoter may direct expression of the mutated PYR/PYL polynucleotide in a specific tissue (tissue-specific promoters). Tissue specific promoters are transcriptional control elements that are only active in particular cells or tissues at specific times during plant development, such as in vegetative tissues or reproductive tissues.

Examples of tissue-specific promoters under developmental control include promoters that initiate transcription only (or primarily only) in certain tissues, such as vegetative tissues, e.g., roots or leaves, or reproductive tissues, such as fruit, ovules, seeds, pollen, pistols, flowers, or any embryonic tissue, or epidermis or mesophyll. Reproductive tissue-specific promoters may be, e.g., ovule-specific, embryo-specific, endosperm-specific, integument-specific, seed and seed coat-specific, pollen-specific, petal-specific, sepal-specific, or some combination thereof. In some embodiments, the promoter is cell-type specific, e.g., guard cell-specific.

Epidermal-specific promoters include, for example, the *Arabidopsis* LTP1 promoter (Thoma et al. (1994) *Plant Physiol.* 105(1):35-45), the CER1 promoter (Aarts et al. (1995) *Plant Cell* 7:2115-27), and the CER6 promoter (Hooker et al. (2002) *Plant Physiol* 129:1568-80), and the orthologous tomato LeCER6 (Vogg et al. (2004) *J. Exp Bot.* 55:1401-10).

Guard cell-specific promoters include, for example, the DGP1 promoter (Li et al (2005) *Science China C Life Sci.* 48:181-186).

Other tissue-specific promoters include seed promoters. Suitable seed-specific promoters are derived from the following genes: MAC1 from maize (Sheridan (1996) *Genetics* 142:1009-1020); Cat3 from maize (GenBank No. L05934, Abler (1993) *Plant Mol. Biol.* 22:10131-1038); vivparous-1 from *Arabidopsis* (Genbank No. U93215); atmyc1 from *Arabidopsis* (Urao (1996) *Plant Mol. Biol.* 32:571-57; Conceicao (1994) *Plant* 5:493-505); napA from *Brassica napus* (GenBank No. J02798, Josefsson (1987) JBL 26:12196-1301); and the napin gene family from *Brassica napus* (Sjodahl (1995) *Planta* 197:264-271).

A variety of promoters specifically active in vegetative tissues, such as leaves, stems, roots and tubers, can also be used to express polynucleotides encoding mutated PYR/PYL receptor polypeptides. For example, promoters controlling patatin, the major storage protein of the potato tuber, can be used, see, e.g., Kim (1994) *Plant Mol. Biol.* 26:603-615: Martin (1997) *Plant J.* 11:53-62. The ORF 13 promoter from *Agrobacterium rhizogenes* that exhibits high activity in roots can also be used (Hansen (1997) *Mol. Gen. Genet.* 254:337-343. Other useful vegetative tissue-specific promoters include: the tarin promoter of the gene encoding a globulin from a major taro (*Colocasia esculenta* L. Schott) corm protein family, tarin (Bezerra (1995) *Plant Mol. Biol.* 28:137-144): the curculin promoter active during taro corm development (de Castro (1992) *Plant Cell* 4:1549-1559) and the promoter for the tobacco root-specific gene TobRB7, whose expression is localized to root meristem and immature central cylinder regions (Yamamoto (1991) *Plant Cell* 3:371-382).

Leaf-specific promoters, such as the ribulose biphosphate carboxylase (RBCS) promoters, can also be used. For example, the tomato RBCS1, RBCS2 and RBCS3A genes are expressed in leaves and light-grown seedlings, only RBCS1 and RBCS2 are expressed in developing tomato fruits (Meier (1997) *FEBS Lett.* 415:91-95). A ribulose bisphosphate carboxylase promoters expressed almost exclusively in mesophyll cells in leaf blades and leaf sheaths at high levels, described by Matsuoka (1994) *Plant J.* 6:311-319, can be used. Another leaf-specific promoter is the light harvesting chlorophyll a/b binding protein gene promoter, see, e.g., Shiina (1997) *Plant Physiol.* 115:477-483; Casal (1998) *Plant Physiol.* 116:1533-1538. The *Arabidopsis thaliana* myb-related gene promoter (Atmyb5) described by Li (1996) *FEBSLett.* 379:117-121, is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16 cell stage of embryo development and persists beyond the heart stage. A leaf promoter identified in maize by Busk (1997) *Plant J.* 11:1285-1295, can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, described by Di Laurenzio (1996) *Cell* 86:423-433; and, Long (1996) *Nature* 379:66-69; can be used. Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto (1995) *Plant*

Cell. 7:517-527). Also useful are kn1-related genes from maize and other species which show meristem-specific expression, see, e.g., Granger (1996) *Plant Mol. Biol.* 31:373-378; Kerstetter (1994) *Plant Cell* 6:1877-1887; Hake (1995) *Philos. Trans. R. S c. Lond. B. Biol. Sci.* 350:45-51. For example, the *Arabidopsis thaliana* KNAT1 promoter (see, e.g., Lincoln (1994) *Plant Cell* 6:1859-1876).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, the mutated PYR/PYL polynucleotide is expressed through a transposable element. This allows for constitutive, yet periodic and infrequent expression of the constitutively active polypeptide. The invention also provides for use of tissue-specific promoters derived from viruses including, e.g., the tobamovirus subgenomic promoter (Kumagai (1995) *Proc. Natl. Acad. Sci. USA* 92:1679-1683; the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) *Plant Mol. Biol.* 31:1129-1139).

VI. Production of Plants Comprising PYR/PYL Hypersensitive Mutations

In another aspect, plants comprising a hypersensitive mutated PYR/PYL receptor polypeptide comprising one or more amino acid substitutions as described herein are provided. In some embodiments, the plant comprises an in situ mutated PYR/PYL receptor polypeptide comprising one or more amino acid substitutions as described herein. In some embodiments, the plant is a transgenic plant comprising a recombinant expression cassette for expressing the hypersensitive PYR/PYL receptor polypeptide in the plant. In some embodiments, a transgenic plant is generated that contains a complete or partial sequence of a polynucleotide that is derived from a species other than the species of the transgenic plant. It should be recognized that transgenic plants encompass the plant or plant cell in which the expression cassette is introduced as well as progeny of such plants or plant cells that contain the expression cassette, including the progeny that have the expression cassette stably integrated in a chromosome.

Transgenic Plants Comprising Recombinant Expression Cassettes

In some embodiments, a recombinant expression vector comprising a PYR/PYL coding sequence driven by a heterologous promoter may be introduced into the genome of the desired plant host by a variety of conventional techniques. For example, the DNA construct may be introduced directly into the genomic DNA of the plant cell using techniques such as electroporation and microinjection of plant cell protoplasts, or the DNA construct can be introduced directly to plant tissue using ballistic methods, such as DNA particle bombardment. Alternatively, the DNA construct may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. While transient expression of the constitutively active PYR/PYL receptor is encompassed by the invention, generally expression of construction of the invention will be from insertion of expression cassettes into the plant genome, e.g., such that at least some plant offspring also contain the integrated expression cassette.

Microinjection techniques are also useful for this purpose. These techniques are well known in the art and thoroughly described in the literature. The introduction of DNA constructs using polyethylene glycol precipitation is described in Paszkowski et al. *EMBO J.* 3:2717-2722 (1984). Electroporation techniques are described in Fromm et al. *Proc. Natl. Acad Sci.* USA 82:5824 (1985). Ballistic transformation techniques are described in Klein et al. *Nature* 327:70-73 (1987).

*Agrobacterium tumefaciens*-mediated transformation techniques, including disarming and use of binary vectors, are well described in the scientific literature. See, for example, Horsch et al. *Science* 233:496-498 (1984), and Fraley et al. *Proc. Natl. Acad. Sci.* USA 80:4803 (1983).

Transformed plant cells derived by any of the above transformation techniques can be cultured to regenerate a whole plant that possesses the transformed genotype and thus the desired phenotype such as enhanced abiotic stress resistance. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In Situ Alterations in Plants

Plant gene manipulations can be precisely tailored in non-transgenic organisms using the CRISPR/Cas9 genome editing method. In this bacterial antiviral and transcriptional regulatory system, a complex of two small RNAs—the CRISPR-RNA (crRNA) and the trans-activating crRNA (tracrRNA)—directs the nuclease (Cas9) to a specific DNA sequence complementary to the crRNA (Jinek et al., *Science*, 2012, 337:816-821). Binding of these RNAs to Cas9 involves specific sequences and secondary structures in the RNA. The two RNA components can be simplified into a single element, the single guide-RNA (sgRNA), which is transcribed from a cassette containing a target sequence defined by the user (Jinek et al., supra). This system has been used for genome editing in humans, zebrafish, *Drosophila*, mice, nematodes, bacteria, yeast, and plants (Hsu et al., *Cell*, 2014, 157:1262-1278). In this system the nuclease creates double stranded breaks at the target region programmed by the sgRNA. These can be repaired by non-homologous recombination, which often yields inactivating mutations. The breaks can also be repaired by homologous recombination, which enables the system to be used for gene targeted gene replacement (Li et al., *Nat. Biotechnol.*, 2013, 31:688-

691; Shan et al., *Nat. Biotechnol.*, 2013, 31:686-688). The hypersensitive mutations described in this application can be introduced into plants using the CAS9/CRISPR system.

Accordingly, in some embodiments, instead of generating a transgenic plant, a native PYR/PYR coding sequence in a plant or plant cell is altered in situ to generate a plant or plant cell carrying a polynucleotide encoding a hypersensitive PYR/PYL polypeptide as described herein. For example, in some embodiments, CRISPR technology is used to introduce one or more nucleotide changes into a PYR/PYL coding sequence in situ to change the appropriate codon to make a change corresponding to K63X, I82X, I84X, D1 54X, M158X, T162X, L166X, or K170X of SEQ ID NO:1 (where X is an amino acid described herein that confers hypersensitivity, e.g., as described in the Example section below). The CRISPR/Cas system has been modified for use in prokaryotic and eukaryotic systems for genome editing and transcriptional regulation. The "CRISPR/Cas" system refers to a widespread class of bacterial systems for defense against foreign nucleic acid. CRISPR/Cas systems are found in a wide range of eubacterial and archacal organisms. CRISPR/Cas systems include type I, II, and III sub-types. Wild-type type II CRISPR/Cas systems utilize the RNA-mediated nuclease, Cas9 in complex with guide and activating RNA to recognize and cleave foreign nucleic acid. Cas9 homologs are found in a wide variety of eubacteria, including, but not limited to bacteria of the following taxonomic groups: Actinobacteria, Aquificae, Bacteroidetes-Chlorobi, Chlamydiae-Verrucomicrobia, Chlroflexi, Cyanobacteria, Firmicutes, Proteobacteria, Spirochaetes, and Thermotogae. An exemplary Cas9 protein is the *Streptococcus pyogenes* Cas9 protein. Additional Cas9 proteins and homologs thereof are described in, e.g., Chylinksi et al., *RNA Biol.*, 2013, 10:726-737; Hou et al., *PNAS.* 2013, 110:15644-15649; Makarova et al., *Nat. Rev. Microbiol.*, 2011, 9: 467-477; Sampson et al., *Nature*, 2013, 497:254-257; and Jinek et al., *Science*, 2012, 337:816-21.

Accordingly, in one aspect, a method is provided of using CRISPR/CAS9 to introduce at least one of the mutation described herein into a plant cell is performed. In some embodiments, a method of altering a (e.g., native) nucleic acid encoding PYR/PYL polypeptide in a plant is provided. In some embodiments, the method comprises introducing into the plant cell containing and expressing a DNA molecule having a target nucleic acid encoding PYR/PYL polypeptide an engineered, non-naturally occurring Clustered Regularly Interspaced Short Palindromic Repeats (CRISPR)-CRISPR associated (Cas) (CRISPR-Cas) system. In some embodiments, the CRISPR-Cas system comprises one or more vectors comprising: (a) a first regulatory element operable in a plant cell operably linked to at least one nucleotide sequence encoding a CRISPR-Cas system guide RNA that hybridizes with the target sequence, and (b) a second regulatory element operable in a plant cell operably linked to a nucleotide sequence encoding a Type-II Cas9 protein, wherein components (a) and (b) are located on the same or different vectors of the system, whereby the guide RNA targets the target sequence and the Cas9 protein cleaves the DNA molecule, whereby at least one of the hypersensitive mutations described herein is introduced into the target nucleic acid encoding the PYR/PYL polypeptide. In some embodiments, the PRY/PYL polypeptide is selected from any of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, or 89 or a substantially identical polypeptide. In some embodiments, the hypersensitive mutation introduced to the target nucleic acid is (corresponding to their position in *Arabidopsis* PYR1 (SEQ ID NO:1)): K63, I82, I84, D154, M158, T162, L166, K170, or a combination thereof. In some embodiments, the hypersensitive mutation introduced to the target nucleic acid is (corresponding to their position in *Arabidopsis* PYR1 (SEQ ID NO:1)): K63D/E/Q, I82A/F/K/S, I84A/D/N/R/S/T, D154E/F/G/H/K/M/Q/R/W/Y M158A/D/G/H/N/W, T162H/K/L/MA/W/Y, L166A/E/G/H/K/MIN/P/Q/R/S/T/W, K170A/C/D/E/F/G/H/I/M/N/Q/R/S/T/V/Y, or a combination thereof. In some embodiments, no other mutations are introduced into the target nucleic acid.

Also provided herein are plants or plant cells resulting from the above-described method. Such a plant will contain a non-naturally-occurring nucleic acid sequence encoding the hypersensitive PYR/PYL polypeptide.

Plant Characteristics

The expression cassettes or in situ alterations described herein can be used to confer abiotic stress resistance on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna*, and, *Zea*. In some embodiments, the plant is selected from the group consisting of rice, maize, wheat, soybeans, cotton, canola, turfgrass, and alfalfa. In some embodiments, the plant is an ornamental plant. In some embodiment, the plant is a vegetable- or fruit-producing plant.

Those of skill will recognize that a number of plant species can be used as models to predict the phenotypic effects of transgene expression in other plants. For example, it is well recognized that both tobacco (*Nicotiana*) and *Arabidopsis* plants are useful models of transgene expression, particularly in other dicots.

In some embodiments, the plants of the invention have enhanced ABA-mediated phenotypes, for example enhanced seed dormancy, as compared to plants that are otherwise identical except for expression of the hypersensitive PYR/PYL receptor polypeptide. Those of skill in the art will recognize that ABA is a well-studied plant hormone and that ABA mediates many changes in characteristics, any of which can be monitored to determine changes in phenotype. In some embodiments, an enhanced ABA-mediated phenotype is manifested by altered timing of seed germination or altered stress (e.g., drought, freezing cold, and/or salt) tolerance.

Abiotic stress resistance can be assayed according to any of a number of well-known techniques. For example, for drought tolerance, plants can be grown under conditions in which less than optimum water is provided to the plant. Drought resistance can be determined by any of a number of standard measures including turgor pressure, growth, yield, and the like. In some embodiments, a transgenic plant expressing a mutated PYR/PYL receptor as described herein has enhanced drought tolerance if the loss of turgor in the transgenic plant is reduced by at least about 10%, 15%, 20%, 25%, 30%, 40%, 50%, 60%, 70%, 80%, 90%, or more as compared to a non-transgenic control plant over a defined period of time (e.g., over the course of 5, 6, 7, 8, 9, 10, 11, 12, 13, 14 days or more, e.g., 3, 4, 5 weeks or more).

In some embodiments, the enhanced ABA-mediated phenotype is enhanced tolerance to moderate or high salinity. Salinity tolerance can be determined by any of a number of standard measures, including germination, growth, yield, or plant survival, leaf injury, premature loss of chlorophyll, and the like. In some embodiments, transgenic plants expressing a mutated PYR/PYL receptor as described herein have enhanced salt tolerance if the survival of the transgenic plants under moderate-salt or high-salt conditions (e.g. about 50 mM, 100 mM, 150 mM, 200 mM, 250 mM, 300 mM NaCl or higher) is increased by at least about 10%, 15%, 20%, 25%, 30%, 40%, 50%, 60%, 70%, 80%, 90%, or more as compared to a non-transgenic control plant over a defined period of time (e.g., over the course of 5, 6, 7, 8, 9, 10, 11, 12, 13, 14 days or more, e.g., 3, 4, 5 weeks or more).

VII. PYR/PYL Fusion Proteins and Genome Editing

In some embodiments, the hypersensitive PYR/PYL polypeptides described herein are provided as fusion proteins, i.e., translational fusions with one or more fusion partner. In some embodiments, a hypersensitive PYR/PYL polypeptide is fused with a transcriptional activation or modulation domain. A non-limiting example of such a domain is VP16 or VP64. The fusion proteins can further comprise a nuclear localization signal sequence such that the fusion protein, when translated in a eukaryotic host cell, is localized to the cell nucleus. Also provided are polynucleotides encoding such fusion proteins as well as host cells comprising and expressing such polynucleotides. The polynucleotides in such instances will be heterologous to the host cell, i.e., will not be naturally occurring, for example transformed into the cell.

Such fusion proteins are useful, for example, in controlling eukaryotic gene expression in the cell when co-expressed with a sequence-specific DNA binding domain fused with ABI1 ("ABA Insensitive 1") or other proteins having specific binding affinity for PYR/PYL proteins binding ABA. Exemplary sequence-specific DNA binding domains include, but are not limited to zinc-finger proteins, TALENS, transcription factor DNA binding domains, and RNA-guided DNA-binding domains of inactive Cas9 (dCas9). When both fusion proteins are co-expressed in the cell in the presence of ABA, the two fusion proteins will co-localized due to the binding of ABA1 to the ABA-binding PYR/PYL protein, thereby bringing the transcriptional activation or modulation domain in proximity to the target promoter, thereby regulating gene expression. Examples of systems and their use in gene regulation, are described in, e.g., Konermann et al., *Nature*, 2013, 500:472-476; Xing et al., *BMC Plant Biology*, 2014, 14:327; Liang et al., *J Genet Genomics*, 2014, 41:63-68; and Bortesi et al., *Biotechnology Advances*, 2015, 33:41-52.

RNA Directed Genome Modification

In one aspect, provided herein is a method for introducing a mutation in sin at a PYR/PYL mutation target site as described herein in a plant cell genome. For example, in some embodiments, the PYR/PYL mutation target site comprises a nucleic acid that encodes a mutation corresponding to K63D/E/Q, I82A/F/K/S, I84A/D/N/R/S/T, D154E/F/G/H/K/M/Q/R/W/Y M158A/D/G/H/N/W, T162H/K/L/M/W/Y, L166A/E/G/H/K/M/N/P/Q/R/ST/W, or K170A/C/D/E/F/G/H/I/M/N/Q/R/S/T/V/Y in SEQ ID NO:1. In certain embodiments the method comprises introducing into the plant cell: (1) a CRISPR ribonucleic acid (crRNA); (2) a transacting ribonucleic acid (tracRNA); (3) a nuclease (e.g., Cas9); and (4) a repair nucleic acid that can undergo homologous recombination that contains the mutation. In such methods, the crRNA and tracRNA directs the nuclease to the PYR/PYL mutation target site in a plant cell genome. Upon its recruitment, the nuclease (e.g., Cas9) creates a double strand break at the PYR/PYL mutation target site. The double strand break at the PYR/PYL mutation target site facilitates homologous recombination of the repair nucleic acid containing the mutation with a region of the plant cell genome that includes the PYR/PYL mutation target site, thereby introducing the mutation at the PYR/PYL mutation target site. The components of such methods are described, e.g., in Sander et al., *Nat Biotechnol.*, 2014, 32:347-355.

Mutations can be introduced into any suitable plant cell using the subject method. In some embodiments, the plant cell is a plant embryo. In certain embodiments, the plant cell is a maize plant cell.

Each component of the method can be introduced into the plant cell using any suitable method known in the art. In certain embodiments, the crRNA and tracRNA are introduced into the cell as an expression cassette containing a polynucleotide (i.e., DNA) encoding the crRNA and/or traRNA. In some embodiments, the expression cassette includes an RNA polymerase promoter operably linked to the polynucleotide encoding the crRNA and/or traRNA, thereby allowing transcription of the crRNA and/or traRNA. In some embodiments, the Cas9 is introduced into the cell as an expression vector containing a promoter operably linked to a polynucleotide encoding Cas9. Any suitable promoter can be used, including but not limited to, the promoters described herein (e.g., constitutive promoters, inducible promoters, or tissue-specific promoters as described in Section V above). In certain embodiments, the promoter is a ubiquitin-1 promoter (e.g., prUbi-10). The DNA construct (e.g., the expression cassettes and vectors described herein) can be introduced directly to plant tissue, for example, using ballistic methods, such as DNA particle bombardment.

Each of the crRNA, tracRNA, and nuclease can be introduced separately or together as part of one expression vector into the cell of interest (e.g., a maize plant cell). In certain embodiments, the crRNA and the tracRNA are fused together to create a guide ribonucleic acid (gRNA). In some embodiments, the gRNA includes, from 5' to 3', a crNA linked to a tracRNA. In certain embodiments the crRNA, tracRNA, and nuclease (e.g., Cas9) are introduced together as nucleic acid cassettes included in one expression vector.

In some embodiments, the method further includes the step of selecting plant cells having the mutation. Selecting for a mutation can be performed by any useful technique known in the art, including, but not limited PCR amplification followed by sequencing, capillary electrophoresis and Nuclease Serveyer assay. In some embodiments, the method is for the production of a maize plant.

Promoter Editing

In another aspect, a hypersensitive PYR/PYL polypeptide as described herein is overexpressed in a plant by promoter editing. In promoter editing, homologous recombination in the promoter region of a gene (e.g., in the promoter region of a gene encoding a wild-type PYR/PYL protein or a gene encoding a hypersensitive mutated PYR/PYL protein as described herein) is used to replace the native promoter with a heterologous promoter. Methods of replacing a native promoter with a heterologous promoter by homologous recombination are described in Shi et al., *Plant Biotechnology J.*, 2016, doi:10.1111/pbi.12603, incorporated by reference herein.

In some embodiments, the heterologous promoter that is inserted is a promoter as described in Section V above (e.g., a constitutively active promoter or an inducible promoter). In some embodiments, the heterologous promoter is a constitutively active promoter, e.g., as described in Section V above. In some embodiments, the promoter is an actin promoter. In some embodiments, the promoter is a ubiquitin promoter. In some embodiments, the promoter is a promoter described in Shi et al., *Plant Biotechnology J.*, 2016, doi: 10.1111/pbi.12603.

VIII. Examples

The following examples are offered to illustrate, but not to limit, the claimed invention.

Example 1: Identification of Hypersensitive Mutations in Receptor-PP2C Interface This example describes the identification of mutations located in receptor-PP2C interface residues that lower the concentration of ABA required to activate the ABA receptor PYR1. The mutations disclosed reside in highly conserved residues near the receptor-PP2C binding interface and can be transplanted onto other PYR/PYL receptors. A mutant receptor with increased sensitivity for a ligand (e.g., ABA) can in some cases elicit greater biological effect, relative to a wild-type receptor, when both are activated under identical conditions by the same concentration of activating ligand. Thus, mutations that make a receptor hypersensitive to a ligand can be useful for engineering organisms that elicit stronger responses to the ligand relative to the wild-type receptor. Additionally, ABA hypersensitive plants possess enhanced ABA responses and improved drought tolerance (Wang et al., *Plant J.*, 2005, 43:413-424).

Based on these considerations, we set out to systematically establish specific ABA receptor mutations that increase ABA responsiveness. This was done by testing a collection of PYR1 variants with all possible single amino acid substitution mutations in receptor-PP2C interface residues. Thus we conducted site-saturated mutagenesis of receptor-PP2C interface residues, which we define as those that are within 5 Å of a PP2C residue in available X-ray coordinates. This collection of mutants was constructed previously, as described in WO 2013/006263 and Mosquna et al., *Proc Nad Acad Sci USA* 108: 20838-20843 (2011). This collection of mutants was made by mutagenizing a previously described pBD GAL-PYR1 template (Park, S.-Y., et al. *Science* 324, 1068-1071 (2011)). In response to ABA, this particular plasmid encodes a fusion protein that binds to a co-expressed GAL4 activation domain-HAB1 fusion protein, encoded by the plasmid pACT-HAB1. This binding reconstitutes a functional GAL4 transcriptional activator and subsequent transcription of a β-galactosidase reporter gene, which in turn enables colorimetric based detection of agonist promoted receptor-PP2C interaction when lysed cells are exposed to the substrate X-gal. The mutant clones were individually transformed into *S. cerevisiae* strain Y 190 containing pACT-HAB1. Yeast transformants were selected for the presence of plasmids on synthetic dextrose (SD) agar plates lacking Leu and Trp (SD-LT) and examined for PP2C interactions by using X-gal staining to monitor β-gal reporter gene expression levels. Individual clones were arrayed into 96 well plates and then spotted onto SD-LT lawn (i.e. one-well) plates containing 0, 0.5 or 5.0 µM (+)-ABA. Each assay plate contained 95 mutant clones and one wild type PYR1 positive control clone. The spotted cells were cultured at 30° C. for 48 hours after which they were lysed by chloroform and stained with an X-gal solution, as previously described (Park, S.-Y., et al. (2009) *Science* 324, 1068-1071). Positive were defined as those mutants that displayed staining on 0.5 µM (+)-ABA but no staining on plates lacking (+)-ABA. After this initial screening exercise, all positives clones were retested on plates containing 0, 0.25, 0.5 and 1 µM (+)-ABA and stained for galactosidase activity as described above. Mutant clones showing detectable staining on 0.5 µM (+)-ABA or lower were scored as hypersensitive mutants.

Figure 1B:
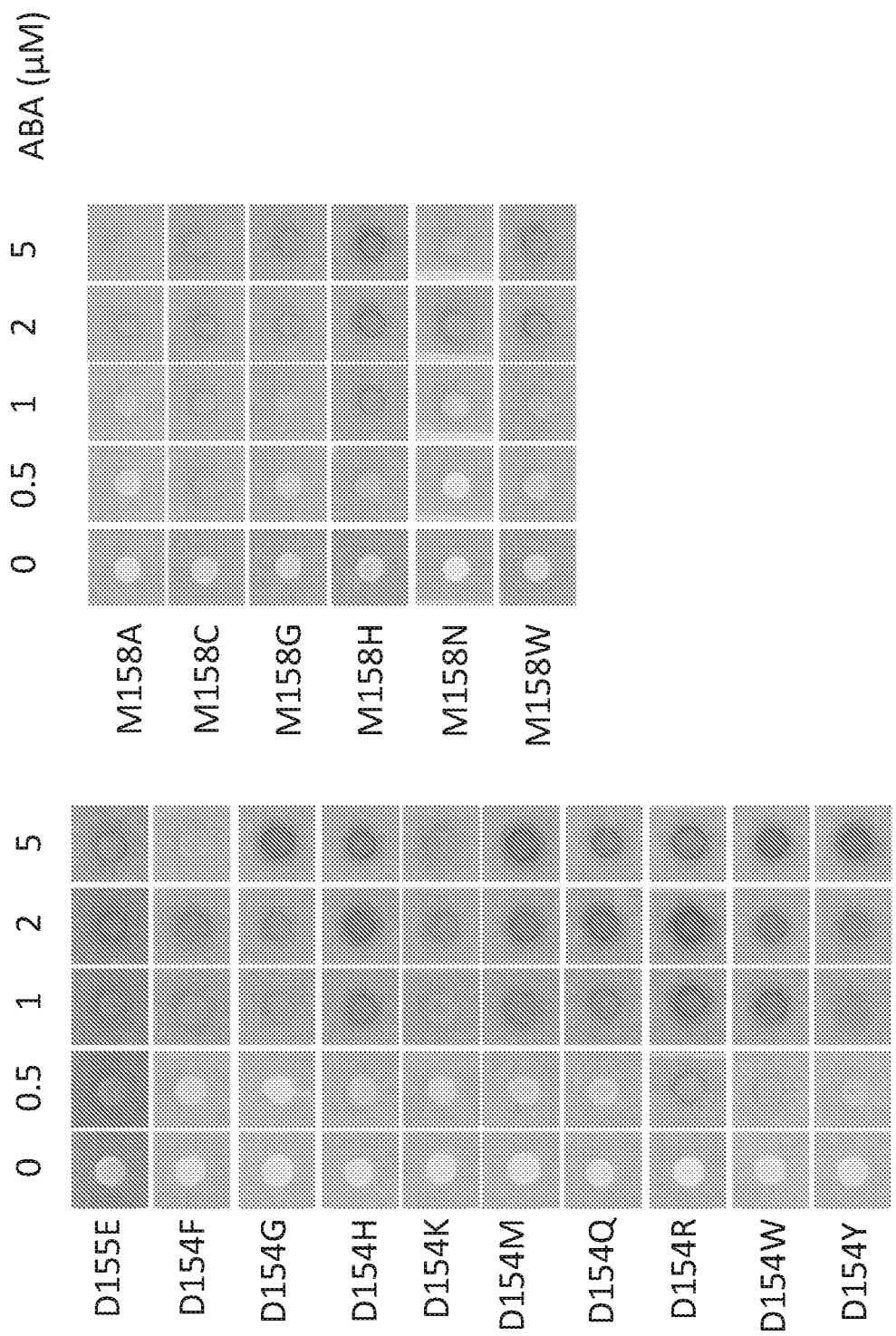
Figure 1D:
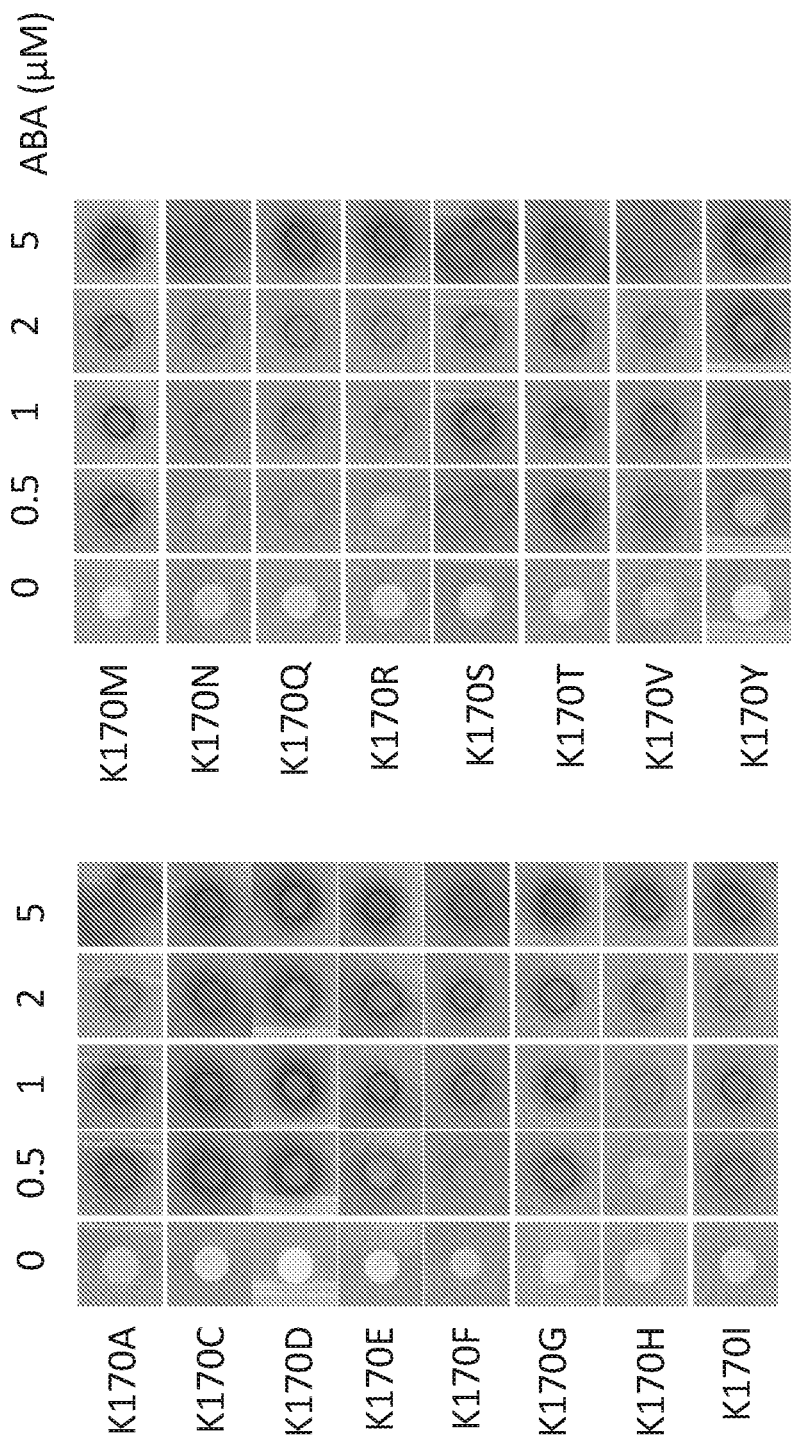

FIG. 1 depicts the results of PYR1 mutant—HAB1 interactions as assayed in a yeast two-hybrid assay under different ABA concentrations, with darker spots indicating increased interaction. This data is also summarized in Table 1 below.

TABLE 1

Mutation sites and strength of hypersensitivity mutations identified

| Residue | Hypersensitivity Mutations Identified | Strength of Hypersensitivity Mutations | | |
|---|---|---|---|---|
| | | +++ | ++ | + |
| K63 | D, E, Q | | Q | D, E |
| I82 | A, F, K, S | | A, F, S | K |
| I84 | A, D, N, R, S, T | | A, D, N, R, S, T | |
| D154 | E, F, G, H, K, M, Q, R, W, Y | | E, H, K, M, Q, R, W, Y | F, G |
| M158 | A, D, G, H, I, N, S, V, W | I | D, G, H, S, V, W | A, N |
| T162 | H, K, L, M, W, Y | Y | H, L, M, W | K |
| L166 | A, E, F, G, H, K, M, N, P, Q, R, S, T, W, Y | F, G, H, K, N, Q, R, S, T, Y | A, E, M, W | P |
| K170 | A, C, D, E, F, G, H, I, M, N, Q, R, S, T, V, Y | A, C, D, E, F, G, I, M, S, T, V, Y | H, N, Q, R | |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

INFORMAL SEQUENCE LISTING

SEQ ID NO: 1 (PYR1)
MPSELTPEERSELKNSIAEFHTYQLDPGSCSSLHAQRIHAPPELVWSIVRRFDKPQTYK
HFIKSCSVEQNFEMRVGCTRDVIVISGLPANTSTERLDILDDERRVTGFSIIGGEHRLT
NYKSVTTVHRFEKENRIWTVVLESYVVDMPEGNSEDDTRMFADTVVKLNLQKLAT
VAEAMARNSGDGSGSQVT

INFORMAL SEQUENCE LISTING

SEQ ID NO: 2 (PYL1)
MANSESSSSPVNEEENSQRISTLHHQTMPSDLTQDEFTQLSQSIAEFHTYQLGNGRCS
SLLAQRIHAPPETVWSVVRRFDRPQIYKHFIKSCNVSEDFEMRVGCTRDVNVISGLPA
NTSRERLDLLDDDRRVTGFSITGGEHRLRNYKSVTTVHRFEKEEEEERIWTVVLESY
VVDVPEGNSEEDTRLFADTVIRLNLQKLASITEAMNRNNNNNNSSQVR

SEQ ID NO: 3 (PYL2)
MSSSPAVKGLTDEEQKTLEPVIKTYHQFEPDPTTCTSLITQRIHAPASVVWPLIRRFDN
PERYKHFVKRCRLISGDGDVGSVREVTVISGLPASTSTERLEFVDDDHRVLSFRVVGG
EHRLKNYKSVTSVNEFLKQDSGKVYTVVLESYTVDIPEGNTEEDTKMFVDTVVKLN
LQKLGVAATSAPMHDDE

SEQ ID NO: 4 (PYL3)
MNLAPIHDPSSSSTTTTSSSTPYGLTKDEFSTLDSIIRTHHTFPRSPNTCTSLIAHRVDAP
AHAIWRFVRDFANPNKYKHFIKSCTIRVNGNGIKEIKVGTIREVSVVSGLPASTSVEIL
EVLDEEKRILSFRVLGGEHRLNNYRSVTSVNEFVVLEKDKKKRVYSVVLESYIVDIPQ
GNTEEDTRMFVDTVVKSNLQNLAVISTASPT

SEQ ID NO: 5 (PYL4)
MLAVHRPSSAVSDGDSVQIPMMIASFQKRFPSLSRDSTAARFHTHEVGPNQCCSAVI
QEISAPISTVWSVVRRFDNPQAYKHFLKSCSVIGGDGDNVGSLRQVHVVSGLPAASS
TERLDILDDERHVISFSVVGGDHRLSKYRSVTTLHPSPISGTVVVESYVVDVPPGNTK
EETCDFVDVIVRCNLQSLAKIAENTAAESKKKMSL

SEQ ID NO: 6 (PYL5)
MRSPVQLQHGSDATNGFHTLQPHDQTDGPIKRVCLTRGMHVPEHVAMHHTHDVGP
DQCCSSVVQMIHAPPESVWALVRRFDNPKVYKNFIRQCRIVQGDGLHVGDLREVMV
VSGLPAVSSTERLEILDEERHVISFSVVGGDHRLKNYRSVTTLHASDDEGTVVVESYI
VDVPPGNTEEETLSFVDTIVRCNLQSLARSTNRQ

SEQ ID NO: 7 (PYL6)
MPTSIQFQRSSTAAEAANATVRNYPHHHQKQVQKVSLTRGMADVPEHVELSHTHVV
GPSQCFSVVVQDVEAPVSTVWSILSRPFEHPQAYKHFVKSCHVVIGDGREVGSVREVR
VVSGLPAAFSLERLEIMDDDRHVISFSVVGGDHRLMNYKSVTTVHESEEDSDGKKRT
RVVESYVVDVPAGNDKEETCSFADTIVRCNLQSLAKLAENTSKFS

SEQ ID NO: 8 (PYL7)
MEMIGGDDTDTEMYGALVTAQSLRLRHLHHCRENQCTSVLVKYIQAPVHLVWSLV
RRFDQPQKYKPFISRCTVNGDPEIGCLREVNVKSGLPATTSTERLEQLDDEEHILGINII
GGDHRLKNYSSILTVHPEMIDGRSGTMVMESFVVDVPQGNTKDDTCYFVESLIKCNL
KSLACVSERLAAQDITNSIATFCNASNGYREKNHTETNL

SEQ ID NO: 9 (PYL8)
MEANGIENLTNPNQEREFIRRHHKIIELVDNQCSSTLVKHINAPVHIVWSLVRRFDQP
QKYKPFISRCVVKGNMEIGTVREVDVKSGLPATRSTERLELLDDNEHILSIRIVGGDH
RLKNYSSIISLHPETIEGRIGTLVIESFVVDVPEGNTKDETCYFVEALIKCNLKSLADISE
RLAVQDTTESRV

SEQ ID NO: 10 (PYL9)
MMDGVEGGTAMYGGLETVQYVRTHHQHLCRENQCTSALVKHIKAPLHLVWSLVR
RFDQPQKYKPFVSRCTVIGDPEIGSLREVNVKSGLPATTSTERLELLDDEEHILGIKIIG
GDHRLKNYSSILTVHPEIIEGRAGTMVIESFVVDVPQGNTKDETCYFVEAL1RCNLKS
LADVSERLASQDITQ

SEQ ID NO: 11 (PYL10)
MNGDETKKVESEYIKKHHRHELVESQCSSTLVKHIKAPLFILVWSIVRRFDEPQKYKP
FISRCVVQGKKLEVGSVREVDLKSGLPATKSTEVLEILDDNEHILGIRIVGGDHRLKN
YSSTISLHSETIDGKTGTLAIESFVVDVPEGNTKEETCFFVEALIQCNLNSLADVTERL
QAESMEKKI

SEQ ID NO: 12 (PYL11)
METSQKYHTCGSTLVQTIDAPLSLVWSILRRFDNPQAYKQFVKTCNLSSGDGGEGSV
REVTVVSGLPAEFSRERLDELDDESHVMMISIIGGDHRLVNYRSKTMAFVAADTEEK.
TVVVESYVVDVPEGNSEEETTSFADTIVGFNLKSLAKLSERVAHLKL

SEQ ID NO: 13 (PYL12)
MKTSQEQHVCGSTVVQTINAPLPLVWSILRRFDNPKTFKHFVKTCKLRSGDGGEGSV
REVTVVSDLPASFSLERLDELDDESHVMVISIIGGDHRLVNYQSKTTVFVAAEEEKTV
VVESYVVDVPEGNTEEETTLFADTIVGCNLRSLAKLSEKMMELT

SEQ ID NO: 14 (PYL13)
MESSKQKRCRSSWETIEAPLPLVWSILRSFDKPQAYQRFVKSCTMRSGGGGGKGGE
GKGSVRDVTLVSGFPADFSTERLEELDDESHVMVVSIIGGNHRLVNYKSKTKVVASP
EDMAKKTVWESYVVDVPEGTSEEDTEFFVDNIIRYNLTSLAKLTKKMMK

INFORMAL SEQUENCE LISTING

SEQ ID NO: 15
*Brassica_oleracea* {89257688}
gb|ABD65175.1|
mpsqltpeerselaqsiaefhtyhlgpgscsslhaqrihappeivwsvvrrfdkpqtykhfikscsvedgfemrvgctravnvisgl
pantsterldildderrvtgfsiiggehrltnyksvttvhrfekerriwtvvlesywdmpegnseddtrmfadtvvklnlqklatvte
amarnagdgsgaqvt SEQ ID NO: 16
*Brassica_oleracea* {89274227}
gb|ABD65631.1|
mpseltqeerskltqsisefhtyhlgpgscsslhaqrihappeivwsvvrqfdkpqtykhfikscsveegfemrvgctrdvivisgl
pantsterldmldderrvtgfsiiggehrlknyksvttvhrfererriwtvvlesyvvdmpegnseddtrmfadtwklnlqklatvt
eamamagdgrgsrettcresfhlitafekqrqiteptvyqnppyhtgmtpeprtstvfieledhrtlpgnltptteehlqrmyqrfwg
irqlqrprqsfgerqsi SEQ ID NO: 17
*Vitis_vinifera* {157341954}
emb|CAO63410.1|
mqmkylegkqnlmeekgekqcipmdlavreaqfkgslldritwleqrlhklslqletrskqqphpsrmqtagetssrhgpkkel
scsfpvfstrnhnhghkqtsqfhvprfeyqeggrenpavvitkltpfhhpkiitilfpisnyfiiffflтfdtkkqypllfpilpsrflpish
litqeiekyktsshfsspaslfaamnkaetssmaeaesedsetttptthhltippgltqpefqelahsisefhtyqvgpgqcssllaqrv
haplptvwsvvrrfdkpqtykhfikschvedgfemrvgclrdvnvisglpaetsterldildderhvtgfsiiggehrlmyrsvttnh
ggeiwtwlesywdmpegnteedtrlfadtvvklnlqklasvtevsqscnypcqfhiienediqpeemnlgvlttsieeqrkkkr
vvamkdgstss SEQ ID NO: 18
*Vitis_vinifera* {147789129}
emb|CAN64657.1|
maeaesedsetttptthhltippgltqpefqelahsisefhtyqvgpgqcssllaqrvhaplptvwswrrfdkpqtykhfikschve
dgfemrvgclrdvnvisglpaetsterldiidderhvtgfsiiggehrlmyrsvttheyqnhggeiwtvvlesyvvdmpegntee
dtrlfadtwklnlseaxrr SEQ ID NO: 19
*Medicago_truncatula* {217073334}
gb|ACJ85026.1|
mekaesstastsdqdsdenhrtqhhltlpsglrqhefdslipfinshhtyligpnqcstllaqrihappqtvwswrsfdkpqiykhii
kscslkegfqmkvgctrdvnvisglpaatsterldvldderrvtgfsiiggehrlknyrsvtsvhgfgdgdnggeiwtwlesyvvd
vpegnteedtrlfadtwklnlqklasvtegknrdgdgksh SEQ ID NO: 20
*Oryza_sativa_Japonica*_Group {115483600}
ref|NP_001065470.1|
meqqeevppppaglgltaeeyaqvratveahhryavgpgqcssllaqrihappaavwavvrrfdcpqvykhfirscvlrpdphh
ddngndlrpgrlrevsvisglpaststerldllddahrvfgftitggehrlmyrsvttvsqldeictlvlesyivdvpdgnteddtrlfadt
virlnlqklksvseananaaaaaapppppaaae SEQ ID NO: 21
*Zea_mays* {195641068}
gb|ACG40002.1|
mdqqgaggdaevpaglgltaaeyeqlrstvdahhryavgegqcssllaqrihappeavwavvrrfdcpqvykhfirscalrpdp
eagdalcpgrlrevsvisglpaststerldllddaarvfgfsitggehrlrnyrsvttvselavpaictvvlesyvvdvpdgnteddtrlf
adtvirlnlqklksvaeanaaeaaattnsvllprpae SEQ ID NO: 22
*Zea_mays* {195625286}
gb|ACG34473.1|
mdqqgaggdaxvpaglgltaaeyeqlrstvdahhryavgegqcssllaqrihappeavwavvrrfdcpqvykhfirscalrpdp
eagdalcpgrlrevsvisglpaststerldllddaarvfgfsitggehrlmyrsvttvseladpaictvvlesyvvdvpdgnteddtrlf
adtvirlnlqklksvteanaaeaaattnsvllprpae SEQ ID NO: 23
*Vitis_vinifera* {157339249}
emb|CAO43790.1|
mdphhhhgltеееfralepiiqnyhtfepspntctslitqkidapaqvvwpfvrsfenpqkykhfikdctmrgdggvgsirevtw
sglpaststerleilddekhilsfrvvggehrlnnyrsvtsvndfskegkdytivlesyivdipegntgedtkmfvdtvvklnlqklav
vaitslheneeiadnegpsreislqsetesaergderrdgdgpskacnmewhcttke SEQ ID NO: 24
*Oryza_sativa_Japonica*_Group {49388537}
dbj|BAD25659.1|
mephmeralreavaseaerrelegvvrahhtfpaaeraagpgrrptctslvaqrvdaplaavwpivrgfanpqrykhfikscelaa
gdgatvgsvrevavvsglpaststerleildddrhvlsfrvvggdhrlnyrsvtsvtefsspssppтрусvvvesyvvdvpegnte
edtrmftdtvvklnlqklaavatsssppaagnhh

INFORMAL SEQUENCE LISTING

SEQ ID NO: 25
*Oryza_sativa*_Indica_Group {125538682}
gb|EAY85077.1|
mephmeralreavaseaerrelegvvrahhtfpaaeraagpgrrptctslvaqrvdaplaavwpivrgfanpqrykhfikscelaa
gdgatvgsvrevavvsglpaststerleildddrhvlsfrwggdhrlmyrsvtsvtefsspssppspprpycvvvesyvvdvpeg
nteedtrmftdtvvklnlqklaavatsssppaagnhh SEQ ID NO: 26
*Zea_mays* {194695858}
gb|ACF82013.1|
mpytaprpspqqhsrvlsgggakaashgascaavpaevarhhehaaragqccsavvqaiaapvgavwsvvrrfdrpqaykhfi
rscrlvgggdvavgsvrevrvvsglpatssrerleildderrvlsfrvvggehrlanyrsvttvheagagagtgtvvvesyvvdvph
gntadetrvfvdtivrcnlqslartaerla SEQ ID NO: 27
*Vitis_vinifera* {157355387}
emb|CA048777.1|
mpsnppksslvvhrinspnsittattasaaannhntstmpphkqvpdavsrhhthvvgpnqccsavvqqiaapvstvwsvvrrf
dnpqaykhfvkschvwgdgdvgtlrevhvisglpaanstereildderhvlsfsviggdhrlsnyrsvttlhpspsstgtvvlesy
vvdippgntkedtcvfvdtivrcnlqslaqiaenaagckrsss SEQ ID NO: 28
*Nicotiana_tabacum* {62867576}
emb|CAf84653.1|
mppsspdssvllqrissnttpdfackqsqqlqrrtmpipcttqvpdsvvrfhthpvgpnqccsaviqrisapvstvwsvvrrfdnp
qaykhfvkschvivgdgdvgtlrevrvisglpaasstereildderhvisfsvvggdhrlanyrsvttlhpepsgdgttivvesyvv
dvppgntrdetcvfvdtivkcnltslsqiavnvnrrkds SEQ ID NO: 29
*Oryza_sativa*_Indica_Group {125528236}
gb|EAY76350.1|
mpyaavrpspppqlsrpigsgagggkacpavpcevaryhehavgagqccstvvqaiaapadavwsvvrrfdrpqaykkfiks
crlvdgdggevgsvrevrvvsglpatssrerlevldddrrvlsfrivggehrlanyrsvttvheaaapamavvvesyvvdvppgnt
weetrvfvdtivrcnlqslartverlapeaprangsidha SEQ ID NO: 30
*Oryza_sativa*_Japonica_Group {15624049}
dbj|DAB68102.1|
mpyaavrpspppqlsrpigsgagggkacpavpcevaryhehavgagqcfstvvqaiaapadavwsvvrrfdrpqaykkfiksc
rlvdgdggevgsvrevrvvsglpatssrerlevldddrrvlsfrivggehrlanyrsvttvheaaapamavwesyvvdvppgnt
weetrvfvdtivrcnlqslartverlapeaprangsidha SEQ ID NO: 31
*Picea_sitchensis* {116783434}
gb|ABK22940.1|
mdiiagfdqlsfrlsgaskqitktgavqylkgeegygewlkevmgryhyhshdgarecrcssvvvqqveapvsvvwslvrrfd
qpqvykhfvsncfmrgdlkvgclrevrvvsglpaatsterldildeerhilsfsivggdhrlnnyrsittlhetlingkpgtiviesyvl
dvphgntkeetclfvdtivkcnlqslahvsnhlnsthrcl SEQ ID NO: 32
*Oryza_sativa*_Japonica_Group {115468550}
ref|NP_001037874.1|
meahveralregltegeeraalepavmahhtfppstttattaaatctslvtqrvaapvravwpivrsfgnpqrykhfvrtcalaagdga
svgsvrevtvvsglpaststerlemldddrhiisfrvvggqhrlrnyrsvtsvtefqppaagpgpappycvvvesyvvdvpdgnta
edtrmftdtvvklnlqmlaavaedsssasrrrd SEQ ID NO: 33
*Oryza_sativa*_Japonica_Group {115464439}
ref|NP_001055819.1|
mpytaprpsppqhsriggcggggvlkaagaaghaascvavpaevarhhehaagvgqccsavvqaiaapvdavwsvvrrfdrp
qaykhfirscrlldgdgdggavavgsvrevrvvsglpatssrerleildderrvlsfrwggehrlsnyrsvttvhetaagaaaavvve
syvvdvphgntadetrmfvdtivrcnlqslartaeqlalaapraa SEQ ID NO: 34
*Vitis_vinifera* {157351249}
emb|CA041436.1|
mpsslqlhrinnidpttvavaataavnchkqsrtplrcatpvpdavasyhahavgphqccsmvvqttaaalptvwsvvrrfdnpq
aykhflkschvifgdgdigtlrevhvvsglpaessterleildderhvlsfsvvggdhrlcnyrsvttlhpsptgtgtvvvesyvvdip
pgntkedtcvfvdtivkcnlqslaqmsekltnnnmss SEQ ID NO: 35
*Zea_mays* {195617008}
gb|ACG30334.1|
mpclqasspgsmpyqhhgrgvgcaaeagaavgasagtgtrcgahdgevpaeaarhhehaapgpgrccsavvqrvaapaeav
wsvvrrfdqpqaykrfvrscallagdggvgtlrevrvvsglpaasstereievldesheevlsfrvvggehrlqnylsvttvhpspaap
daatvwesyvvdvppgntpedtrvfvdtivkcnlqslattaeklalaav

| INFORMAL SEQUENCE LISTING |
|---|

SEQ ID NO: 36
*Physcomitrella_patens_subsp._patens* {168051209}
ref|XP_001778048.1|
mqtkgrqadfqtllegqqdlicrflirhelqphqcgsillqlikapvetvwsvarsfdkpqvykrfiqtceiiegdggvgsirevrlvss
ipatssierleilddeehiisfrvlggghrlqnywsvtslhsheidgqmgtlvlesyvvdipegntreethmfvdtvvrcnlkalaqvs
e SEQ ID NO: 37
*Oryza_sativa_Indica_Group* {125543492}
gb|EAY89631.1|
mpcipassspgiphqhqhqhhralagvgmavgcaaeaavaaagvagtrcgahdgevpmevarhhehaepgsgrccsavvqh
vaapapavvwswrrfdqpqaykrfvrscallagdggvgtlrevrwsglpaassrerleilddeshvlsfrvvggehrlknylsvttv
hpspsaptaatvvvesyvvdvppgntpedtrvfvdtivkcnlqslaktaeklaagaraags SEQ ID NO: 38
*Oryza_sativa_Japonica_Group* {115452475}
ref|NP_001049838.1|
mpcipassspgiphqhqhqhhralagvgmavgcaaeaavaaagvagtrcgalidgevpmevarhhehaepgsgrccsavvqh
vaapaaavwsvvrrfdqpqaykrfvrscallagdggvgtlrevrwsglpaassrerleilddeshvlsfrvvggehrlknylsvttv
hpspsaptaatvvvesyvvdvppgntpedtrvfvdtivkcnlqslaktaeklaagaraags SEQ ID NO: 39
*Medicago_truncatula* {217075076}
gb|ACJ85898.1|
mpspvqfqrfdsntaitngvncpkqiqacryalsslkptvsvpetvvdhhmhvvgqnqcysvviqtinasvstvwsvvrrfdyp
qgykhfvkscnvvasgdgirvgalrevrlvsglpavssterldildeerhvisfsvvggvhrcmyrsvttlhgdgnggtvviesyv
vdvpqgntkeetcsfadtivrcnlqslvqiaekl SEQ ID NO: 40
*Zea_mays* {195608982}
gb|ACG26321.1|
mpfaasrtsqqqhsrvatngravavcaghagvpdevarhhehavaagqccaamvqsiaapvdavwslvrrfdqpqrykrfirs
chlvdgdgaevgsvrelllvsglpaessrerleirdderrvisfrvlggdhrlanyrsvttvheaapsqdgrpltmwesywdvpp
gntveetrifvdtivrcnlqslegtvirqleiaamphddnqn SEQ ID NO: 41
*Zea_mays* {194705858}
gb|ACF87013.1|
mremssidqehqrgsssrstmpfaasrtsqqqhsrvatngravavcaghagvpdevarhhehavaagqccaamvqsiaapvd
avwslvrrfdqpqrykrfirschlvdgdgaevgsvrelllvsglpaessrerldrdderrvisfrvlggdhrlanyrsvttvheaapsq
dgrpltmvvesyvvdvppgntveetrifvdtivrcnlqslegtvirqleiaamphddnqn SEQ ID NO: 42
*Physcomitrella_patens* subsp._patens {168019160}
ref|XP_001762113.1|
mmqekqgrpdfqflleqqqdlicrfhkhellphqcgsillqqikapvqtvwlivrrfdcpqvykrfiqrcdivegdgvvgsirevq
lvssipatssierleilddeehiisfrvlggghrlqnywsvtsllirheiqgqmgtlvlesyvvdipdgntreethtfvdtvvrcnlkala
qvseqkhllnsnekpaap SEQ ID NO: 43
*Vitis_vinifera* {157354734}
emb|CAQ48052.1|
mkvyspsqilaergpraqamgnlyhthhllpnqcsslvvqttdaplpqvwsmvrrfdrpqsykrfvrgctlrrgkggvgsvrev
nivsglpaeislerldkldddlhvmrftviggdhrlanyhstltlhedeedgvrktwmesyvvdpggnsagetcvfantiigfnl
kalaavtetmalkanipsgf SEQ ID NO: 44
*Physcomitrella_patens_subsp._patens* {168030621}
ref|XP_001767821.1|
mqqvkgrqdfqrlleaqqdlicryhthelkahqcgsillqqikvplpivwaivrsfdkpqvykrfiqtckitegdggvgsirevhlv
ssvpatcsierleilddekhiisfrvlggghrlqnyssvsslheleveghpctlvlesymvdipdgntreethmfvdtvvrcnlkslaq
iseqqvnkdclqqkqhdqqqmyqqrhpplppipitdknmer SEQ ID NO: 45
*Physcomitrella_patens_subsp._patens* {168028995}
ref|XP_001767012.1|
mrfdighndvrgfftceeehayalhsqtvelnqcgsilmqqihapievvwsivrsfgspqiykkfiqaciltvgdggvgsirevflv
sgvpatssierleilddekhvfsfrvlkgghrlqnyrsvttlheqevngrqtttvlesywdvpdgntreethmfadtvvmcnlksla
qvaewramqgitqqlstssl SEQ ID NO: 46
*Vitis_vinifera* {147840019}
emb|CAN72620.1|
mgnlyhthhllpnqcsslvvqttdaplpqvwsmvrrfdrpqsykrfvrgctlrrgkggvgsvrevnivsglpaeislcrldkldddl
hvmrftviggdhrlanyhstltlhedeedgvrktvvmesywdvpggnsagetcyfantiigfnlkalaavtetmalkanipsgf

| INFORMAL SEQUENCE LISTING |
|---|

SEQ ID NO: 47
*Picea_sitchensis* {116785512}
gb|ABK23752.1|
medlsswregramwlgnppseselvcrhhrhelqgnqcssflvkhirapvhlvwsivrtfdqpqkykpfvhscsvrggitvgsir
nvnvksglpataseerleilddnehvfsikilggdhrlqnyssiitvhpeiidgrpgtlviesyvvdvpegntreetrffvealvkcnlk
sladvserlasqhhtellert SEQ ID NO: 48
*Solanum_tuberosum* {78191398}
gb|ABB29920.1|
mnangfcgvekeyirkhhlhepkenqcssflvkhirapvhlvwslvrrfdqpqkykpfisrcivqgdleigslrevdvksglpatt
sterlelldddeehilsvrivggdhrlmyssvisvhpevidgrpgtwlesfvvdvpegntkdetcyfvealincnlksladiservav
qdrtepidqv SEQ ID NO: 49
*Medicago_truncatula* {217075184}
gb|ACJ85952.1|
mnngceqqqysvietqyirrhhkhdlrdnqcssalvkhikapvhlvwslvrrfdqpqkykpfisrcimqgdlsigsvrevnvks
glpattsterleqlddeehilgirivggdhrlmyssiitvhpgvidgrpgtmviesfvvdvpegntkdetcyfvealirynlssladvs
ermavqgrtdpininp SEQ ID NO: 50
*Vitis_vinifera* {157358179}
emb|CAO6S816.1|
msgygcikmedeyirrhhrheirdnqcssslvkhikapvhlvwslvrsfdqpqkykpfvsrcivqgdleigsvrevnvksglpat
tsterlelldddeehifgmrivggdhrlknyssivtvhpeiidgrpgtlviesfvvdvpdgntkdetcyfvealikcnlksladvserlai
qdnepidrm SEQ ID NO: 51
*Vitis_vinifera* {157360187}
emb|CAQ69376.1|
mngnglssmeseyirrhhrhepaenqcssalvkhikapvplvwslvrrfdqpqkykpfisrcwqgnleigslrevdvksglpat
tsterleildddehilsmriiggdhrlmyssiislhpeiidgrpgtmviesywdvpegntkdetcyfvealikcnlksladvserlav
qdrtepidrm SEQ ID NO: 52
*Oryza_sativa_Japonica_Group* {125597584}
gb|EAZ37364.1|
meahveralregIteeeraalepavmahhtfppstttattaaatctslvtqrvaapvravwpivrsfgnpqrykhfvrtcalaagngp
sfgsvrevtvvsgpsrlppgterlemldddrhiisfrvvggqhrlniyrsvtsvtefqppaagpgpappycvvvesyvvdvpdgnt
aedtrmftdtvvklnlqmlaavaedsssasrrrd SEQ ID NO: 53
*Capsicum_annuum* {47558817}
gb|AAT35532.1|
mmnangfsgvekeyirkhhlhqpkenqcssflvkhirapvhlvwslvrrfdqpqkykpfvsrciaqgdleigslrevdvksglp
attsterlelldddeehilsfriiggdhrlmyssiislhpevidgrpgtlviesfvvdvpqgntkdetcyfvealincnlksladvserlav
qdrtepidqv SEQ ID NO: 54
*Populus_trichocarpa* {118481075}
gb|ABK92491.1|
mngsdaysateaqyvrrhhkheprenqctsalvkhikapahlvwslvrrfdqpqrykpfvsrcvmngelgigsvrevnvksglp
attsterlelldddeehilgvqivggdhrlknyssimtvhpefidgrpgtlviesfivdvpdgntkdetcyfvealircnlksladvser
mavqdrvepvnqf SEQ ID NO: 55
*Capsicum_annuum* {104304209}
gb|ABF72432.1|
mnangfsgvekeyirkhhlhqpkenqcssflvkhirapvhlvwslvrrfdqpqkykpfvsrciaqgdleigslrevdvksglpatt
sterlelldddeehilsfriiggdhrlmyssiislhpevidgrpgtlviesfvvdvpqgntkdetcyfvealincnlksladvserlavqdr
tepidqv SEQ ID NO: 56
*Populus_trichocarpa_x_Populus_deltoides* {118489403}
gb|ABK96S05.1|
mngsdaysateaqyvrrhhkheprenqctsalvkhikapahlvwslvrrfdqpqrykpfvsrcvmngelgigsvrevnvksglp
attsterlelldddeehilgvqivggdhrlknyssimtvhpefidgrpgtlviesfivdvpdgntkdetcyfvkalircnlksladvser
mavqdrvepvnqf SEQ ID NO: 57
*Pisum_sativum* {56384584}
gb|AAV85853.1|
mnnggeqysaietqyirrhhkhdlrdnqcssalvkhikapvhlvwslvrrfdqpqkykpfvsrcimqgdlgigsvrevnvksgl
pattsterleqlddeehilgirivggdhrlrnyssvitvhpevidgrpgtmviesfvvdvpegntrdetcyfvealirgnlssladvser
mavqgrtdpinvnp

| INFORMAL SEQUENCE LISTING |
|---|

SEQ ID NO: 58
*Vitis_vinifera* {157349888}
emb|CAO39744.1|
meaqvicrhhaheprenqcssvlvrhvkapanlvwslvrrfdqpqkykpfvsrcvvqgdlrigsvrevnvktglpattsterlelf
dddehvlgikildgdhrlmyssvitvhpeiidgrpgtlviesfvvdvpegntkddtcyfvralincnlkclaevsermamlgrvep
anav SEQ ID NO: 59
*Vitis_vinifera* {147856414}
emb|CAN82501.1|
mmeaqvicrhhaheprenqcssvlvrhvkapanlvwslvrrfdqpqkykpfvsrcvvqgdlrigsvrevnvktglpattsterlel
fdddehvlgikildgdhrlmyssvitvhpeiidgrpgtlviesfvvdvpegntkddtcyfvralincnlkclaevsennamlgrve
panav SEQ ID NO: 60
*Arachis_hypogaea* {196196276}
gb|ACG76109.1|
mmngscgggggeaygaieaqyirrhhrheprdnqctsalvkiiirapvhlvwslvrrfdqpqkykpfvsrcimqgdlgigsvr
evnvksglpattsterleqlddeehilgirivggdhrlmyssiitvhpeviegrpgtmviesfvvdvpdgntkdetcxfvealircnls
sladvsermavqgrtdpinq SEQ ID NO: 61
*Zea_mays* {195639836}
gb|ACG39386.1|
mvvemdggvgvaaggggaqtpapapprrwrladercdlrametdyvrrfhrheprdhqcssavakhikapvhlvwslvrrf
dqpqltkpfvsrcemkgnieigsvrevnvksglpatrsterlellddderilsvrfvggdhrlqnyssiltvhpevidgrpgtlviesfv
vdvpdgntkdetcyfveallkcnlrslaevsegqvimdqtepldr SEQ ID NO: 62
*Zea_mays* {194691986}
gb|ACF80077.1|
mvvemdggvgvaaggggaqtpappprrwrladercdlrametdyvrrfhrheprdhqcssavakhikapvhlvwslvrrf
dqpqlfkpfvsrcemkgnieigsvrevnvksglpatrsterlellddderilsvrfVggdhrlqnyssiltvhpevidgrpgtlviesfv
vdvpdgntkdetcyfveallkcnlrslaevsegqvimdqtepldr SEQ ID NO: 63
*Oryza_sativa*_Japonica_Group {115468346}
ref|NP_001057772.1|
inngvggaggaaagklpmvshrrvqvvrladercelreeemeyirrflirhepssnqctsfaakhikaplhtvwslvrrfdqpqlfk
pfvmcvmreniiatgcirevnvqsglpatrsterlellddnehilkvnfiggdhmlknyssiltvhsevidgqlgtlvvesfivdvpe
gntkddisyfienvlrcnlrtladvseerlanp SEQ ID NO: 64
*Oryza_sativa*_Indica_Group {125555582}
gb|EAZ01188.1|
mngaggaggaaagklpmvshrqvqwrladercelreeemeyirqfhrhepssnqctsfvakhikaplqtvwslvrrfdqpqlfk
pfvrkcvmreniiatgcvrevnvqsglpatrsterlellddnehilkvkfiggdhmlknyssiltihsevidgqlgtlvvesfvvdipe
gntkddicyfienilrcnlmtladvseerlanp SEQ ID NO: 65
*Oryza_sativa*_Japonica_Group {125581525}
gb|EAZ22456.1|
mvevgggaaeaaagrrwrladercdlraaeteyvrrfhrheprdhqcssavakhikapvhlvwslvrrfdqpqlfkpfvsrcem
kgnieigsvrevnvksglpatrsterlellddnehilsvrfvggdhrlknyssiltvhpevidgrpgtlviesfwdvpegntkdetcy
fveallkcnlkslaevserlvcqgpnrapstr SEQ ID NO: 66
*Oryza_sativa*_Japonica_Group {115445369}
ref|NP_QQ1046464.1|
mvevgggaaeaaagrrwrladercdlraaeteyvrrfhrheprdhqcssavakhikapvhlvwslvrrfdqpqlfkpfvsrcem
kgnieigsvrevnvksglpatrsterlellddnehilsvrfvggdhrlknyssiltvhpevidgrpgtlviesfvvdvpegntkdetcy
fveallkcnlkslaevserlwkdqtepldr SEQ ID NO: 67
*Medicago_truncatula* {217075288}
gb|ACJ86004.1|
mekmngtenngvfhstemeyirrhhnqqpgenqcssalvkhirapvplvwslvrrfdqpqkykpfvsrcvvrgnleigslrev
dvksglpattsterlevlddnehilsiriiggdhrlmyssimslhpeiidgrpgtlviesfVvdvpegntkdetcyfvealikcnlksls
dvseghavqdltepldrvhellisg SEQ ID NO: 68
*Medicago_truncatula* {217071196}
gb|ACJ83958.1|
mekmngtenngvfnstemeyirrhhnqqpgenqcssalvkhirapvplvwslvrrfdqpqkykpfvsrcvvrgnleigslrev
dvksglpattsterlevlddnehilsiriiggdhrlmyssimslhpeiidgrpgtlviesfvvdvpegntkdetcyfvealikcnlksls
dvseghaaqdltepldrmhellisg

| INFORMAL SEQUENCE LISTING |
|---|

SEQ ID NO: 69
*Zea_mays* {195625792}
gb|ACG34726.1|
mvglvggstaraehvvanaggeaeyvrrmhrhaptehqctstlvkhikapvhlvwqlvrrfdqpqrykpfvmcwrgdqlev
gslrdvnvktglpattsterleqldddlhilgvkfvggdhrlqnyssiitvhpesidgrpgtlviesfvvdvpdgntkdetcyfveavi
kcnlnslaevseqlavesptslidq SEQ ID NO: 70
*Zea_mays* {195608384}
gb|ACG26022.1|
mvglvggstaraehvvanaggeaeyvmnhrhaptehqctstlvkhikapvhlvwelvrrfdqpqrykpfvmcvvrgdqlev
gslrdvnvktglpattsterleqldddlhilgvkfvggdhrlqnyssiitvhpesidgrpgtlviesfvvdvpdgntkdetcyfveavi
kcnlnslaevseqlavesptslidq SEQ ID NO: 71
*Zea_mays* {194704156}
gb|ACF86162.1|
mvmvemdggvggggggggqtpaprrwrladercdlrametdyvrrfhrheprehqcssavakhikapvhlvwslvrrfdqpql
fkpfvsrcemkgnieigsvrevnvksglpatrsterlellddnehilsvrfvggdhrlqnyssiltvhpevidgrpgtlviesfwdvp
dgntkdetcyfveallkcnlkslaevserqwkdqtepldr SEQ ID NO: 72
*Oryza_sativa_Japonica_Group* {115468344}
ref|NP_001057771.1|
mngaggaggaaagklpmvshrrvqcrladkrcelreeemeyirqfhrhepssnqctsfvakhikaplqtvwslvrrfdqpqlfk
pfvrkcvmreniivtgcvrevnvqsglpatrsterlellddnehilkvkfiggdhmlknyssiltihsevidgqlgtlwesfvvdipd
gntkddicyfienvlrcnlmtladvseerlan SEQ ID NO: 73
*Zea_mays* {194701978}
gb|ACF85073.1|
mvglvggstaraehwanaggeteyvrrlhrhapaehqctstlvkhikapvhlvwelvrsfdqpqrykpfvmcvvrgdqlevgs
lrdvnvktglpattsterleqldddlhilgvkfvggdhrlqnyssiitvhpesidgrpgtlviesfVvdvpdgntkdetcyfveavikc
nlkslaevseqlavesptspidq SEQ ID NO: 74
*Oryza_sativa_Indica_Group* {125555585}
gb|EAZ01191.1|
mngvggaggaaagklpmvshrrvqwrladercelreeemeyirrfhrhepssnqctsfaakhikaplhtvwslvrrfdqpqlfk
pfvmcvmreniiatgcirevnvqsglpatrsterlellddnehilkvkfiggdhmlknyssiltvhsevidgqigtlvvesfivdvle
gntkddisyfienvlrcnlrtladvseerlanp SEQ ID NO: 75
*Oryza_sativa_Japonica_Group* {115462647}
ref|NP_001054923.1|
mvglvggggwrvgddaaggggggavaagaaaaaeaehmrrlhshapgehqcssalvkhikapvhlvwslvrsfdqpqrykp
fvsrcvvrggdleigsvrevnvktglpattsterlelldddehilsvkfvggdhrlmyssivtvhpesidgrpgtlviesfvvdvpdg
ntkdetcyfveavikcnltslaevserlavqsptspleq SEQ ID NO: 76
*Oryza_sativa_Japonica_Group* {50251668}
dbj|BAD29692.1|
mvemdaggrpepsppsgqcssavtmrinapvhlvwsivrrfeephifqpfvrgctmrgstslavgcvrevdfksgfpakssver
leilddkehvfgvriiggdhrlknyssvltakpevidgepatlvsesfvvdvpegntadetrhfveflircnlrslamvsqrlllaqgdl
aeppaq SEQ ID NO: 77
*Vitis_vinifera* {147797548}
emb|CAN64668.1|
mngnglssmeseyirrhhrhepaenqcssalvkhikapvplvwslvrrfdqpqkykpfisrcwqgnleigslrevdvksglpat
tsterlelldddehilsmriiggdhrlmyssiislhpeiidgrpgtmviesyvvdvpegntkdetcyfsladvserlavagtvtepidr
m SEQ ID NO: 78
*Oryza_sativa_Indica_Group* {218190432}
gb|EEC72859.1|
mvemdaggipepsppsgqcssavtmrinapvhlvwsivrrfeephifqpfvrgctmrgstslavgcvrevdfksgfsakssver
leilddkehvfgvriiggdhrlknyssvltakpevidgepatlvsesfvidvpegntadetrhfveflircnlrslamvsqrlllaqgdl
aeppaq SEQ ID NO: 79
*Oryza_sativa_Japonica_Group* {125585934}
gb|EAZ26598.1|
mpcipasspgiphqhqhqhhralagvgmavgcaaeeaavaaagvagtrcgahdgevpmevarhhehaepgsgrccsavvqh
vaapaaavwswrrfdqpqaykrfvrscallagdgglgkvrerleilddeshvlsfrwggehrlknylsvttvhpspsaptaatvv
vesyvvdvppgntpedtrvfvdtivkcnlqslaktaeklaagaraags

| INFORMAL SEQUENCE LISTING |
|---|

```
SEQ ID NO: 80
Rheum_australe {197312913}
gb|ACH63237.1|
mngdgyggseeefvkryhehvladhqcssvlvehinaplhlvwslvrsfdqpqkykpfvsrcvvqggdleigsvrevdvksgl
pattsmeelellddkehvlrvkfvggdhrlknyssivslhpeiiggrsgtmviesfivdiadgntkeetcyfieslincnlkslscvser
lavediaeriaqm SEQ ID NO: 81
Oryza_sativa_Japonica_Group {125593228}
gb|EAZ33287.1|
mvglvgggwrvgddaagggggavaagaaaaaeaehmrrlhsqgprrapvqlrarqahqgscspppriecanfavflaardp
kivwslvrsfdqpqrykpfvsrcwrggdleigsvrevnvktglpattsterlellddehilsvkfvggdhrlmyssivtvhpesid
grpgtlviesfvvdvpdgntkdetcyfveavikcnltslaemvrmislvlpfmlvdrmsgitceshlettlvrcgeyavlahv SEQ ID NO: 82
Oryza_sativa_Japonica_Group {125581370}
gb|EAZ22301.1|
mephmeralreavaseaerrelegvvrahhtgvvnaplaavwphrarvrptrsgtstsssrassppgdgatvgsvrevavvsglpa
ststerleildddrhvlsfrvvggdhrlmyrsvtsvtefsspssppropycvvvesyvvdvpegnteedtrmftdtvvklnlqklaav
atsssppaagnhh SEQ ID NO: 83
Oryza_sativa_Japonica_Group {125581524}
gb|EAZ22455.1|
mevvwsivrrfeephifqpfvrgctmrgstslavgcvrevdfksgfpakssverleilddkehvfgvriiggdhrlknyssvltakp
evidgepatlvsesfvvdvpegntadetrhfveflircnlrslamvsqrlllaqgdlaeppgq SEQ ID NO: 84
Oryza_sativa_Japonica_Group {125594587}
gb|EAZ34646.1|
mpytaprpsppqhsriggcggggvlkaagaaghaascvavpaevarhhehaagvgqccsavvqaiaapvdavwrtstssgaa
aswtatatagplpvgsvrefrvlsglpgtssrerleildderrvlsfrvvggehrlsnyrsvttvhetaagaaaavvvesyvvdvphgn
tadetrmfvdtivrcnlqslartaeqlalaapraa SEQ ID NO: 85
Vitis_vinifera {147770961}
emb|CAN76441.1|
mpisslpfslytvtpnplklitthahaftphthiftlkfmshtycphihhitsihythllxpiphmplqpplpphpilpsmpafqhlyst
nqhlqvalfsargpnirdfnfqdadllkldilapgsliwaawspngtdeanyvgegsptvamiakrgprhgkymafcxmyrdn
vapkgvnxavatvktkrtiqlktsleiachyaginisgingevmpgqweyqvgpgqcssllaqrvhvplsavgsvvhrfdkpqr
yqhvikscriedgfemrmgxlrdvniisglptatntgrldmqdderhvtrcphqrqseskytennnsdassikspingpsehlkta
aspkteshividtskflneedfegkdetsssnqvqiedenwetrfpntdagiw SEQ ID NO: 86
Vitis_vinifera {147828564}
emb|CAN59881.1|
mpsaxksstvplslxqfklglrhghrvipwgdldslamlqrqldvdilvtghthrftaykheggwinpgsatgafgsitydvnpsf
vlmdidglrvvvcvyelidetaniikelharkisfgtksmixclllkrrstpkfrrkklflfqcrvqmtltltnlavsgiaqtlqvdqwtv
califmtrrdihldkarfldfkdmgklladasglrkalsggxvtagmaifdtmrhirpdvptvcvglaavamiakrgprhgkyma
fcpmyrdnvapkgvnvavvtvktkrtiqlktsleiachyaginisgingevmpgqvveyqvgpgqcssllaqrvhvplsavgsv
vhrfdkpqryqhvikscriedgfemrmgrlrdvniisglptatntgrldmqddexhvtrcphqrqseskytennnsdassvkspi
ngpsehlktaax SEQ ID NO: 87
Oryza_sativa_Indica_Group {149392053}
gb|ABR25904.1|
eigsvrevnvktglpattsterlellddehilsvkfvggdhrlmyssivtvhpesidgrpgtlviesfvvdvpdgntkdetcyfvea
vikcnl SEQ ID NO: 88
Zea_mays {194701080}
gb|ACF84624.1|
mvvemdggvgvaaagggggaqtpappprrwrladercdlrametdyvrrfhrheprdhqcssavakhikapvhlvwslvrrf
dqpqlfkpfvsrcemkgnieigsvrevnvksglpatrsterlelldderilsvrfvggdhrlqvcsvlhlsifcaaharyfahhlkcv
leflcqmhldvlpcddaile SEQ ID NO: 89
Oryza_sativa_Japonica_Group {125597418}
gb|EAZ37198.1|
mngctggaggvaagrlpavslqqaqwklvdercelreeemeyvrrfhrheigsnqcnsfiakhvraplqnvwslvrrfdqpqiy
kpfvrkcvmrgnvetgsvreiivqsglpatrsierleflddneyilrvkfiggdhmlkkripkktyaissrtcsdsaiiavgqsncape
itamnggvsiqpwlillaffsspsnqtnpdslrdmhpgswfqilivlamftcskgsvlppsekvnv SEQ ID NO: 90 (consensus sequence)
CxSxxxxxxxAPxxxxWxxxxxFxxPxxxxxxFxxxC
```

INFORMAL SEQUENCE LISTING

SEQ ID NO: 91 (consensus sequence)
GxxRxVxxxSxxPAxxSxExLxxxD

SEQ ID NO: 92 (consensus sequence)
ESxxVDxPxGxxxxxTxxFxxxxxxxNLxxL

SEQ ID NO: 93 (consensus sequence)
HxxxxxxxxCxSxxxxxxxAPxxxxWxxxxxFxxPxxYKxFxxxC SEQ ID NO: 94 (consensus sequence)
VGRxVxVxSGLPAxxSxExLxxxDxxxxxxxFxxxGGxHRLxNYxSVT SEQ ID NO: 95 (consensus sequence)
VxESYxVDxPxGNxxxxTxxFxDxxxxxNLQxL SEQ ID NO: 96 (consensus sequence)
HxHxxxxxQCxSxLVKxIxAPxHxVWSxVRRFDxPQKYKPFxSRCxVxGx SEQ ID NO: 97 (consensus sequence)
ExGxxREVxxKSGLPATxSTExLExLDDxEHILxIxIxGGDHRLKNYSSxxxxHxExIxGxxGT
x SEQ ID NO: 98 (consensus sequence)
xxESFVVDVPxGNTKxxTCxFVExLIxCNLxSLAxxxERL SEQ ID NO: 99 (consensus sequence)
CxSxxVxTIxAPLxLVWSILRxFDxPxxxxxFVKxCxxxSGxGG SEQ ID NO: 100 (consensus sequence)
GSVRxVTxVSxxPAxFSxERLxELDDESHVMxxSIIGGxHRLVNYxSKT

What is claimed is:

1. A non-naturally occurring isolated mutant nucleic acid comprising a polynucleotide encoding a mutated PYR/PYL receptor polypeptide comprising one or more amino acid substitutions in a type 2 protein phosphatase (PP2C) binding interface at a position corresponding to K63, I82, I84, D154, M158, T162, L166, or K170 in the PYR1 polypeptide as set forth in SEQ ID NO:1, wherein the mutated PYR/PYL receptor polypeptide inhibits the activity of a PP2C polypeptide in the presence of abscisic acid (ABA) to a greater extent than a wild-type control PYR/PYL receptor polypeptide in the presence of the same concentration of ABA, wherein the mutated PYR/PYL receptor polypeptide does not inhibit the activity of the PP2C polypeptide in the absence of said ABA, wherein the mutated PYR/PYL receptor polypeptide comprises one or more amino acid substitutions corresponding to the amino acid substitution K63E, I82A/F/K/S, I84A/D/N/R/S/T, D154G/H/K/Q/R/W, M158G/W, T162H/K/L/M/W, L166A/G/K/M/N/R/S/T/W, or K170A/D/E/G/M/N/Q/R/T/V/Y in the PYR1 polypeptide as set forth in SEQ ID NO:1, and wherein the mutated PYR/PYL receptor polypeptide has at least 95% amino sequence identity to the amino acid sequence as set forth in SEQ ID NO:70.

2. The non-naturally occurring isolated mutant nucleic acid of claim 1, wherein the PP2C polypeptide is HAB1.

3. A non-naturally occurring mutant plant comprising a mutated PYR/PYL receptor polypeptide comprising one or more amino acid substitutions in a type 2 protein phosphatase (PP2C) binding interface at a position corresponding to K63, I82, I84, D154, M158, T162, L166, or K170 in the PYR1 polypeptide as set forth in SEQ ID NO:1, wherein the mutated PYR/PYL receptor polypeptide inhibits the activity of a PP2C polypeptide in the presence of abscisic acid (ABA) to a greater extent than a wild-type control PYR/PYL receptor polypeptide in the presence of the same concentration of said ABA, and wherein the mutated PYR/PYL receptor polypeptide does not inhibit the activity of the PP2C polypeptide in the absence of said ABA, wherein the mutated PYR/PYL receptor polypeptide comprises one or more amino acid substitutions corresponding to the amino acid substitution K63E, I82A/F/K/S, I84A/D/N/R/S/T, D154G/H/K/Q/R/W, M158G/W, T162H/K/L/M/W, L166A/G/K/M/N/R/S/T/W, or K170A/D/E/G/M/N/Q/R/T/V/Y in the PYR1 polypeptide as set forth in SEQ ID NO:1, and wherein the mutated PYR/PYL receptor polypeptide has at least 95% amino sequence identity to the amino acid sequence as set forth in SEQ ID NO:70.

4. The non-naturally occurring mutant plant of claim 3, wherein the PP2C polypeptide is HAB1.

5. The non-naturally occurring mutant plant of claim 3, comprising a heterologous promoter operably linked to the polynucleotide encoding said mutated PYR/PYL receptor polypeptide.

6. The non-naturally occurring mutant plant of claim 3, wherein the mutated PYR/PYL receptor polypeptide comprises an amino acid substitution corresponding to K63E in the PYR1 polypeptide as set forth in SEQ ID NO:1.

7. The non-naturally occurring mutant plant of claim 3, wherein the mutated PYR/PYL receptor polypeptide comprises an amino acid substitution corresponding to I82A/F/K/S in the PYR1 polypeptide as set forth in SEQ ID NO:1.

8. The non-naturally occurring mutant plant of claim 3, wherein the mutated PYR/PYL receptor polypeptide comprises an amino acid substitution corresponding to I84A/D/N/R/S/T in the PYR1 polypeptide as set forth in SEQ ID NO:1.

9. The non-naturally occurring mutant plant of claim 3, wherein the mutated PYR/PYL receptor polypeptide comprises an amino acid substitution corresponding to D154G/H/K/Q/R/W in the PYR1 polypeptide as set forth in SEQ ID NO:1.

10. The non-naturally occurring mutant plant of claim 3, wherein the mutated PYR/PYL receptor polypeptide comprises an amino acid substitution corresponding to M158G/W in the PYR1 polypeptide as set forth in SEQ ID NO:1.

11. The non-naturally occurring mutant plant of claim 10, wherein the mutated PYR/PYL receptor polypeptide comprises an amino acid substitution corresponding to M158W in the PYR1 polypeptide as set forth in SEQ ID NO:1.

12. The non-naturally occurring mutant plant of claim 3, wherein the mutated PYR/PYL receptor polypeptide comprises an amino acid substitution corresponding to T162H/K/L/M/W in the PYR1 polypeptide as set forth in SEQ ID NO:1.

13. The non-naturally occurring mutant plant of claim 12, wherein the mutated PYR/PYL receptor polypeptide comprises an amino acid substitution corresponding to T162W in the PYR1 polypeptide as set forth in SEQ ID NO:1.

14. The non-naturally occurring mutant plant of claim 3, wherein the mutated PYR/PYL receptor polypeptide comprises an amino acid substitution corresponding to L166AG/K/M/N/R/S/T/W in the PYR1 polypeptide as set forth in SEQ ID NO:1.

15. The non-naturally occurring mutant plant of claim 14, wherein the mutated PYR/PYL receptor polypeptide comprises an amino acid substitution corresponding to L166G/K/N/R/S/T in the PYR1 polypeptide as set forth in SEQ ID NO:1.

16. The non-naturally occurring mutant plant of claim 3, wherein the mutated PYR/PYL receptor polypeptide comprises an amino acid substitution corresponding to K170A/D/E/G/M/N/Q/R/T/V/Y in the PYR1 polypeptide as set forth in SEQ ID NO:1.

17. The non-naturally occurring mutant plant of claim 16, wherein the mutated PYR/PYL receptor polypeptide comprises an amino acid substitution corresponding to K170A/D/E/G/M/T/V/Y in the PYR1 polypeptide as set forth in SEQ ID NO:1.

18. The non-naturally occurring mutant plant of claim 3, wherein the mutated PYR/PYL receptor polypeptide is identical in amino acid sequence to the amino acid sequence as set forth in SEQ ID NO:70 except for said amino acid substitutions.

\* \* \* \* \*

SEQUENCE LISTING

<160> NUMBER OF SEQ ID NOS: 100

<210> SEQ ID NO 1
<211> LENGTH: 191
<212> TYPE: PRT
<213> ORGANISM: Arabidopsis thaliana

<400> SEQUENCE: 1

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys His Phe Ile Lys Ser
    50                  55                  60

Cys Ser Val Glu Gln Asn Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Asp Thr Arg Met Phe Ala
145                 150                 155                 160

Asp Thr Val Val Lys Leu Asn Leu Gln Lys Leu Ala Thr Val Ala Glu

-continued

```
                165                 170                 175
Ala Met Ala Arg Asn Ser Gly Asp Gly Ser Gly Ser Gln Val Thr
            180                 185                 190

<210> SEQ ID NO 2
<211> LENGTH: 221
<212> TYPE: PRT
<213> ORGANISM: Arabidopsis thaliana

<400> SEQUENCE: 2

Met Ala Asn Ser Glu Ser Ser Ser Pro Val Asn Glu Glu Glu Asn
1               5                   10                  15

Ser Gln Arg Ile Ser Thr Leu His His Gln Thr Met Pro Ser Asp Leu
            20                  25                  30

Thr Gln Asp Glu Phe Thr Gln Leu Ser Gln Ser Ile Ala Glu Phe His
            35                  40                  45

Thr Tyr Gln Leu Gly Asn Gly Arg Cys Ser Ser Leu Leu Ala Gln Arg
        50                  55                  60

Ile His Ala Pro Pro Glu Thr Val Trp Ser Val Val Arg Arg Phe Asp
65                  70                  75                  80

Arg Pro Gln Ile Tyr Lys His Phe Ile Lys Ser Cys Asn Val Ser Glu
                85                  90                  95

Asp Phe Glu Met Arg Val Gly Cys Thr Arg Asp Val Asn Val Ile Ser
            100                 105                 110

Gly Leu Pro Ala Asn Thr Ser Arg Glu Arg Leu Asp Leu Leu Asp Asp
            115                 120                 125

Asp Arg Arg Val Thr Gly Phe Ser Ile Thr Gly Gly Glu His Arg Leu
        130                 135                 140

Arg Asn Tyr Lys Ser Val Thr Thr Val His Arg Phe Glu Lys Glu Glu
145                 150                 155                 160

Glu Glu Glu Arg Ile Trp Thr Val Val Leu Glu Ser Tyr Val Val Asp
                165                 170                 175

Val Pro Glu Gly Asn Ser Glu Glu Asp Thr Arg Leu Phe Ala Asp Thr
            180                 185                 190

Val Ile Arg Leu Asn Leu Gln Lys Leu Ala Ser Ile Thr Glu Ala Met
        195                 200                 205

Asn Arg Asn Asn Asn Asn Asn Ser Ser Gln Val Arg
210                 215                 220

<210> SEQ ID NO 3
<211> LENGTH: 190
<212> TYPE: PRT
<213> ORGANISM: Arabidopsis thaliana

<400> SEQUENCE: 3

Met Ser Ser Ser Pro Ala Val Lys Gly Leu Thr Asp Glu Glu Gln Lys
1               5                   10                  15

Thr Leu Glu Pro Val Ile Lys Thr Tyr His Gln Phe Glu Pro Asp Pro
            20                  25                  30

Thr Thr Cys Thr Ser Leu Ile Thr Gln Arg Ile His Ala Pro Ala Ser
        35                  40                  45

Val Val Trp Pro Leu Ile Arg Arg Phe Asp Asn Pro Glu Arg Tyr Lys
    50                  55                  60

His Phe Val Lys Arg Cys Arg Leu Ile Ser Gly Asp Gly Asp Val Gly
65                  70                  75                  80

Ser Val Arg Glu Val Thr Val Ile Ser Gly Leu Pro Ala Ser Thr Ser
```

```
                        85                  90                  95
Thr Glu Arg Leu Glu Phe Val Asp Asp His Arg Val Leu Ser Phe
            100                 105                 110

Arg Val Val Gly Gly Glu His Arg Leu Lys Asn Tyr Lys Ser Val Thr
            115                 120                 125

Ser Val Asn Glu Phe Leu Asn Gln Asp Ser Gly Lys Val Tyr Thr Val
            130                 135                 140

Val Leu Glu Ser Tyr Thr Val Asp Ile Pro Glu Gly Asn Thr Glu Glu
145                 150                 155                 160

Asp Thr Lys Met Phe Val Asp Thr Val Val Lys Leu Asn Leu Gln Lys
                165                 170                 175

Leu Gly Val Ala Ala Thr Ser Ala Pro Met His Asp Glu
            180                 185                 190

<210> SEQ ID NO 4
<211> LENGTH: 209
<212> TYPE: PRT
<213> ORGANISM: Arabidopsis thaliana

<400> SEQUENCE: 4

Met Asn Leu Ala Pro Ile His Asp Pro Ser Ser Ser Thr Thr Thr
1               5                   10                  15

Thr Ser Ser Ser Thr Pro Tyr Gly Leu Thr Lys Asp Glu Phe Ser Thr
                20                  25                  30

Leu Asp Ser Ile Ile Arg Thr His His Thr Phe Pro Arg Ser Pro Asn
            35                  40                  45

Thr Cys Thr Ser Leu Ile Ala His Arg Val Asp Ala Pro Ala His Ala
        50                  55                  60

Ile Trp Arg Phe Val Arg Asp Phe Ala Asn Pro Asn Lys Tyr Lys His
65                  70                  75                  80

Phe Ile Lys Ser Cys Thr Ile Arg Val Asn Gly Asn Gly Ile Lys Glu
                85                  90                  95

Ile Lys Val Gly Thr Ile Arg Glu Val Ser Val Val Ser Gly Leu Pro
            100                 105                 110

Ala Ser Thr Ser Val Glu Ile Leu Glu Val Leu Asp Glu Glu Lys Arg
            115                 120                 125

Ile Leu Ser Phe Arg Val Leu Gly Gly Glu His Arg Leu Asn Asn Tyr
        130                 135                 140

Arg Ser Val Thr Ser Val Asn Glu Phe Val Val Leu Glu Lys Asp Lys
145                 150                 155                 160

Lys Lys Arg Val Tyr Ser Val Val Leu Glu Ser Tyr Ile Val Asp Ile
                165                 170                 175

Pro Gln Gly Asn Thr Glu Glu Asp Thr Arg Met Phe Val Asp Thr Val
            180                 185                 190

Val Lys Ser Asn Leu Gln Asn Leu Ala Val Ile Ser Thr Ala Ser Pro
            195                 200                 205

Thr

<210> SEQ ID NO 5
<211> LENGTH: 207
<212> TYPE: PRT
<213> ORGANISM: Arabidopsis thaliana

<400> SEQUENCE: 5

Met Leu Ala Val His Arg Pro Ser Ser Ala Val Ser Asp Gly Asp Ser
1               5                   10                  15
```

```
Val Gln Ile Pro Met Met Ile Ala Ser Phe Gln Lys Arg Phe Pro Ser
             20                  25                  30

Leu Ser Arg Asp Ser Thr Ala Ala Arg Phe His Thr His Glu Val Gly
         35                  40                  45

Pro Asn Gln Cys Cys Ser Ala Val Ile Gln Glu Ile Ser Ala Pro Ile
     50                  55                  60

Ser Thr Val Trp Ser Val Val Arg Arg Phe Asp Asn Pro Gln Ala Tyr
 65              70                  75                  80

Lys His Phe Leu Lys Ser Cys Ser Val Ile Gly Gly Asp Gly Asp Asn
                 85                  90                  95

Val Gly Ser Leu Arg Gln Val His Val Val Ser Gly Leu Pro Ala Ala
                100                 105                 110

Ser Ser Thr Glu Arg Leu Asp Ile Leu Asp Asp Glu Arg His Val Ile
            115                 120                 125

Ser Phe Ser Val Val Gly Gly Asp His Arg Leu Ser Asn Tyr Arg Ser
130                 135                 140

Val Thr Thr Leu His Pro Ser Pro Ile Ser Gly Thr Val Val Val Glu
145                 150                 155                 160

Ser Tyr Val Val Asp Val Pro Pro Gly Asn Thr Lys Glu Glu Thr Cys
                165                 170                 175

Asp Phe Val Asp Val Ile Val Arg Cys Asn Leu Gln Ser Leu Ala Lys
                180                 185                 190

Ile Ala Glu Asn Thr Ala Ala Glu Ser Lys Lys Lys Met Ser Leu
                195                 200                 205

<210> SEQ ID NO 6
<211> LENGTH: 203
<212> TYPE: PRT
<213> ORGANISM: Arabidopsis thaliana

<400> SEQUENCE: 6

Met Arg Ser Pro Val Gln Leu Gln His Gly Ser Asp Ala Thr Asn Gly
  1               5                  10                  15

Phe His Thr Leu Gln Pro His Asp Gln Thr Asp Gly Pro Ile Lys Arg
             20                  25                  30

Val Cys Leu Thr Arg Gly Met His Val Pro Glu His Val Ala Met His
         35                  40                  45

His Thr His Asp Val Gly Pro Asp Gln Cys Cys Ser Ser Val Val Gln
     50                  55                  60

Met Ile His Ala Pro Pro Glu Ser Val Trp Ala Leu Val Arg Arg Phe
 65              70                  75                  80

Asp Asn Pro Lys Val Tyr Lys Asn Phe Ile Arg Gln Cys Arg Ile Val
                 85                  90                  95

Gln Gly Asp Gly Leu His Val Gly Asp Leu Arg Glu Val Met Val Val
                100                 105                 110

Ser Gly Leu Pro Ala Val Ser Ser Thr Glu Arg Leu Glu Ile Leu Asp
            115                 120                 125

Glu Glu Arg His Val Ile Ser Phe Ser Val Val Gly Gly Asp His Arg
130                 135                 140

Leu Lys Asn Tyr Arg Ser Val Thr Thr Leu His Ala Ser Asp Asp Glu
145                 150                 155                 160

Gly Thr Val Val Val Glu Ser Tyr Ile Val Asp Val Pro Pro Gly Asn
                165                 170                 175

Thr Glu Glu Glu Thr Leu Ser Phe Val Asp Thr Ile Val Arg Cys Asn
```

```
                 180                 185                 190

Leu Gln Ser Leu Ala Arg Ser Thr Asn Arg Gln
            195                 200

<210> SEQ ID NO 7
<211> LENGTH: 215
<212> TYPE: PRT
<213> ORGANISM: Arabidopsis thaliana

<400> SEQUENCE: 7

Met Pro Thr Ser Ile Gln Phe Gln Arg Ser Thr Ala Ala Glu Ala
1               5                  10                  15

Ala Asn Ala Thr Val Arg Asn Tyr Pro His His Gln Lys Gln Val
            20                  25                  30

Gln Lys Val Ser Leu Thr Arg Gly Met Ala Asp Val Pro Glu His Val
            35                  40                  45

Glu Leu Ser His Thr His Val Val Gly Pro Ser Gln Cys Phe Ser Val
        50                  55                  60

Val Val Gln Asp Val Glu Ala Pro Val Ser Thr Val Trp Ser Ile Leu
65                  70                  75                  80

Ser Arg Phe Glu His Pro Gln Ala Tyr Lys His Phe Val Lys Ser Cys
                85                  90                  95

His Val Val Ile Gly Asp Gly Arg Glu Val Gly Ser Val Arg Glu Val
                100                 105                 110

Arg Val Val Ser Gly Leu Pro Ala Ala Phe Ser Leu Glu Arg Leu Glu
            115                 120                 125

Ile Met Asp Asp Asp Arg His Val Ile Ser Phe Ser Val Val Gly Gly
        130                 135                 140

Asp His Arg Leu Met Asn Tyr Lys Ser Val Thr Thr Val His Glu Ser
145                 150                 155                 160

Glu Glu Asp Ser Asp Gly Lys Lys Arg Thr Arg Val Val Glu Ser Tyr
                165                 170                 175

Val Val Asp Val Pro Ala Gly Asn Asp Lys Glu Thr Cys Ser Phe
                180                 185                 190

Ala Asp Thr Ile Val Arg Cys Asn Leu Gln Ser Leu Ala Lys Leu Ala
            195                 200                 205

Glu Asn Thr Ser Lys Phe Ser
            210                 215

<210> SEQ ID NO 8
<211> LENGTH: 211
<212> TYPE: PRT
<213> ORGANISM: Arabidopsis thaliana

<400> SEQUENCE: 8

Met Glu Met Ile Gly Gly Asp Asp Thr Asp Thr Glu Met Tyr Gly Ala
1               5                  10                  15

Leu Val Thr Ala Gln Ser Leu Arg Leu Arg His Leu His Cys Arg
            20                  25                  30

Glu Asn Gln Cys Thr Ser Val Leu Val Lys Tyr Ile Gln Ala Pro Val
            35                  40                  45

His Leu Val Trp Ser Leu Val Arg Arg Phe Asp Gln Pro Gln Lys Tyr
        50                  55                  60

Lys Pro Phe Ile Ser Arg Cys Thr Val Asn Gly Asp Pro Glu Ile Gly
65                  70                  75                  80

Cys Leu Arg Glu Val Asn Val Lys Ser Gly Leu Pro Ala Thr Thr Ser
```

```
                    85                  90                  95

Thr Glu Arg Leu Glu Gln Leu Asp Asp Glu His Ile Leu Gly Ile
                100                 105                 110

Asn Ile Ile Gly Gly Asp His Arg Leu Lys Asn Tyr Ser Ser Ile Leu
            115                 120                 125

Thr Val His Pro Glu Met Ile Asp Gly Arg Ser Gly Thr Met Val Met
130                 135                 140

Glu Ser Phe Val Val Asp Val Pro Gln Gly Asn Thr Lys Asp Asp Thr
145                 150                 155                 160

Cys Tyr Phe Val Glu Ser Leu Ile Lys Cys Asn Leu Lys Ser Leu Ala
                165                 170                 175

Cys Val Ser Glu Arg Leu Ala Ala Gln Asp Ile Thr Asn Ser Ile Ala
                180                 185                 190

Thr Phe Cys Asn Ala Ser Asn Gly Tyr Arg Glu Lys Asn His Thr Glu
                195                 200                 205

Thr Asn Leu
        210

<210> SEQ ID NO 9
<211> LENGTH: 188
<212> TYPE: PRT
<213> ORGANISM: Arabidopsis thaliana

<400> SEQUENCE: 9

Met Glu Ala Asn Gly Ile Glu Asn Leu Thr Asn Pro Asn Gln Glu Arg
1               5                   10                  15

Glu Phe Ile Arg Arg His His Lys His Glu Leu Val Asp Asn Gln Cys
                20                  25                  30

Ser Ser Thr Leu Val Lys His Ile Asn Ala Pro Val His Ile Val Trp
            35                  40                  45

Ser Leu Val Arg Arg Phe Asp Gln Pro Gln Lys Tyr Lys Pro Phe Ile
        50                  55                  60

Ser Arg Cys Val Val Lys Gly Asn Met Glu Ile Gly Thr Val Arg Glu
65                  70                  75                  80

Val Asp Val Lys Ser Gly Leu Pro Ala Thr Arg Ser Thr Glu Arg Leu
                85                  90                  95

Glu Leu Leu Asp Asp Asn Glu His Ile Leu Ser Ile Arg Ile Val Gly
                100                 105                 110

Gly Asp His Arg Leu Lys Asn Tyr Ser Ser Ile Ile Ser Leu His Pro
            115                 120                 125

Glu Thr Ile Glu Gly Arg Ile Gly Thr Leu Val Ile Glu Ser Phe Val
        130                 135                 140

Val Asp Val Pro Glu Gly Asn Thr Lys Asp Glu Thr Cys Tyr Phe Val
145                 150                 155                 160

Glu Ala Leu Ile Lys Cys Asn Leu Lys Ser Leu Ala Asp Ile Ser Glu
                165                 170                 175

Arg Leu Ala Val Gln Asp Thr Thr Glu Ser Arg Val
                180                 185

<210> SEQ ID NO 10
<211> LENGTH: 187
<212> TYPE: PRT
<213> ORGANISM: Arabidopsis thaliana

<400> SEQUENCE: 10

Met Met Asp Gly Val Glu Gly Gly Thr Ala Met Tyr Gly Gly Leu Glu
```

```
            1               5                  10                 15
        Thr Val Gln Tyr Val Arg Thr His His Gln His Leu Cys Arg Glu Asn
                        20                 25                 30
        Gln Cys Thr Ser Ala Leu Val Lys His Ile Lys Ala Pro Leu His Leu
                        35                 40                 45
        Val Trp Ser Leu Val Arg Arg Phe Asp Gln Pro Gln Lys Tyr Lys Pro
                50                 55                 60
        Phe Val Ser Arg Cys Thr Val Ile Gly Asp Pro Glu Ile Gly Ser Leu
        65                 70                 75                 80
        Arg Glu Val Asn Val Lys Ser Gly Leu Pro Ala Thr Thr Ser Thr Glu
                        85                 90                 95
        Arg Leu Glu Leu Leu Asp Asp Glu Glu His Ile Leu Gly Ile Lys Ile
                        100                105                110
        Ile Gly Gly Asp His Arg Leu Lys Asn Tyr Ser Ser Ile Leu Thr Val
                        115                120                125
        His Pro Glu Ile Ile Glu Gly Arg Ala Gly Thr Met Val Ile Glu Ser
                        130                135                140
        Phe Val Asp Val Pro Gln Gly Asn Thr Lys Asp Glu Thr Cys Tyr
        145                150                155                160
        Phe Val Glu Ala Leu Ile Arg Cys Asn Leu Lys Ser Leu Ala Asp Val
                        165                170                175
        Ser Glu Arg Leu Ala Ser Gln Asp Ile Thr Gln
                        180                185
```

<210> SEQ ID NO 11
<211> LENGTH: 183
<212> TYPE: PRT
<213> ORGANISM: Arabidopsis thaliana

<400> SEQUENCE: 11

```
        Met Asn Gly Asp Glu Thr Lys Lys Val Glu Ser Glu Tyr Ile Lys Lys
        1               5                  10                 15
        His His Arg His Glu Leu Val Glu Ser Gln Cys Ser Ser Thr Leu Val
                        20                 25                 30
        Lys His Ile Lys Ala Pro Leu His Leu Val Trp Ser Ile Val Arg Arg
                        35                 40                 45
        Phe Asp Glu Pro Gln Lys Tyr Lys Pro Phe Ile Ser Arg Cys Val Val
                        50                 55                 60
        Gln Gly Lys Lys Leu Glu Val Gly Ser Val Arg Glu Val Asp Leu Lys
        65                 70                 75                 80
        Ser Gly Leu Pro Ala Thr Lys Ser Thr Glu Val Leu Glu Ile Leu Asp
                        85                 90                 95
        Asp Asn Glu His Ile Leu Gly Ile Arg Ile Val Gly Gly Asp His Arg
                        100                105                110
        Leu Lys Asn Tyr Ser Ser Thr Ile Ser Leu His Ser Glu Thr Ile Asp
                        115                120                125
        Gly Lys Thr Gly Thr Leu Ala Ile Glu Ser Phe Val Val Asp Val Pro
                        130                135                140
        Glu Gly Asn Thr Lys Glu Glu Thr Cys Phe Phe Val Glu Ala Leu Ile
        145                150                155                160
        Gln Cys Asn Leu Asn Ser Leu Ala Asp Val Thr Glu Arg Leu Gln Ala
                        165                170                175
        Glu Ser Met Glu Lys Lys Ile
                        180
```

<210> SEQ ID NO 12
<211> LENGTH: 161
<212> TYPE: PRT
<213> ORGANISM: Arabidopsis thaliana

<400> SEQUENCE: 12

```
Met Glu Thr Ser Gln Lys Tyr His Thr Cys Gly Ser Thr Leu Val Gln
1               5                   10                  15

Thr Ile Asp Ala Pro Leu Ser Leu Val Trp Ser Ile Leu Arg Arg Phe
            20                  25                  30

Asp Asn Pro Gln Ala Tyr Lys Gln Phe Val Lys Thr Cys Asn Leu Ser
        35                  40                  45

Ser Gly Asp Gly Gly Glu Gly Ser Val Arg Glu Val Thr Val Val Ser
    50                  55                  60

Gly Leu Pro Ala Glu Phe Ser Arg Glu Arg Leu Asp Glu Leu Asp Asp
65                  70                  75                  80

Glu Ser His Val Met Met Ile Ser Ile Ile Gly Gly Asp His Arg Leu
                85                  90                  95

Val Asn Tyr Arg Ser Lys Thr Met Ala Phe Val Ala Ala Asp Thr Glu
            100                 105                 110

Glu Lys Thr Val Val Val Glu Ser Tyr Val Val Asp Val Pro Glu Gly
        115                 120                 125

Asn Ser Glu Glu Glu Thr Thr Ser Phe Ala Asp Thr Ile Val Gly Phe
    130                 135                 140

Asn Leu Lys Ser Leu Ala Lys Leu Ser Glu Arg Val Ala His Leu Lys
145                 150                 155                 160

Leu
```

<210> SEQ ID NO 13
<211> LENGTH: 159
<212> TYPE: PRT
<213> ORGANISM: Arabidopsis thaliana

<400> SEQUENCE: 13

```
Met Lys Thr Ser Gln Glu Gln His Val Cys Gly Ser Thr Val Val Gln
1               5                   10                  15

Thr Ile Asn Ala Pro Leu Pro Leu Val Trp Ser Ile Leu Arg Arg Phe
            20                  25                  30

Asp Asn Pro Lys Thr Phe Lys His Phe Val Lys Thr Cys Lys Leu Arg
        35                  40                  45

Ser Gly Asp Gly Gly Glu Gly Ser Val Arg Glu Val Thr Val Val Ser
    50                  55                  60

Asp Leu Pro Ala Ser Phe Ser Leu Glu Arg Leu Asp Glu Leu Asp Asp
65                  70                  75                  80

Glu Ser His Val Met Val Ile Ser Ile Ile Gly Gly Asp His Arg Leu
                85                  90                  95

Val Asn Tyr Gln Ser Lys Thr Thr Val Phe Val Ala Ala Glu Glu Glu
            100                 105                 110

Lys Thr Val Val Val Glu Ser Tyr Val Val Asp Val Pro Glu Gly Asn
        115                 120                 125

Thr Glu Glu Glu Thr Thr Leu Phe Ala Asp Thr Ile Val Gly Cys Asn
    130                 135                 140

Leu Arg Ser Leu Ala Lys Leu Ser Glu Lys Met Met Glu Leu Thr
145                 150                 155
```

```
<210> SEQ ID NO 14
<211> LENGTH: 164
<212> TYPE: PRT
<213> ORGANISM: Arabidopsis thaliana

<400> SEQUENCE: 14

Met Glu Ser Ser Lys Gln Lys Arg Cys Arg Ser Ser Val Val Glu Thr
1               5                   10                  15

Ile Glu Ala Pro Leu Pro Leu Val Trp Ser Ile Leu Arg Ser Phe Asp
            20                  25                  30

Lys Pro Gln Ala Tyr Gln Arg Phe Val Lys Ser Cys Thr Met Arg Ser
        35                  40                  45

Gly Gly Gly Gly Lys Gly Gly Glu Gly Lys Gly Ser Val Arg Asp
    50                  55                  60

Val Thr Leu Val Ser Gly Phe Pro Ala Asp Phe Ser Thr Glu Arg Leu
65                  70                  75                  80

Glu Glu Leu Asp Asp Glu Ser His Val Met Val Val Ser Ile Ile Gly
                85                  90                  95

Gly Asn His Arg Leu Val Asn Tyr Lys Ser Lys Thr Lys Val Val Ala
            100                 105                 110

Ser Pro Glu Asp Met Ala Lys Lys Thr Val Val Glu Ser Tyr Val
        115                 120                 125

Val Asp Val Pro Glu Gly Thr Ser Glu Glu Asp Thr Ile Phe Phe Val
130                 135                 140

Asp Asn Ile Ile Arg Tyr Asn Leu Thr Ser Leu Ala Lys Leu Thr Lys
145                 150                 155                 160

Lys Met Met Lys

<210> SEQ ID NO 15
<211> LENGTH: 191
<212> TYPE: PRT
<213> ORGANISM: Brassica oleracea

<400> SEQUENCE: 15

Met Pro Ser Gln Leu Thr Pro Glu Glu Arg Ser Glu Leu Ala Gln Ser
1               5                   10                  15

Ile Ala Glu Phe His Thr Tyr His Leu Gly Pro Gly Ser Cys Ser Ser
            20                  25                  30

Leu His Ala Gln Arg Ile His Ala Pro Pro Glu Ile Val Trp Ser Val
        35                  40                  45

Val Arg Arg Phe Asp Lys Pro Gln Thr Tyr Lys His Phe Ile Lys Ser
    50                  55                  60

Cys Ser Val Glu Asp Gly Phe Glu Met Arg Val Gly Cys Thr Arg Ala
65                  70                  75                  80

Val Asn Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Val His Arg
        115                 120                 125

Phe Glu Lys Glu Arg Arg Ile Trp Thr Val Val Leu Glu Ser Tyr Val
130                 135                 140

Val Asp Met Pro Glu Gly Asn Ser Glu Asp Thr Arg Met Phe Ala
145                 150                 155                 160

Asp Thr Val Val Lys Leu Asn Leu Gln Lys Leu Ala Thr Val Thr Glu
                165                 170                 175
```

```
Ala Met Ala Arg Asn Ala Gly Asp Gly Ser Gly Ala Gln Val Thr
            180                 185                 190

<210> SEQ ID NO 16
<211> LENGTH: 281
<212> TYPE: PRT
<213> ORGANISM: Brassica oleracea

<400> SEQUENCE: 16

Met Pro Ser Glu Leu Thr Gln Glu Arg Ser Lys Leu Thr Gln Ser
1               5                   10                  15

Ile Ser Glu Phe His Thr Tyr His Leu Gly Pro Gly Ser Cys Ser Ser
            20                  25                  30

Leu His Ala Gln Arg Ile His Ala Pro Pro Glu Ile Val Trp Ser Val
            35                  40                  45

Val Arg Gln Phe Asp Lys Pro Gln Thr Tyr Lys His Phe Ile Lys Ser
        50                  55                  60

Cys Ser Val Glu Glu Gly Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Met Leu Asp Asp Glu Arg Arg Val Thr Gly Phe Ser Ile Ile Gly
            100                 105                 110

Gly Glu His Arg Leu Lys Asn Tyr Lys Ser Val Thr Thr Val His Arg
            115                 120                 125

Phe Glu Arg Glu Arg Arg Ile Trp Thr Val Val Leu Glu Ser Tyr Val
130                 135                 140

Val Asp Met Pro Glu Gly Asn Ser Glu Asp Thr Arg Met Phe Ala
145                 150                 155                 160

Asp Thr Val Val Lys Leu Asn Leu Gln Lys Leu Ala Thr Val Thr Glu
                165                 170                 175

Ala Met Ala Arg Asn Ala Gly Asp Gly Arg Gly Ser Arg Glu Thr Thr
            180                 185                 190

Cys Arg Glu Ser Phe His Leu Ile Thr Ala Phe Glu Lys Gln Arg Gln
            195                 200                 205

Ile Thr Glu Pro Thr Val Tyr Gln Asn Pro Pro Tyr His Thr Gly Met
        210                 215                 220

Thr Pro Glu Pro Arg Thr Ser Thr Val Phe Ile Glu Leu Glu Asp His
225                 230                 235                 240

Arg Thr Leu Pro Gly Asn Leu Thr Pro Thr Thr Glu Glu His Leu Gln
                245                 250                 255

Arg Met Tyr Gln Arg Phe Trp Gly Ile Arg Gln Leu Gly Arg Pro Arg
            260                 265                 270

Gln Ser Phe Gly Glu Arg Gln Ser Ile
            275                 280

<210> SEQ ID NO 17
<211> LENGTH: 453
<212> TYPE: PRT
<213> ORGANISM: Vitis vinifera

<400> SEQUENCE: 17

Met Gln Met Lys Tyr Leu Glu Gly Lys Gln Asn Leu Met Glu Glu Lys
1               5                   10                  15

Gly Glu Lys Gln Cys Ile Pro Met Asp Leu Ala Val Arg Glu Ala Gln
            20                  25                  30
```

```
Phe Lys Gly Ser Leu Leu Asp Arg Ile Thr Trp Leu Glu Gln Arg Leu
        35                  40                  45

His Lys Leu Ser Leu Gln Leu Glu Thr Arg Ser Lys Gln Gln Pro His
 50                  55                  60

Pro Ser Arg Met Gln Thr Ala Gly Glu Thr Ser Ser Arg His Gly Pro
 65              70                  75                  80

Lys Lys Glu Leu Ser Cys Ser Phe Pro Val Phe Ser Thr Arg Asn His
                 85                  90                  95

Asn His Gly His Lys Gln Thr Ser Gln Phe His Val Pro Arg Phe Glu
            100                 105                 110

Tyr Gln Glu Gly Gly Arg Glu Asn Pro Ala Val Val Ile Thr Lys Leu
        115                 120                 125

Thr Pro Phe His His Pro Lys Ile Ile Thr Ile Leu Phe Pro Ile Ser
    130                 135                 140

Asn Tyr Phe Ile Ile Phe Phe Phe Leu Thr Phe Asp Thr Lys Lys Gln
145                 150                 155                 160

Tyr Pro Leu Leu Phe Pro Ile Leu Pro Ser Arg Phe Leu Pro Ile Ser
                165                 170                 175

His Leu Ile Thr Gln Glu Ile Glu Lys Tyr Lys Thr Ser Ser His Phe
            180                 185                 190

Ser Ser Pro Ala Ser Leu Phe Ala Ala Met Asn Lys Ala Glu Thr Ser
        195                 200                 205

Ser Met Ala Glu Ala Glu Ser Glu Asp Ser Glu Thr Thr Thr Pro Thr
    210                 215                 220

Thr His His Leu Thr Ile Pro Pro Gly Leu Thr Gln Pro Glu Phe Gln
225                 230                 235                 240

Glu Leu Ala His Ser Ile Ser Glu Phe His Thr Tyr Gln Val Gly Pro
                245                 250                 255

Gly Gln Cys Ser Ser Leu Leu Ala Gln Arg Val His Ala Pro Leu Pro
            260                 265                 270

Thr Val Trp Ser Val Val Arg Arg Phe Asp Lys Pro Gln Thr Tyr Lys
        275                 280                 285

His Phe Ile Lys Ser Cys His Val Glu Asp Gly Phe Glu Met Arg Val
    290                 295                 300

Gly Cys Leu Arg Asp Val Asn Val Ile Ser Gly Leu Pro Ala Glu Thr
305                 310                 315                 320

Ser Thr Glu Arg Leu Asp Ile Leu Asp Asp Glu Arg His Val Thr Gly
                325                 330                 335

Phe Ser Ile Ile Gly Gly Glu His Arg Leu Arg Asn Tyr Arg Ser Val
            340                 345                 350

Thr Thr Asn His Gly Gly Glu Ile Trp Thr Val Val Leu Glu Ser Tyr
        355                 360                 365

Val Val Asp Met Pro Glu Gly Asn Thr Glu Glu Asp Thr Arg Leu Phe
    370                 375                 380

Ala Asp Thr Val Val Lys Leu Asn Leu Gln Lys Leu Ala Ser Val Thr
385                 390                 395                 400

Glu Val Ser Gln Ser Cys Asn Tyr Pro Cys Gln Phe His Ile Ile Glu
                405                 410                 415

Asn Glu Asp Ile Gln Pro Glu Glu Met Asn Leu Gly Val Leu Thr Thr
            420                 425                 430

Ser Ile Glu Glu Gln Arg Lys Lys Lys Arg Val Val Ala Met Lys Asp
        435                 440                 445
```

Gly Ser Thr Ser Ser
        450

<210> SEQ ID NO 18
<211> LENGTH: 195
<212> TYPE: PRT
<213> ORGANISM: Vitis vinifera
<220> FEATURE:
<221> NAME/KEY: misc_feature
<222> LOCATION: (193)..(193)
<223> OTHER INFORMATION: Xaa can be any naturally occurring amino acid

<400> SEQUENCE: 18

Met Ala Glu Ala Glu Ser Glu Asp Ser Glu Thr Thr Thr Pro Thr Thr
1               5                   10                  15

His His Leu Thr Ile Pro Pro Gly Leu Thr Gln Pro Glu Phe Gln Glu
            20                  25                  30

Leu Ala His Ser Ile Ser Glu Phe His Thr Tyr Gln Val Gly Pro Gly
        35                  40                  45

Gln Cys Ser Ser Leu Leu Ala Gln Arg Val His Ala Pro Leu Pro Thr
    50                  55                  60

Val Trp Ser Val Val Arg Arg Phe Asp Lys Pro Gln Thr Tyr Lys His
65                  70                  75                  80

Phe Ile Lys Ser Cys His Val Glu Asp Gly Phe Glu Met Arg Val Gly
                85                  90                  95

Cys Leu Arg Asp Val Asn Val Ile Ser Gly Leu Pro Ala Glu Thr Ser
            100                 105                 110

Thr Glu Arg Leu Asp Ile Leu Asp Asp Glu Arg His Val Thr Gly Phe
        115                 120                 125

Ser Ile Ile Gly Gly Glu His Arg Leu Arg Asn Tyr Arg Ser Val Thr
    130                 135                 140

Thr Val His Glu Tyr Gln Asn His Gly Gly Glu Ile Trp Thr Val Val
145                 150                 155                 160

Leu Glu Ser Tyr Val Val Asp Met Pro Glu Gly Asn Thr Glu Glu Asp
                165                 170                 175

Thr Arg Leu Phe Ala Asp Thr Val Val Lys Leu Asn Leu Ser Glu Ala
            180                 185                 190

Xaa Arg Arg
    195

<210> SEQ ID NO 19
<211> LENGTH: 217
<212> TYPE: PRT
<213> ORGANISM: Medicago truncatula

<400> SEQUENCE: 19

Met Glu Lys Ala Glu Ser Ser Thr Ala Ser Thr Ser Asp Gln Asp Ser
1               5                   10                  15

Asp Glu Asn His Arg Thr Gln His His Leu Thr Leu Pro Ser Gly Leu
            20                  25                  30

Arg Gln His Glu Phe Asp Ser Leu Ile Pro Phe Ile Asn Ser His His
        35                  40                  45

Thr Tyr Leu Ile Gly Pro Asn Gln Cys Ser Thr Leu Leu Ala Gln Arg
    50                  55                  60

Ile His Ala Pro Pro Gln Thr Val Trp Ser Val Val Arg Ser Phe Asp
65                  70                  75                  80

Lys Pro Gln Ile Tyr Lys His Ile Ile Lys Ser Cys Ser Leu Lys Glu
                85                  90                  95

```
Gly Phe Gln Met Lys Val Gly Cys Thr Arg Asp Val Asn Val Ile Ser
                100                 105                 110

Gly Leu Pro Ala Ala Thr Ser Thr Glu Arg Leu Asp Val Leu Asp Asp
            115                 120                 125

Glu Arg Arg Val Thr Gly Phe Ser Ile Ile Gly Gly Glu His Arg Leu
130                 135                 140

Lys Asn Tyr Arg Ser Val Thr Ser Val His Gly Phe Gly Asp Gly Asp
145                 150                 155                 160

Asn Gly Gly Glu Ile Trp Thr Val Val Leu Glu Ser Tyr Val Val Asp
                165                 170                 175

Val Pro Glu Gly Asn Thr Glu Glu Asp Thr Arg Leu Phe Ala Asp Thr
            180                 185                 190

Val Val Lys Leu Asn Leu Gln Lys Leu Ala Ser Val Thr Glu Gly Lys
            195                 200                 205

Asn Arg Asp Gly Asp Gly Lys Ser His
    210                 215

<210> SEQ ID NO 20
<211> LENGTH: 212
<212> TYPE: PRT
<213> ORGANISM: Oryza sativa

<400> SEQUENCE: 20

Met Glu Gln Gln Glu Val Pro Pro Pro Ala Gly Leu Gly Leu
1               5                   10                  15

Thr Ala Glu Glu Tyr Ala Gln Val Arg Ala Thr Val Glu Ala His His
            20                  25                  30

Arg Tyr Ala Val Gly Pro Gly Gln Cys Ser Ser Leu Leu Ala Gln Arg
        35                  40                  45

Ile His Ala Pro Pro Ala Ala Val Trp Ala Val Val Arg Arg Phe Asp
    50                  55                  60

Cys Pro Gln Val Tyr Lys His Phe Ile Arg Ser Cys Val Leu Arg Pro
65                  70                  75                  80

Asp Pro His His Asp Asp Asn Gly Asn Asp Leu Arg Pro Gly Arg Leu
                85                  90                  95

Arg Glu Val Ser Val Ile Ser Gly Leu Pro Ala Ser Thr Ser Thr Glu
            100                 105                 110

Arg Leu Asp Leu Leu Asp Asp Ala His Arg Val Phe Gly Phe Thr Ile
            115                 120                 125

Thr Gly Gly Glu His Arg Leu Arg Asn Tyr Arg Ser Val Thr Thr Val
        130                 135                 140

Ser Gln Leu Asp Glu Ile Cys Thr Leu Val Leu Glu Ser Tyr Ile Val
145                 150                 155                 160

Asp Val Pro Asp Gly Asn Thr Glu Asp Thr Arg Leu Phe Ala Asp
                165                 170                 175

Thr Val Ile Arg Leu Asn Leu Gln Lys Leu Lys Ser Val Ser Glu Ala
            180                 185                 190

Asn Ala Asn Ala Ala Ala Ala Ala Ala Pro Pro Pro Pro Pro Pro
            195                 200                 205

Ala Ala Ala Glu
    210

<210> SEQ ID NO 21
<211> LENGTH: 212
<212> TYPE: PRT
```

```
<213> ORGANISM: Zea mays

<400> SEQUENCE: 21

Met Asp Gln Gln Gly Ala Gly Gly Asp Ala Glu Val Pro Ala Gly Leu
1               5                   10                  15

Gly Leu Thr Ala Ala Glu Tyr Glu Gln Leu Arg Ser Thr Val Asp Ala
            20                  25                  30

His His Arg Tyr Ala Val Gly Glu Gly Gln Cys Ser Ser Leu Leu Ala
        35                  40                  45

Gln Arg Ile His Ala Pro Pro Glu Ala Val Trp Ala Val Val Arg Arg
    50                  55                  60

Phe Asp Cys Pro Gln Val Tyr Lys His Phe Ile Arg Ser Cys Ala Leu
65                  70                  75                  80

Arg Pro Asp Pro Glu Ala Gly Asp Ala Leu Cys Pro Gly Arg Leu Arg
                85                  90                  95

Glu Val Ser Val Ile Ser Gly Leu Pro Ala Ser Thr Ser Thr Glu Arg
            100                 105                 110

Leu Asp Leu Leu Asp Asp Ala Ala Arg Val Phe Gly Phe Ser Ile Thr
        115                 120                 125

Gly Gly Glu His Arg Leu Arg Asn Tyr Arg Ser Val Thr Thr Val Ser
    130                 135                 140

Glu Leu Ala Val Pro Ala Ile Cys Thr Val Val Leu Glu Ser Tyr Val
145                 150                 155                 160

Val Asp Val Pro Asp Gly Asn Thr Glu Asp Thr Arg Leu Phe Ala
                165                 170                 175

Asp Thr Val Ile Arg Leu Asn Leu Gln Lys Leu Lys Ser Val Ala Glu
        180                 185                 190

Ala Asn Ala Ala Glu Ala Ala Ala Thr Thr Asn Ser Val Leu Leu Pro
    195                 200                 205

Arg Pro Ala Glu
    210

<210> SEQ ID NO 22
<211> LENGTH: 212
<212> TYPE: PRT
<213> ORGANISM: Zea mays
<220> FEATURE:
<221> NAME/KEY: misc_feature
<222> LOCATION: (11)..(11)
<223> OTHER INFORMATION: Xaa can be any naturally occurring amino acid

<400> SEQUENCE: 22

Met Asp Gln Gln Gly Ala Gly Gly Asp Ala Xaa Val Pro Ala Gly Leu
1               5                   10                  15

Gly Leu Thr Ala Ala Glu Tyr Glu Gln Leu Arg Ser Thr Val Asp Ala
            20                  25                  30

His His Arg Tyr Ala Val Gly Glu Gly Gln Cys Ser Ser Leu Leu Ala
        35                  40                  45

Gln Arg Ile His Ala Pro Pro Glu Ala Val Trp Ala Val Val Arg Arg
    50                  55                  60

Phe Asp Cys Pro Gln Val Tyr Lys His Phe Ile Arg Ser Cys Ala Leu
65                  70                  75                  80

Arg Pro Asp Pro Glu Ala Gly Asp Ala Leu Cys Pro Gly Arg Leu Arg
                85                  90                  95

Glu Val Ser Val Ile Ser Gly Leu Pro Ala Ser Thr Ser Thr Glu Arg
            100                 105                 110
```

Leu Asp Leu Asp Asp Ala Ala Arg Val Phe Gly Phe Ser Ile Thr
            115                 120                 125

Gly Gly Glu His Arg Leu Arg Asn Tyr Arg Ser Val Thr Thr Val Ser
130                 135                 140

Glu Leu Ala Asp Pro Ala Ile Cys Thr Val Val Leu Glu Ser Tyr Val
145                 150                 155                 160

Val Asp Val Pro Asp Gly Asn Thr Glu Asp Thr Arg Leu Phe Ala
            165                 170                 175

Asp Thr Val Ile Arg Leu Asn Leu Gln Lys Leu Lys Ser Val Thr Glu
            180                 185                 190

Ala Asn Ala Ala Glu Ala Ala Ala Thr Thr Asn Ser Val Leu Leu Pro
            195                 200                 205

Arg Pro Ala Glu
        210

<210> SEQ ID NO 23
<211> LENGTH: 233
<212> TYPE: PRT
<213> ORGANISM: Vitis vinifera

<400> SEQUENCE: 23

Met Asp Pro His His His Gly Leu Thr Glu Glu Glu Phe Arg Ala
1               5                   10                  15

Leu Glu Pro Ile Ile Gln Asn Tyr His Thr Phe Glu Pro Ser Pro Asn
            20                  25                  30

Thr Cys Thr Ser Leu Ile Thr Gln Lys Ile Asp Ala Pro Ala Gln Val
            35                  40                  45

Val Trp Pro Phe Val Arg Ser Phe Glu Asn Pro Gln Lys Tyr Lys His
50                  55                  60

Phe Ile Lys Asp Cys Thr Met Arg Gly Asp Gly Val Gly Ser Ile
65                  70                  75                  80

Arg Glu Val Thr Val Val Ser Gly Leu Pro Ala Ser Thr Ser Thr Glu
            85                  90                  95

Arg Leu Glu Ile Leu Asp Asp Glu Lys His Ile Leu Ser Phe Arg Val
            100                 105                 110

Val Gly Gly Glu His Arg Leu Asn Asn Tyr Arg Ser Val Thr Ser Val
            115                 120                 125

Asn Asp Phe Ser Lys Glu Gly Lys Asp Tyr Thr Ile Val Leu Glu Ser
            130                 135                 140

Tyr Ile Val Asp Ile Pro Glu Gly Asn Thr Gly Glu Asp Thr Lys Met
145                 150                 155                 160

Phe Val Asp Thr Val Val Lys Leu Asn Leu Gln Lys Leu Ala Val Val
            165                 170                 175

Ala Ile Thr Ser Leu His Glu Asn Glu Ile Ala Asp Asn Glu Gly
            180                 185                 190

Pro Ser Arg Glu Ile Ser Leu Gln Ser Glu Thr Glu Ser Ala Glu Arg
            195                 200                 205

Gly Asp Glu Arg Arg Asp Gly Asp Gly Pro Ser Lys Ala Cys Asn Arg
            210                 215                 220

Asn Glu Trp His Cys Thr Thr Lys Glu
225                 230

<210> SEQ ID NO 24
<211> LENGTH: 207
<212> TYPE: PRT
<213> ORGANISM: Oryza sativa

<400> SEQUENCE: 24

```
Met Glu Pro His Met Glu Arg Ala Leu Arg Glu Ala Val Ala Ser Glu
1               5                   10                  15

Ala Glu Arg Arg Glu Leu Glu Gly Val Val Arg Ala His His Thr Phe
            20                  25                  30

Pro Ala Ala Glu Arg Ala Ala Gly Pro Gly Arg Arg Pro Thr Cys Thr
        35                  40                  45

Ser Leu Val Ala Gln Arg Val Asp Ala Pro Leu Ala Ala Val Trp Pro
    50                  55                  60

Ile Val Arg Gly Phe Ala Asn Pro Gln Arg Tyr Lys His Phe Ile Lys
65                  70                  75                  80

Ser Cys Glu Leu Ala Ala Gly Asp Gly Ala Thr Val Gly Ser Val Arg
                85                  90                  95

Glu Val Ala Val Val Ser Gly Leu Pro Ala Ser Thr Ser Thr Glu Arg
            100                 105                 110

Leu Glu Ile Leu Asp Asp Asp Arg His Val Leu Ser Phe Arg Val Val
            115                 120                 125

Gly Gly Asp His Arg Leu Arg Asn Tyr Arg Ser Val Thr Ser Val Thr
        130                 135                 140

Glu Phe Ser Ser Pro Ser Ser Pro Pro Arg Pro Tyr Cys Val Val Val
145                 150                 155                 160

Glu Ser Tyr Val Val Asp Val Pro Glu Gly Asn Thr Glu Glu Asp Thr
                165                 170                 175

Arg Met Phe Thr Asp Thr Val Val Lys Leu Asn Leu Gln Lys Leu Ala
            180                 185                 190

Ala Val Ala Thr Ser Ser Ser Pro Pro Ala Ala Gly Asn His His
            195                 200                 205
```

<210> SEQ ID NO 25
<211> LENGTH: 210
<212> TYPE: PRT
<213> ORGANISM: Oryza sativa

<400> SEQUENCE: 25

```
Met Glu Pro His Met Glu Arg Ala Leu Arg Glu Ala Val Ala Ser Glu
1               5                   10                  15

Ala Glu Arg Arg Glu Leu Glu Gly Val Val Arg Ala His His Thr Phe
            20                  25                  30

Pro Ala Ala Glu Arg Ala Ala Gly Pro Gly Arg Arg Pro Thr Cys Thr
        35                  40                  45

Ser Leu Val Ala Gln Arg Val Asp Ala Pro Leu Ala Ala Val Trp Pro
    50                  55                  60

Ile Val Arg Gly Phe Ala Asn Pro Gln Arg Tyr Lys His Phe Ile Lys
65                  70                  75                  80

Ser Cys Glu Leu Ala Ala Gly Asp Gly Ala Thr Val Gly Ser Val Arg
                85                  90                  95

Glu Val Ala Val Val Ser Gly Leu Pro Ala Ser Thr Ser Thr Glu Arg
            100                 105                 110

Leu Glu Ile Leu Asp Asp Asp Arg His Val Leu Ser Phe Arg Val Val
            115                 120                 125

Gly Gly Asp His Arg Leu Arg Asn Tyr Arg Ser Val Thr Ser Val Thr
        130                 135                 140

Glu Phe Ser Ser Pro Ser Ser Pro Pro Arg Pro Tyr Cys
145                 150                 155                 160
```

```
Val Val Val Glu Ser Tyr Val Asp Val Pro Gly Asn Thr Glu
            165                 170                 175

Glu Asp Thr Arg Met Phe Thr Asp Thr Val Val Lys Leu Asn Leu Gln
            180                 185                 190

Lys Leu Ala Ala Val Ala Thr Ser Ser Ser Pro Ala Ala Gly Asn
            195                 200                 205

His His
   210

<210> SEQ ID NO 26
<211> LENGTH: 200
<212> TYPE: PRT
<213> ORGANISM: Zea mays

<400> SEQUENCE: 26

Met Pro Tyr Thr Ala Pro Arg Pro Ser Pro Gln Gln His Ser Arg Val
1               5                   10                  15

Leu Ser Gly Gly Gly Ala Lys Ala Ala Ser His Gly Ala Ser Cys Ala
            20                  25                  30

Ala Val Pro Ala Glu Val Ala Arg His His Glu His Ala Ala Arg Ala
            35                  40                  45

Gly Gln Cys Cys Ser Ala Val Val Gln Ala Ile Ala Ala Pro Val Gly
    50                  55                  60

Ala Val Trp Ser Val Val Arg Arg Phe Asp Arg Pro Gln Ala Tyr Lys
65                  70                  75                  80

His Phe Ile Arg Ser Cys Arg Leu Val Gly Gly Gly Asp Val Ala Val
                85                  90                  95

Gly Ser Val Arg Glu Val Arg Val Val Ser Gly Leu Pro Ala Thr Ser
            100                 105                 110

Ser Arg Glu Arg Leu Glu Ile Leu Asp Asp Glu Arg Arg Val Leu Ser
            115                 120                 125

Phe Arg Val Val Gly Gly Glu His Arg Leu Ala Asn Tyr Arg Ser Val
    130                 135                 140

Thr Thr Val His Glu Ala Gly Ala Gly Ala Gly Thr Gly Thr Val Val
145                 150                 155                 160

Val Glu Ser Tyr Val Val Asp Val Pro His Gly Asn Thr Ala Asp Glu
                165                 170                 175

Thr Arg Val Phe Val Asp Thr Ile Val Arg Cys Asn Leu Gln Ser Leu
            180                 185                 190

Ala Arg Thr Ala Glu Arg Leu Ala
            195                 200

<210> SEQ ID NO 27
<211> LENGTH: 215
<212> TYPE: PRT
<213> ORGANISM: Vitis vinifera

<400> SEQUENCE: 27

Met Pro Ser Asn Pro Lys Ser Ser Leu Val Val His Arg Ile Asn
1               5                   10                  15

Ser Pro Asn Ser Ile Thr Thr Ala Thr Thr Ala Ser Ala Ala Ala Asn
            20                  25                  30

Asn His Asn Thr Ser Thr Met Pro Pro His Lys Gln Val Pro Asp Ala
            35                  40                  45

Val Ser Arg His His Thr His Val Val Gly Pro Asn Gln Cys Cys Ser
    50                  55                  60
```

```
Ala Val Val Gln Gln Ile Ala Ala Pro Val Ser Thr Val Trp Ser Val
 65                  70                  75                  80

Val Arg Arg Phe Asp Asn Pro Gln Ala Tyr Lys His Phe Val Lys Ser
                 85                  90                  95

Cys His Val Val Val Gly Asp Gly Asp Val Gly Thr Leu Arg Glu Val
                100                 105                 110

His Val Ile Ser Gly Leu Pro Ala Ala Asn Ser Thr Glu Arg Leu Glu
            115                 120                 125

Ile Leu Asp Asp Glu Arg His Val Leu Ser Phe Ser Val Ile Gly Gly
        130                 135                 140

Asp His Arg Leu Ser Asn Tyr Arg Ser Val Thr Thr Leu His Pro Ser
145                 150                 155                 160

Pro Ser Ser Thr Gly Thr Val Val Leu Glu Ser Tyr Val Val Asp Ile
                165                 170                 175

Pro Pro Gly Asn Thr Lys Glu Asp Thr Cys Val Phe Val Asp Thr Ile
            180                 185                 190

Val Arg Cys Asn Leu Gln Ser Leu Ala Gln Ile Ala Glu Asn Ala Ala
        195                 200                 205

Gly Cys Lys Arg Ser Ser
210                 215

<210> SEQ ID NO 28
<211> LENGTH: 213
<212> TYPE: PRT
<213> ORGANISM: Nicotiana tabacum

<400> SEQUENCE: 28

Met Pro Pro Ser Ser Pro Asp Ser Ser Val Leu Leu Gln Arg Ile Ser
 1               5                  10                  15

Ser Asn Thr Thr Pro Asp Phe Ala Cys Lys Gln Ser Gln Gln Leu Gln
                 20                  25                  30

Arg Arg Thr Met Pro Ile Pro Cys Thr Thr Gln Val Pro Asp Ser Val
             35                  40                  45

Val Arg Phe His Thr His Pro Val Gly Pro Asn Gln Cys Cys Ser Ala
 50                  55                  60

Val Ile Gln Arg Ile Ser Ala Pro Val Ser Thr Val Trp Ser Val Val
 65                  70                  75                  80

Arg Arg Phe Asp Asn Pro Gln Ala Tyr Lys His Phe Val Lys Ser Cys
                 85                  90                  95

His Val Val Val Gly Asp Gly Asp Val Gly Thr Leu Arg Glu Val Arg
                100                 105                 110

Val Ile Ser Gly Leu Pro Ala Ala Ser Ser Thr Glu Arg Leu Glu Ile
            115                 120                 125

Leu Asp Asp Glu Arg His Val Ile Ser Phe Ser Val Val Gly Gly Asp
        130                 135                 140

His Arg Leu Ala Asn Tyr Arg Ser Val Thr Thr Leu His Pro Glu Pro
145                 150                 155                 160

Ser Gly Asp Gly Thr Thr Ile Val Val Glu Ser Tyr Val Val Asp Val
                165                 170                 175

Pro Pro Gly Asn Thr Arg Asp Glu Thr Cys Val Phe Val Asp Thr Ile
            180                 185                 190

Val Lys Cys Asn Leu Thr Ser Leu Ser Gln Ile Ala Val Asn Val Asn
        195                 200                 205

Arg Arg Lys Asp Ser
```

<210> SEQ ID NO 29
<211> LENGTH: 208
<212> TYPE: PRT
<213> ORGANISM: Oryza sativa

<400> SEQUENCE: 29

Met Pro Tyr Ala Ala Val Arg Pro Ser Pro Pro Gln Leu Ser Arg
1               5                   10                  15

Pro Ile Gly Ser Gly Ala Gly Gly Lys Ala Cys Pro Ala Val Pro
                20                  25                  30

Cys Glu Val Ala Arg Tyr His Glu His Ala Val Gly Ala Gly Gln Cys
                35                  40                  45

Cys Ser Thr Val Val Gln Ala Ile Ala Ala Pro Ala Asp Ala Val Trp
50                      55                  60

Ser Val Val Arg Arg Phe Asp Arg Pro Gln Ala Tyr Lys Lys Phe Ile
65                      70                  75                  80

Lys Ser Cys Arg Leu Val Asp Gly Asp Gly Gly Glu Val Gly Ser Val
                85                  90                  95

Arg Glu Val Arg Val Val Ser Gly Leu Pro Ala Thr Ser Ser Arg Glu
                100                 105                 110

Arg Leu Glu Val Leu Asp Asp Arg Arg Val Leu Ser Phe Arg Ile
                115                 120                 125

Val Gly Gly Glu His Arg Leu Ala Asn Tyr Arg Ser Val Thr Thr Val
                130                 135                 140

His Glu Ala Ala Ala Pro Ala Met Ala Val Val Glu Ser Tyr Val
145                 150                 155                 160

Val Asp Val Pro Pro Gly Asn Thr Trp Glu Glu Thr Arg Val Phe Val
                165                 170                 175

Asp Thr Ile Val Arg Cys Asn Leu Gln Ser Leu Ala Arg Thr Val Glu
                180                 185                 190

Arg Leu Ala Pro Glu Ala Pro Arg Ala Asn Gly Ser Ile Asp His Ala
                195                 200                 205

<210> SEQ ID NO 30
<211> LENGTH: 208
<212> TYPE: PRT
<213> ORGANISM: Oryza sativa

<400> SEQUENCE: 30

Met Pro Tyr Ala Ala Val Arg Pro Ser Pro Pro Gln Leu Ser Arg
1               5                   10                  15

Pro Ile Gly Ser Gly Ala Gly Gly Lys Ala Cys Pro Ala Val Pro
                20                  25                  30

Cys Glu Val Ala Arg Tyr His Glu His Ala Val Gly Ala Gly Gln Cys
                35                  40                  45

Phe Ser Thr Val Val Gln Ala Ile Ala Ala Pro Ala Asp Ala Val Trp
                50                  55                  60

Ser Val Val Arg Arg Phe Asp Arg Pro Gln Ala Tyr Lys Lys Phe Ile
65                      70                  75                  80

Lys Ser Cys Arg Leu Val Asp Gly Asp Gly Gly Glu Val Gly Ser Val
                85                  90                  95

Arg Glu Val Arg Val Val Ser Gly Leu Pro Ala Thr Ser Ser Arg Glu
                100                 105                 110

Arg Leu Glu Val Leu Asp Asp Asp Arg Arg Val Leu Ser Phe Arg Ile

```
                115                 120                 125
Val Gly Gly Glu His Arg Leu Ala Asn Tyr Arg Ser Val Thr Thr Val
        130                 135                 140
His Glu Ala Ala Ala Pro Ala Met Ala Val Val Glu Ser Tyr Val
145                 150                 155                 160
Val Asp Val Pro Pro Gly Asn Thr Trp Glu Thr Arg Val Phe Val
                165                 170                 175
Asp Thr Ile Val Arg Cys Asn Leu Gln Ser Leu Ala Arg Thr Val Glu
            180                 185                 190
Arg Leu Ala Pro Glu Ala Pro Arg Ala Asn Gly Ser Ile Asp His Ala
        195                 200                 205

<210> SEQ ID NO 31
<211> LENGTH: 213
<212> TYPE: PRT
<213> ORGANISM: Picea sitchensis

<400> SEQUENCE: 31

Met Asp Ile Ile Ala Gly Phe Asp Gln Leu Ser Phe Arg Leu Ser Gly
1               5                   10                  15
Ala Ser Lys Gln Ile Thr Lys Thr Gly Ala Val Gln Tyr Leu Lys Gly
            20                  25                  30
Glu Glu Gly Tyr Gly Glu Trp Leu Lys Glu Val Met Gly Arg Tyr His
        35                  40                  45
Tyr His Ser His Asp Gly Ala Arg Glu Cys Arg Cys Ser Ser Val Val
    50                  55                  60
Val Gln Gln Val Glu Ala Pro Val Ser Val Val Trp Ser Leu Val Arg
65                  70                  75                  80
Arg Phe Asp Gln Pro Gln Val Tyr Lys His Phe Val Ser Asn Cys Phe
                85                  90                  95
Met Arg Gly Asp Leu Lys Val Gly Cys Leu Arg Glu Val Arg Val Val
            100                 105                 110
Ser Gly Leu Pro Ala Ala Thr Ser Thr Glu Arg Leu Asp Ile Leu Asp
        115                 120                 125
Glu Glu Arg His Ile Leu Ser Phe Ser Ile Val Gly Gly Asp His Arg
    130                 135                 140
Leu Asn Asn Tyr Arg Ser Ile Thr Thr Leu His Glu Thr Leu Ile Asn
145                 150                 155                 160
Gly Lys Pro Gly Thr Ile Val Ile Glu Ser Tyr Val Leu Asp Val Pro
                165                 170                 175
His Gly Asn Thr Lys Glu Glu Thr Cys Leu Phe Val Asp Thr Ile Val
            180                 185                 190
Lys Cys Asn Leu Gln Ser Leu Ala His Val Ser Asn His Leu Asn Ser
        195                 200                 205
Thr His Arg Cys Leu
    210

<210> SEQ ID NO 32
<211> LENGTH: 207
<212> TYPE: PRT
<213> ORGANISM: Oryza sativa

<400> SEQUENCE: 32

Met Glu Ala His Val Glu Arg Ala Leu Arg Glu Gly Leu Thr Glu Glu
1               5                   10                  15
Glu Arg Ala Ala Leu Glu Pro Ala Val Met Ala His His Thr Phe Pro
```

```
                 20                  25                  30
Pro Ser Thr Thr Thr Ala Thr Ala Ala Ala Thr Cys Thr Ser Leu
             35                  40                  45

Val Thr Gln Arg Val Ala Ala Pro Val Arg Ala Val Trp Pro Ile Val
         50                  55                  60

Arg Ser Phe Gly Asn Pro Gln Arg Tyr Lys His Phe Val Arg Thr Cys
65                  70                  75                  80

Ala Leu Ala Ala Gly Asp Gly Ala Ser Val Gly Ser Val Arg Glu Val
                 85                  90                  95

Thr Val Val Ser Gly Leu Pro Ala Ser Thr Ser Thr Glu Arg Leu Glu
             100                 105                 110

Met Leu Asp Asp Asp Arg His Ile Ile Ser Phe Arg Val Val Gly Gly
             115                 120                 125

Gln His Arg Leu Arg Asn Tyr Arg Ser Val Thr Ser Val Thr Glu Phe
         130                 135                 140

Gln Pro Pro Ala Ala Gly Pro Gly Pro Ala Pro Pro Tyr Cys Val Val
145                 150                 155                 160

Val Glu Ser Tyr Val Val Asp Val Pro Asp Gly Asn Thr Ala Glu Asp
                 165                 170                 175

Thr Arg Met Phe Thr Asp Thr Val Val Lys Leu Asn Leu Gln Met Leu
             180                 185                 190

Ala Ala Val Ala Glu Asp Ser Ser Ala Ser Arg Arg Arg Asp
         195                 200                 205

<210> SEQ ID NO 33
<211> LENGTH: 216
<212> TYPE: PRT
<213> ORGANISM: Oryza sativa

<400> SEQUENCE: 33

Met Pro Tyr Thr Ala Pro Arg Pro Ser Pro Pro Gln His Ser Arg Ile
1               5                   10                  15

Gly Gly Cys Gly Gly Gly Gly Val Leu Lys Ala Ala Gly Ala Ala Gly
             20                  25                  30

His Ala Ala Ser Cys Val Ala Val Pro Ala Glu Val Ala Arg His His
         35                  40                  45

Glu His Ala Ala Gly Val Gly Gln Cys Cys Ser Ala Val Val Gln Ala
     50                  55                  60

Ile Ala Ala Pro Val Asp Ala Val Trp Ser Val Val Arg Arg Phe Asp
65                  70                  75                  80

Arg Pro Gln Ala Tyr Lys His Phe Ile Arg Ser Cys Arg Leu Leu Asp
                 85                  90                  95

Gly Asp Gly Asp Gly Gly Ala Val Ala Val Gly Ser Val Arg Glu Val
             100                 105                 110

Arg Val Val Ser Gly Leu Pro Ala Thr Ser Ser Arg Glu Arg Leu Glu
         115                 120                 125

Ile Leu Asp Asp Glu Arg Arg Val Leu Ser Phe Arg Val Val Gly Gly
     130                 135                 140

Glu His Arg Leu Ser Asn Tyr Arg Ser Val Thr Thr Val His Glu Thr
145                 150                 155                 160

Ala Ala Gly Ala Ala Ala Val Val Glu Ser Tyr Val Val Asp
                 165                 170                 175

Val Pro His Gly Asn Thr Ala Asp Glu Thr Arg Met Phe Val Asp Thr
             180                 185                 190
```

```
Ile Val Arg Cys Asn Leu Gln Ser Leu Ala Arg Thr Ala Glu Gln Leu
            195                 200                 205

Ala Leu Ala Ala Pro Arg Ala Ala
    210                 215

<210> SEQ ID NO 34
<211> LENGTH: 212
<212> TYPE: PRT
<213> ORGANISM: Vitis vinifera

<400> SEQUENCE: 34

Met Pro Ser Ser Leu Gln Leu His Arg Ile Asn Asn Ile Asp Pro Thr
1               5                   10                  15

Thr Val Ala Val Ala Ala Thr Ala Ala Val Asn Cys His Lys Gln Ser
            20                  25                  30

Arg Thr Pro Leu Arg Cys Ala Thr Pro Val Pro Asp Ala Val Ala Ser
        35                  40                  45

Tyr His Ala His Ala Val Gly Pro His Gln Cys Cys Ser Met Val Val
    50                  55                  60

Gln Thr Thr Ala Ala Ala Leu Pro Thr Val Trp Ser Val Val Arg Arg
65                  70                  75                  80

Phe Asp Asn Pro Gln Ala Tyr Lys His Phe Leu Lys Ser Cys His Val
                85                  90                  95

Ile Phe Gly Asp Gly Asp Ile Gly Thr Leu Arg Glu Val His Val Val
            100                 105                 110

Ser Gly Leu Pro Ala Glu Ser Ser Thr Glu Arg Leu Glu Ile Leu Asp
        115                 120                 125

Asp Glu Arg His Val Leu Ser Phe Ser Val Val Gly Gly Asp His Arg
    130                 135                 140

Leu Cys Asn Tyr Arg Ser Val Thr Thr Leu His Pro Ser Pro Thr Gly
145                 150                 155                 160

Thr Gly Thr Val Val Val Glu Ser Tyr Val Val Asp Ile Pro Pro Gly
                165                 170                 175

Asn Thr Lys Glu Asp Thr Cys Val Phe Val Asp Thr Ile Val Lys Cys
            180                 185                 190

Asn Leu Gln Ser Leu Ala Gln Met Ser Glu Lys Leu Thr Asn Asn Asn
        195                 200                 205

Arg Asn Ser Ser
    210

<210> SEQ ID NO 35
<211> LENGTH: 218
<212> TYPE: PRT
<213> ORGANISM: Zea mays

<400> SEQUENCE: 35

Met Pro Cys Leu Gln Ala Ser Ser Pro Gly Ser Met Pro Tyr Gln His
1               5                   10                  15

His Gly Arg Gly Val Gly Cys Ala Glu Ala Gly Ala Ala Val Gly
            20                  25                  30

Ala Ser Ala Gly Thr Gly Thr Arg Cys Gly Ala His Asp Gly Glu Val
        35                  40                  45

Pro Ala Glu Ala Ala Arg His His Glu His Ala Ala Pro Gly Pro Gly
    50                  55                  60

Arg Cys Cys Ser Ala Val Val Gln Arg Val Ala Ala Pro Ala Glu Ala
65                  70                  75                  80
```

Val Trp Ser Val Val Arg Arg Phe Asp Gln Pro Gln Ala Tyr Lys Arg
            85                  90                  95

Phe Val Arg Ser Cys Ala Leu Leu Ala Gly Asp Gly Val Gly Thr
        100                 105                 110

Leu Arg Glu Val Arg Val Val Ser Gly Leu Pro Ala Ala Ser Ser Arg
        115                 120                 125

Glu Arg Leu Glu Val Leu Asp Asp Glu Ser His Val Leu Ser Phe Arg
130                 135                 140

Val Val Gly Gly Glu His Arg Leu Gln Asn Tyr Leu Ser Val Thr Thr
145                 150                 155                 160

Val His Pro Ser Pro Ala Ala Pro Asp Ala Ala Thr Val Val Glu
                165                 170                 175

Ser Tyr Val Val Asp Val Pro Pro Gly Asn Thr Pro Glu Asp Thr Arg
            180                 185                 190

Val Phe Val Asp Thr Ile Val Lys Cys Asn Leu Gln Ser Leu Ala Thr
            195                 200                 205

Thr Ala Glu Lys Leu Ala Leu Ala Ala Val
        210                 215

<210> SEQ ID NO 36
<211> LENGTH: 179
<212> TYPE: PRT
<213> ORGANISM: Physcomitrella patens

<400> SEQUENCE: 36

Met Gln Thr Lys Gly Arg Gln Ala Asp Phe Gln Thr Leu Leu Glu Gly
1               5                   10                  15

Gln Gln Asp Leu Ile Cys Arg Phe His Arg His Glu Leu Gln Pro His
            20                  25                  30

Gln Cys Gly Ser Ile Leu Leu Gln Leu Ile Lys Ala Pro Val Glu Thr
        35                  40                  45

Val Trp Ser Val Ala Arg Ser Phe Asp Lys Pro Gln Val Tyr Lys Arg
    50                  55                  60

Phe Ile Gln Thr Cys Glu Ile Ile Gly Asp Gly Gly Val Gly Ser
65                  70                  75                  80

Ile Arg Glu Val Arg Leu Val Ser Ser Ile Pro Ala Thr Ser Ser Ile
                85                  90                  95

Glu Arg Leu Glu Ile Leu Asp Asp Glu Glu His Ile Ile Ser Phe Arg
            100                 105                 110

Val Leu Gly Gly Gly His Arg Leu Gln Asn Tyr Trp Ser Val Thr Ser
        115                 120                 125

Leu His Ser His Glu Ile Asp Gly Gln Met Gly Thr Leu Val Leu Glu
    130                 135                 140

Ser Tyr Val Val Asp Ile Pro Glu Gly Asn Thr Arg Glu Glu Thr His
145                 150                 155                 160

Met Phe Val Asp Thr Val Val Arg Cys Asn Leu Lys Ala Leu Ala Gln
                165                 170                 175

Val Ser Glu

<210> SEQ ID NO 37
<211> LENGTH: 229
<212> TYPE: PRT
<213> ORGANISM: Oryza sativa

<400> SEQUENCE: 37

Met Pro Cys Ile Pro Ala Ser Ser Pro Gly Ile Pro His Gln His Gln

```
              1               5                  10                 15
           His Gln His His Arg Ala Leu Ala Gly Val Gly Met Ala Val Gly Cys
                         20                 25                 30

Ala Ala Glu Ala Ala Val Ala Ala Ala Gly Val Ala Gly Thr Arg Cys
                         35                 40                 45

Gly Ala His Asp Gly Glu Val Pro Met Glu Val Ala Arg His His Glu
                         50                 55                 60

His Ala Glu Pro Gly Ser Gly Arg Cys Cys Ser Ala Val Val Gln His
           65                70                 75                 80

Val Ala Ala Pro Ala Pro Ala Val Trp Ser Val Val Arg Arg Phe Asp
                              85                 90                 95

Gln Pro Gln Ala Tyr Lys Arg Phe Val Arg Ser Cys Ala Leu Leu Ala
                             100                105                110

Gly Asp Gly Gly Val Gly Thr Leu Arg Glu Val Arg Val Val Ser Gly
                             115                120                125

Leu Pro Ala Ala Ser Ser Arg Glu Arg Leu Glu Ile Leu Asp Asp Glu
                     130                135                140

Ser His Val Leu Ser Phe Arg Val Val Gly Gly Glu His Arg Leu Lys
           145                150                155                160

Asn Tyr Leu Ser Val Thr Thr Val His Pro Ser Pro Ser Ala Pro Thr
                                  165                170                175

Ala Ala Thr Val Val Val Glu Ser Tyr Val Val Asp Val Pro Pro Gly
                             180                185                190

Asn Thr Pro Glu Asp Thr Arg Val Phe Val Asp Thr Ile Val Lys Cys
                             195                200                205

Asn Leu Gln Ser Leu Ala Lys Thr Ala Glu Lys Leu Ala Ala Gly Ala
                     210                215                220

Arg Ala Ala Gly Ser
           225

<210> SEQ ID NO 38
           <211> LENGTH: 229
           <212> TYPE: PRT
           <213> ORGANISM: Oryza sativa

<400> SEQUENCE: 38

Met Pro Cys Ile Pro Ala Ser Ser Pro Gly Ile Pro His Gln His Gln
           1               5                  10                 15

His Gln His His Arg Ala Leu Ala Gly Val Gly Met Ala Val Gly Cys
                         20                 25                 30

Ala Ala Glu Ala Ala Val Ala Ala Ala Gly Val Ala Gly Thr Arg Cys
                         35                 40                 45

Gly Ala His Asp Gly Glu Val Pro Met Glu Val Ala Arg His His Glu
                         50                 55                 60

His Ala Glu Pro Gly Ser Gly Arg Cys Cys Ser Ala Val Val Gln His
           65                70                 75                 80

Val Ala Ala Pro Ala Ala Val Trp Ser Val Val Arg Arg Phe Asp
                              85                 90                 95

Gln Pro Gln Ala Tyr Lys Arg Phe Val Arg Ser Cys Ala Leu Leu Ala
                             100                105                110

Gly Asp Gly Gly Val Gly Thr Leu Arg Glu Val Arg Val Val Ser Gly
                             115                120                125

Leu Pro Ala Ala Ser Ser Arg Glu Arg Leu Glu Ile Leu Asp Asp Glu
                     130                135                140
```

```
Ser His Val Leu Ser Phe Arg Val Val Gly Glu His Arg Leu Lys
145                 150                 155                 160

Asn Tyr Leu Ser Val Thr Thr Val His Pro Ser Pro Ser Ala Pro Thr
                165                 170                 175

Ala Ala Thr Val Val Val Glu Ser Tyr Val Val Asp Val Pro Pro Gly
            180                 185                 190

Asn Thr Pro Glu Asp Thr Arg Val Phe Val Asp Thr Ile Val Lys Cys
            195                 200                 205

Asn Leu Gln Ser Leu Ala Lys Thr Ala Glu Lys Leu Ala Ala Gly Ala
    210                 215                 220

Arg Ala Ala Gly Ser
225

<210> SEQ ID NO 39
<211> LENGTH: 205
<212> TYPE: PRT
<213> ORGANISM: Medicago truncatula

<400> SEQUENCE: 39

Met Pro Ser Pro Val Gln Phe Gln Arg Phe Asp Ser Asn Thr Ala Ile
1               5                   10                  15

Thr Asn Gly Val Asn Cys Pro Lys Gln Ile Gln Ala Cys Arg Tyr Ala
            20                  25                  30

Leu Ser Ser Leu Lys Pro Thr Val Ser Val Pro Glu Thr Val Val Asp
        35                  40                  45

His His Met His Val Val Gly Gln Asn Gln Cys Tyr Ser Val Val Ile
    50                  55                  60

Gln Thr Ile Asn Ala Ser Val Ser Thr Val Trp Ser Val Val Arg Arg
65                  70                  75                  80

Phe Asp Tyr Pro Gln Gly Tyr Lys His Phe Val Lys Ser Cys Asn Val
                85                  90                  95

Val Ala Ser Gly Asp Gly Ile Arg Val Gly Ala Leu Arg Glu Val Arg
            100                 105                 110

Leu Val Ser Gly Leu Pro Ala Val Ser Ser Thr Glu Arg Leu Asp Ile
        115                 120                 125

Leu Asp Glu Glu Arg His Val Ile Ser Phe Ser Val Val Gly Gly Val
    130                 135                 140

His Arg Cys Arg Asn Tyr Arg Ser Val Thr Thr Leu His Gly Asp Gly
145                 150                 155                 160

Asn Gly Gly Thr Val Val Ile Glu Ser Tyr Val Val Asp Val Pro Gln
                165                 170                 175

Gly Asn Thr Lys Glu Glu Thr Cys Ser Phe Ala Asp Thr Ile Val Arg
            180                 185                 190

Cys Asn Leu Gln Ser Leu Val Gln Ile Ala Glu Lys Leu
        195                 200                 205

<210> SEQ ID NO 40
<211> LENGTH: 212
<212> TYPE: PRT
<213> ORGANISM: Zea mays

<400> SEQUENCE: 40

Met Pro Phe Ala Ala Ser Arg Thr Ser Gln Gln Gln His Ser Arg Val
1               5                   10                  15

Ala Thr Asn Gly Arg Ala Val Ala Val Cys Ala Gly His Ala Gly Val
            20                  25                  30
```

```
Pro Asp Glu Val Ala Arg His His Glu His Ala Val Ala Ala Gly Gln
            35                  40                  45

Cys Cys Ala Ala Met Val Gln Ser Ile Ala Ala Pro Val Asp Ala Val
 50                  55                  60

Trp Ser Leu Val Arg Arg Phe Asp Gln Pro Gln Arg Tyr Lys Arg Phe
 65                  70                  75                  80

Ile Arg Ser Cys His Leu Val Asp Gly Asp Gly Ala Glu Val Gly Ser
                 85                  90                  95

Val Arg Glu Leu Leu Leu Val Ser Gly Leu Pro Ala Glu Ser Ser Arg
            100                 105                 110

Glu Arg Leu Glu Ile Arg Asp Asp Glu Arg Arg Val Ile Ser Phe Arg
        115                 120                 125

Val Leu Gly Gly Asp His Arg Leu Ala Asn Tyr Arg Ser Val Thr Thr
    130                 135                 140

Val His Glu Ala Ala Pro Ser Gln Asp Gly Arg Pro Leu Thr Met Val
145                 150                 155                 160

Val Glu Ser Tyr Val Val Asp Val Pro Pro Gly Asn Thr Val Glu Glu
                165                 170                 175

Thr Arg Ile Phe Val Asp Thr Ile Val Arg Cys Asn Leu Gln Ser Leu
            180                 185                 190

Glu Gly Thr Val Ile Arg Gln Leu Glu Ile Ala Ala Met Pro His Asp
        195                 200                 205

Asp Asn Gln Asn
    210

<210> SEQ ID NO 41
<211> LENGTH: 233
<212> TYPE: PRT
<213> ORGANISM: Zea mays

<400> SEQUENCE: 41

Met Arg Glu Arg Asn Ser Ser Ile Asp Gln Glu His Gln Arg Gly Ser
 1               5                  10                  15

Ser Ser Arg Ser Thr Met Pro Phe Ala Ala Ser Arg Thr Ser Gln Gln
            20                  25                  30

Gln His Ser Arg Val Ala Thr Asn Gly Arg Ala Val Ala Val Cys Ala
        35                  40                  45

Gly His Ala Gly Val Pro Asp Glu Val Ala Arg His His Glu His Ala
    50                  55                  60

Val Ala Ala Gly Gln Cys Cys Ala Ala Met Val Gln Ser Ile Ala Ala
 65                  70                  75                  80

Pro Val Asp Ala Val Trp Ser Leu Val Arg Arg Phe Asp Gln Pro Gln
                 85                  90                  95

Arg Tyr Lys Arg Phe Ile Arg Ser Cys His Leu Val Asp Gly Asp Gly
            100                 105                 110

Ala Glu Val Gly Ser Val Arg Glu Leu Leu Leu Val Ser Gly Leu Pro
        115                 120                 125

Ala Glu Ser Ser Arg Glu Arg Leu Glu Ile Arg Asp Asp Glu Arg Arg
    130                 135                 140

Val Ile Ser Phe Arg Val Leu Gly Gly Asp His Arg Leu Ala Asn Tyr
145                 150                 155                 160

Arg Ser Val Thr Thr Val His Glu Ala Ala Pro Ser Gln Asp Gly Arg
                165                 170                 175

Pro Leu Thr Met Val Val Glu Ser Tyr Val Val Asp Val Pro Pro Gly
            180                 185                 190
```

```
Asn Thr Val Glu Glu Thr Arg Ile Phe Val Asp Thr Ile Val Arg Cys
            195                 200                 205

Asn Leu Gln Ser Leu Glu Gly Thr Val Ile Arg Gln Leu Glu Ile Ala
        210                 215                 220

Ala Met Pro His Asp Asp Asn Gln Asn
225                 230

<210> SEQ ID NO 42
<211> LENGTH: 194
<212> TYPE: PRT
<213> ORGANISM: Physcomitrella patens

<400> SEQUENCE: 42

Met Met Gln Glu Lys Gln Gly Arg Pro Asp Phe Gln Phe Leu Leu Glu
1               5                   10                  15

Gly Gln Gln Asp Leu Ile Cys Arg Phe His Lys His Glu Leu Leu Pro
            20                  25                  30

His Gln Cys Gly Ser Ile Leu Leu Gln Ile Lys Ala Pro Val Gln
        35                  40                  45

Thr Val Trp Leu Ile Val Arg Arg Phe Asp Glu Pro Gln Val Tyr Lys
50                  55                  60

Arg Phe Ile Gln Arg Cys Asp Ile Val Glu Gly Asp Gly Val Val Gly
65                  70                  75                  80

Ser Ile Arg Glu Val Gln Leu Val Ser Ser Ile Pro Ala Thr Ser Ser
                85                  90                  95

Ile Glu Arg Leu Glu Ile Leu Asp Asp Glu His Ile Ile Ser Phe
            100                 105                 110

Arg Val Leu Gly Gly Gly His Arg Leu Gln Asn Tyr Trp Ser Val Thr
            115                 120                 125

Ser Leu His Arg His Glu Ile Gln Gly Gln Met Gly Thr Leu Val Leu
        130                 135                 140

Glu Ser Tyr Val Val Asp Ile Pro Asp Gly Asn Thr Arg Glu Glu Thr
145                 150                 155                 160

His Thr Phe Val Asp Thr Val Val Arg Cys Asn Leu Lys Ala Leu Ala
                165                 170                 175

Gln Val Ser Glu Gln Lys His Leu Leu Asn Ser Asn Glu Lys Pro Ala
            180                 185                 190

Ala Pro

<210> SEQ ID NO 43
<211> LENGTH: 191
<212> TYPE: PRT
<213> ORGANISM: Vitis vinifera

<400> SEQUENCE: 43

Met Lys Val Tyr Ser Pro Ser Gln Ile Leu Ala Glu Arg Gly Pro Arg
1               5                   10                  15

Ala Gln Ala Met Gly Asn Leu Tyr His Thr His Leu Leu Pro Asn
            20                  25                  30

Gln Cys Ser Ser Leu Val Val Gln Thr Thr Asp Ala Pro Leu Pro Gln
        35                  40                  45

Val Trp Ser Met Val Arg Arg Phe Asp Arg Pro Gln Ser Tyr Lys Arg
        50                  55                  60

Phe Val Arg Gly Cys Thr Leu Arg Gly Lys Gly Val Gly Ser
65                  70                  75                  80
```

```
Val Arg Glu Val Asn Ile Val Ser Gly Leu Pro Ala Glu Ile Ser Leu
            85                  90                  95

Glu Arg Leu Asp Lys Leu Asp Asp Leu His Val Met Arg Phe Thr
        100                 105                 110

Val Ile Gly Gly Asp His Arg Leu Ala Asn Tyr His Ser Thr Leu Thr
        115                 120                 125

Leu His Glu Asp Glu Asp Gly Val Arg Lys Thr Val Val Met Glu
    130                 135                 140

Ser Tyr Val Val Asp Val Pro Gly Gly Asn Ser Ala Gly Glu Thr Cys
145                 150                 155                 160

Tyr Phe Ala Asn Thr Ile Ile Gly Phe Asn Leu Lys Ala Leu Ala Ala
                165                 170                 175

Val Thr Glu Thr Met Ala Leu Lys Ala Asn Ile Pro Ser Gly Phe
        180                 185                 190

<210> SEQ ID NO 44
<211> LENGTH: 217
<212> TYPE: PRT
<213> ORGANISM: Physcomitrella patens

<400> SEQUENCE: 44

Met Gln Gln Val Lys Gly Arg Gln Asp Phe Gln Arg Leu Leu Glu Ala
1               5                   10                  15

Gln Gln Asp Leu Ile Cys Arg Tyr His Thr His Glu Leu Lys Ala His
            20                  25                  30

Gln Cys Gly Ser Ile Leu Leu Gln Gln Ile Lys Val Pro Leu Pro Ile
        35                  40                  45

Val Trp Ala Ile Val Arg Ser Phe Asp Lys Pro Gln Val Tyr Lys Arg
    50                  55                  60

Phe Ile Gln Thr Cys Lys Ile Thr Glu Gly Asp Gly Gly Val Gly Ser
65                  70                  75                  80

Ile Arg Glu Val His Leu Val Ser Ser Val Pro Ala Thr Cys Ser Ile
                85                  90                  95

Glu Arg Leu Glu Ile Leu Asp Asp Lys His Ile Ile Ser Phe Arg
        100                 105                 110

Val Leu Gly Gly Gly His Arg Leu Gln Asn Tyr Ser Ser Val Ser Ser
        115                 120                 125

Leu His Glu Leu Glu Val Glu Gly His Pro Cys Thr Leu Val Leu Glu
    130                 135                 140

Ser Tyr Met Val Asp Ile Pro Asp Gly Asn Thr Arg Glu Glu Thr His
145                 150                 155                 160

Met Phe Val Asp Thr Val Arg Cys Asn Leu Lys Ser Leu Ala Gln
                165                 170                 175

Ile Ser Glu Gln Gln Tyr Asn Lys Asp Cys Leu Gln Gln Lys Gln His
            180                 185                 190

Asp Gln Gln Gln Met Tyr Gln Gln Arg His Pro Pro Leu Pro Pro Ile
        195                 200                 205

Pro Ile Thr Asp Lys Asn Met Glu Arg
    210                 215

<210> SEQ ID NO 45
<211> LENGTH: 195
<212> TYPE: PRT
<213> ORGANISM: Physcomitrella patens

<400> SEQUENCE: 45
```

Met Arg Phe Asp Ile Gly His Asn Asp Val Arg Gly Phe Phe Thr Cys
1               5                   10                  15

Glu Glu Glu His Ala Tyr Ala Leu His Ser Gln Thr Val Glu Leu Asn
                20                  25                  30

Gln Cys Gly Ser Ile Leu Met Gln Gln Ile His Ala Pro Ile Glu Val
            35                  40                  45

Val Trp Ser Ile Val Arg Ser Phe Gly Ser Pro Gln Ile Tyr Lys Lys
        50                  55                  60

Phe Ile Gln Ala Cys Ile Leu Thr Val Gly Asp Gly Gly Val Gly Ser
65                  70                  75                  80

Ile Arg Glu Val Phe Leu Val Ser Gly Val Pro Ala Thr Ser Ser Ile
                85                  90                  95

Glu Arg Leu Glu Ile Leu Asp Asp Glu Lys His Val Phe Ser Phe Arg
                100                 105                 110

Val Leu Lys Gly Gly His Arg Leu Gln Asn Tyr Arg Ser Val Thr Thr
            115                 120                 125

Leu His Glu Gln Glu Val Asn Gly Arg Gln Thr Thr Thr Val Leu Glu
            130                 135                 140

Ser Tyr Val Val Asp Val Pro Asp Gly Asn Thr Arg Glu Glu Thr His
145                 150                 155                 160

Met Phe Ala Asp Thr Val Val Met Cys Asn Leu Lys Ser Leu Ala Gln
                165                 170                 175

Val Ala Glu Trp Arg Ala Met Gln Gly Ile Thr Gln Gln Leu Ser Thr
            180                 185                 190

Ser Ser Leu
        195

<210> SEQ ID NO 46
<211> LENGTH: 172
<212> TYPE: PRT
<213> ORGANISM: Vitis vinifera

<400> SEQUENCE: 46

Met Gly Asn Leu Tyr His Thr His His Leu Leu Pro Asn Gln Cys Ser
1               5                   10                  15

Ser Leu Val Val Gln Thr Thr Asp Ala Pro Leu Pro Gln Val Trp Ser
                20                  25                  30

Met Val Arg Arg Phe Asp Arg Pro Gln Ser Tyr Lys Arg Phe Val Arg
            35                  40                  45

Gly Cys Thr Leu Arg Arg Gly Lys Gly Val Gly Ser Val Arg Glu
        50                  55                  60

Val Asn Ile Val Ser Gly Leu Pro Ala Glu Ile Ser Leu Glu Arg Leu
65                  70                  75                  80

Asp Lys Leu Asp Asp Leu His Val Met Arg Phe Thr Val Ile Gly
                85                  90                  95

Gly Asp His Arg Leu Ala Asn Tyr His Ser Thr Leu Thr Leu His Glu
            100                 105                 110

Asp Glu Glu Asp Gly Val Arg Lys Thr Val Val Met Glu Ser Tyr Val
            115                 120                 125

Val Asp Val Pro Gly Gly Asn Ser Ala Gly Glu Thr Cys Tyr Phe Ala
        130                 135                 140

Asn Thr Ile Ile Gly Phe Asn Leu Lys Ala Leu Ala Ala Val Thr Glu
145                 150                 155                 160

Thr Met Ala Leu Lys Ala Asn Ile Pro Ser Gly Phe
                165                 170

<210> SEQ ID NO 47
<211> LENGTH: 196
<212> TYPE: PRT
<213> ORGANISM: Picea sitchensis

<400> SEQUENCE: 47

Met Glu Asp Leu Ser Ser Trp Arg Glu Gly Arg Ala Met Trp Leu Gly
1               5                   10                  15

Asn Pro Pro Ser Glu Ser Glu Leu Val Cys Arg His His Arg His Glu
            20                  25                  30

Leu Gln Gly Asn Gln Cys Ser Ser Phe Leu Val Lys His Ile Arg Ala
        35                  40                  45

Pro Val His Leu Val Trp Ser Ile Val Arg Thr Phe Asp Gln Pro Gln
    50                  55                  60

Lys Tyr Lys Pro Phe Val His Ser Cys Ser Val Arg Gly Gly Ile Thr
65                  70                  75                  80

Val Gly Ser Ile Arg Asn Val Asn Val Lys Ser Gly Leu Pro Ala Thr
                85                  90                  95

Ala Ser Glu Glu Arg Leu Glu Ile Leu Asp Asp Asn Glu His Val Phe
            100                 105                 110

Ser Ile Lys Ile Leu Gly Gly Asp His Arg Leu Gln Asn Tyr Ser Ser
        115                 120                 125

Ile Ile Thr Val His Pro Glu Ile Ile Asp Gly Arg Pro Gly Thr Leu
    130                 135                 140

Val Ile Glu Ser Tyr Val Val Asp Val Pro Glu Gly Asn Thr Arg Glu
145                 150                 155                 160

Glu Thr Arg Phe Phe Val Glu Ala Leu Val Lys Cys Asn Leu Lys Ser
                165                 170                 175

Leu Ala Asp Val Ser Glu Arg Leu Ala Ser Gln His His Thr Glu Leu
            180                 185                 190

Leu Glu Arg Thr
        195

<210> SEQ ID NO 48
<211> LENGTH: 185
<212> TYPE: PRT
<213> ORGANISM: Solanum tuberosum

<400> SEQUENCE: 48

Met Asn Ala Asn Gly Phe Cys Gly Val Glu Lys Glu Tyr Ile Arg Lys
1               5                   10                  15

His His Leu His Glu Pro Lys Glu Asn Gln Cys Ser Ser Phe Leu Val
            20                  25                  30

Lys His Ile Arg Ala Pro Val His Leu Val Trp Ser Leu Val Arg Arg
        35                  40                  45

Phe Asp Gln Pro Gln Lys Tyr Lys Pro Phe Ile Ser Arg Cys Ile Val
    50                  55                  60

Gln Gly Asp Leu Glu Ile Gly Ser Leu Arg Glu Val Asp Val Lys Ser
65                  70                  75                  80

Gly Leu Pro Ala Thr Thr Ser Thr Glu Arg Leu Glu Leu Leu Asp Asp
                85                  90                  95

Glu Glu His Ile Leu Ser Val Arg Ile Val Gly Gly Asp His Arg Leu
            100                 105                 110

Arg Asn Tyr Ser Ser Val Ile Ser Val His Pro Glu Val Ile Asp Gly
        115                 120                 125

```
Arg Pro Gly Thr Val Val Leu Glu Ser Phe Val Val Asp Val Pro Glu
            130                 135                 140

Gly Asn Thr Lys Asp Glu Thr Cys Tyr Phe Val Glu Ala Leu Ile Asn
145                 150                 155                 160

Cys Asn Leu Lys Ser Leu Ala Asp Ile Ser Glu Arg Val Ala Val Gln
                165                 170                 175

Asp Arg Thr Glu Pro Ile Asp Gln Val
            180                 185

<210> SEQ ID NO 49
<211> LENGTH: 190
<212> TYPE: PRT
<213> ORGANISM: Medicago truncatula

<400> SEQUENCE: 49

Met Asn Asn Gly Cys Glu Gln Gln Gln Tyr Ser Val Ile Glu Thr Gln
1               5                   10                  15

Tyr Ile Arg Arg His His Lys His Asp Leu Arg Asp Asn Gln Cys Ser
            20                  25                  30

Ser Ala Leu Val Lys His Ile Lys Ala Pro Val His Leu Val Trp Ser
        35                  40                  45

Leu Val Arg Arg Phe Asp Gln Pro Gln Lys Tyr Lys Pro Phe Ile Ser
50                  55                  60

Arg Cys Ile Met Gln Gly Asp Leu Ser Ile Gly Ser Val Arg Glu Val
65                  70                  75                  80

Asn Val Lys Ser Gly Leu Pro Ala Thr Thr Ser Thr Glu Arg Leu Glu
            85                  90                  95

Gln Leu Asp Asp Glu Glu His Ile Leu Gly Ile Arg Ile Val Gly Gly
            100                 105                 110

Asp His Arg Leu Arg Asn Tyr Ser Ser Ile Ile Thr Val His Pro Gly
        115                 120                 125

Val Ile Asp Gly Arg Pro Gly Thr Met Val Ile Glu Ser Phe Val Val
    130                 135                 140

Asp Val Pro Glu Gly Asn Thr Lys Asp Glu Thr Cys Tyr Phe Val Glu
145                 150                 155                 160

Ala Leu Ile Arg Tyr Asn Leu Ser Ser Leu Ala Asp Val Ser Glu Arg
                165                 170                 175

Met Ala Val Gln Gly Arg Thr Asp Pro Ile Asn Ile Asn Pro
            180                 185                 190

<210> SEQ ID NO 50
<211> LENGTH: 185
<212> TYPE: PRT
<213> ORGANISM: Vitis vinifera

<400> SEQUENCE: 50

Met Ser Gly Tyr Gly Cys Ile Lys Met Glu Asp Glu Tyr Ile Arg Arg
1               5                   10                  15

His His Arg His Glu Ile Arg Asp Asn Gln Cys Ser Ser Ser Leu Val
            20                  25                  30

Lys His Ile Lys Ala Pro Val His Leu Val Trp Ser Leu Val Arg Ser
        35                  40                  45

Phe Asp Gln Pro Gln Lys Tyr Lys Pro Phe Val Ser Arg Cys Ile Val
    50                  55                  60

Gln Gly Asp Leu Glu Ile Gly Ser Val Arg Glu Val Asn Val Lys Ser
65                  70                  75                  80
```

```
Gly Leu Pro Ala Thr Thr Ser Thr Glu Arg Leu Glu Leu Leu Asp Asp
                85                  90                  95

Glu Glu His Ile Phe Gly Met Arg Ile Val Gly Gly Asp His Arg Leu
            100                 105                 110

Lys Asn Tyr Ser Ser Ile Val Thr Val His Pro Glu Ile Ile Asp Gly
            115                 120                 125

Arg Pro Gly Thr Leu Val Ile Glu Ser Phe Val Val Asp Val Pro Asp
        130                 135                 140

Gly Asn Thr Lys Asp Glu Thr Cys Tyr Phe Val Glu Ala Leu Ile Lys
145                 150                 155                 160

Cys Asn Leu Lys Ser Leu Ala Asp Val Ser Glu Arg Leu Ala Ile Gln
                165                 170                 175

Asp Arg Thr Glu Pro Ile Asp Arg Met
            180                 185

<210> SEQ ID NO 51
<211> LENGTH: 185
<212> TYPE: PRT
<213> ORGANISM: Vitis vinifera

<400> SEQUENCE: 51

Met Asn Gly Asn Gly Leu Ser Ser Met Glu Ser Glu Tyr Ile Arg Arg
1               5                   10                  15

His His Arg His Glu Pro Ala Glu Asn Gln Cys Ser Ser Ala Leu Val
            20                  25                  30

Lys His Ile Lys Ala Pro Val Pro Leu Val Trp Ser Leu Val Arg Arg
        35                  40                  45

Phe Asp Gln Pro Gln Lys Tyr Lys Pro Phe Ile Ser Arg Cys Val Val
    50                  55                  60

Gln Gly Asn Leu Glu Ile Gly Ser Leu Arg Glu Val Asp Val Lys Ser
65                  70                  75                  80

Gly Leu Pro Ala Thr Thr Ser Thr Glu Arg Leu Glu Leu Leu Asp Asp
                85                  90                  95

Asp Glu His Ile Leu Ser Met Arg Ile Ile Gly Gly Asp His Arg Leu
            100                 105                 110

Arg Asn Tyr Ser Ser Ile Ile Ser Leu His Pro Glu Ile Ile Asp Gly
            115                 120                 125

Arg Pro Gly Thr Met Val Ile Glu Ser Tyr Val Val Asp Val Pro Glu
        130                 135                 140

Gly Asn Thr Lys Asp Glu Thr Cys Tyr Phe Val Glu Ala Leu Ile Lys
145                 150                 155                 160

Cys Asn Leu Lys Ser Leu Ala Asp Val Ser Glu Arg Leu Ala Val Gln
                165                 170                 175

Asp Arg Thr Glu Pro Ile Asp Arg Met
            180                 185

<210> SEQ ID NO 52
<211> LENGTH: 208
<212> TYPE: PRT
<213> ORGANISM: Oryza sativa

<400> SEQUENCE: 52

Met Glu Ala His Val Glu Arg Ala Leu Arg Glu Gly Leu Thr Glu Glu
1               5                   10                  15

Glu Arg Ala Ala Leu Glu Pro Ala Val Met Ala His His Thr Phe Pro
            20                  25                  30
```

```
Pro Ser Thr Thr Thr Ala Thr Ala Ala Thr Cys Thr Ser Leu
        35              40                  45

Val Thr Gln Arg Val Ala Ala Pro Val Arg Ala Val Trp Pro Ile Val
    50                  55                  60

Arg Ser Phe Gly Asn Pro Gln Arg Tyr Lys His Phe Val Arg Thr Cys
65              70                  75                  80

Ala Leu Ala Ala Gly Asn Gly Pro Ser Phe Gly Ser Val Arg Glu Val
                85                  90                  95

Thr Val Val Ser Gly Pro Ser Arg Leu Pro Pro Gly Thr Glu Arg Leu
                100                 105                 110

Glu Met Leu Asp Asp Arg His Ile Ile Ser Phe Arg Val Val Gly
            115                 120                 125

Gly Gln His Arg Leu Arg Asn Tyr Arg Ser Val Thr Ser Val Thr Glu
        130                 135                 140

Phe Gln Pro Pro Ala Ala Gly Pro Gly Pro Ala Pro Pro Tyr Cys Val
145                 150                 155                 160

Val Val Glu Ser Tyr Val Val Asp Val Pro Asp Gly Asn Thr Ala Glu
                165                 170                 175

Asp Thr Arg Met Phe Thr Asp Thr Val Val Lys Leu Asn Leu Gln Met
            180                 185                 190

Leu Ala Ala Val Ala Glu Asp Ser Ser Ala Ser Arg Arg Arg Asp
            195                 200                 205

<210> SEQ ID NO 53
<211> LENGTH: 186
<212> TYPE: PRT
<213> ORGANISM: Capsicum annuum

<400> SEQUENCE: 53

Met Met Asn Ala Asn Gly Phe Ser Gly Val Glu Lys Glu Tyr Ile Arg
1               5                   10                  15

Lys His His Leu His Gln Pro Lys Glu Asn Gln Cys Ser Ser Phe Leu
                20                  25                  30

Val Lys His Ile Arg Ala Pro Val His Leu Val Trp Ser Leu Val Arg
            35                  40                  45

Arg Phe Asp Gln Pro Gln Lys Tyr Lys Pro Phe Val Ser Arg Cys Ile
    50                  55                  60

Ala Gln Gly Asp Leu Glu Ile Gly Ser Leu Arg Glu Val Asp Val Lys
65                  70                  75                  80

Ser Gly Leu Pro Ala Thr Thr Ser Thr Glu Arg Leu Glu Leu Leu Asp
                85                  90                  95

Asp Glu Glu His Ile Leu Ser Phe Arg Ile Ile Gly Gly Asp His Arg
            100                 105                 110

Leu Arg Asn Tyr Ser Ser Ile Ile Ser Leu His Pro Glu Val Ile Asp
        115                 120                 125

Gly Arg Pro Gly Thr Leu Val Ile Glu Ser Phe Val Val Asp Val Pro
    130                 135                 140

Gln Gly Asn Thr Lys Asp Glu Thr Cys Tyr Phe Val Glu Ala Leu Ile
145                 150                 155                 160

Asn Cys Asn Leu Lys Ser Leu Ala Asp Val Ser Glu Arg Leu Ala Val
                165                 170                 175

Gln Asp Arg Thr Glu Pro Ile Asp Gln Val
            180                 185
```

```
<210> SEQ ID NO 54
<211> LENGTH: 186
<212> TYPE: PRT
<213> ORGANISM: Populus trichocarpa

<400> SEQUENCE: 54
```

Met Asn Gly Ser Asp Ala Tyr Ser Ala Thr Glu Ala Gln Tyr Val Arg
1               5                   10                  15

Arg His His Lys His Glu Pro Arg Glu Asn Gln Cys Thr Ser Ala Leu
            20                  25                  30

Val Lys His Ile Lys Ala Pro Ala His Leu Val Trp Ser Leu Val Arg
        35                  40                  45

Arg Phe Asp Gln Pro Gln Arg Tyr Lys Pro Phe Val Ser Arg Cys Val
    50                  55                  60

Met Asn Gly Glu Leu Gly Ile Gly Ser Val Arg Glu Val Asn Val Lys
65                  70                  75                  80

Ser Gly Leu Pro Ala Thr Thr Ser Thr Glu Arg Leu Glu Leu Leu Asp
                85                  90                  95

Asp Glu Glu His Ile Leu Gly Val Gln Ile Val Gly Gly Asp His Arg
            100                 105                 110

Leu Lys Asn Tyr Ser Ser Ile Met Thr Val His Pro Glu Phe Ile Asp
        115                 120                 125

Gly Arg Pro Gly Thr Leu Val Ile Glu Ser Phe Ile Val Asp Val Pro
    130                 135                 140

Asp Gly Asn Thr Lys Asp Glu Thr Cys Tyr Phe Val Glu Ala Leu Ile
145                 150                 155                 160

Arg Cys Asn Leu Lys Ser Leu Ala Asp Val Ser Glu Arg Met Ala Val
                165                 170                 175

Gln Asp Arg Val Glu Pro Val Asn Gln Phe
            180                 185

```
<210> SEQ ID NO 55
<211> LENGTH: 185
<212> TYPE: PRT
<213> ORGANISM: Capsicum annuum

<400> SEQUENCE: 55
```

Met Asn Ala Asn Gly Phe Ser Gly Val Glu Lys Glu Tyr Ile Arg Lys
1               5                   10                  15

His His Leu His Gln Pro Lys Glu Asn Gln Cys Ser Ser Phe Leu Val
            20                  25                  30

Lys His Ile Arg Ala Pro Val His Leu Val Trp Ser Leu Val Arg Arg
        35                  40                  45

Phe Asp Gln Pro Gln Lys Tyr Lys Pro Phe Val Ser Arg Cys Ile Ala
    50                  55                  60

Gln Gly Asp Leu Glu Ile Gly Ser Leu Arg Glu Val Asp Val Lys Ser
65                  70                  75                  80

Gly Leu Pro Ala Thr Thr Ser Thr Glu Arg Leu Glu Leu Leu Asp Asp
                85                  90                  95

Glu Glu His Ile Leu Ser Phe Arg Ile Ile Gly Gly Asp His Arg Leu
            100                 105                 110

Arg Asn Tyr Ser Ser Ile Ile Ser Leu His Pro Glu Val Ile Asp Gly
        115                 120                 125

Arg Pro Gly Thr Leu Val Ile Glu Ser Phe Val Val Asp Val Pro Gln
    130                 135                 140

Gly Asn Thr Lys Asp Glu Thr Cys Tyr Phe Val Glu Ala Leu Ile Asn

```
                 145                 150                 155                 160
Cys Asn Leu Lys Ser Leu Ala Asp Val Ser Glu Arg Leu Ala Val Gln
                165                 170                 175

Asp Arg Thr Glu Pro Ile Asp Gln Val
            180                 185

<210> SEQ ID NO 56
<211> LENGTH: 186
<212> TYPE: PRT
<213> ORGANISM: Populus trichocarpa

<400> SEQUENCE: 56

Met Asn Gly Ser Asp Ala Tyr Ser Ala Thr Glu Ala Gln Tyr Val Arg
1               5                   10                  15

Arg His His Lys His Glu Pro Arg Glu Asn Gln Cys Thr Ser Ala Leu
                20                  25                  30

Val Lys His Ile Lys Ala Pro Ala His Leu Val Trp Ser Leu Val Arg
            35                  40                  45

Arg Phe Asp Gln Pro Gln Arg Tyr Lys Pro Phe Val Ser Arg Cys Val
        50                  55                  60

Met Asn Gly Glu Leu Gly Ile Gly Ser Val Arg Glu Val Asn Val Lys
65                  70                  75                  80

Ser Gly Leu Pro Ala Thr Thr Ser Thr Glu Arg Leu Glu Leu Leu Asp
                85                  90                  95

Asp Glu Glu His Ile Leu Gly Val Gln Ile Val Gly Gly Asp His Arg
            100                 105                 110

Leu Lys Asn Tyr Ser Ser Ile Met Thr Val His Pro Glu Phe Ile Asp
        115                 120                 125

Gly Arg Pro Gly Thr Leu Val Ile Glu Ser Phe Ile Val Asp Val Pro
    130                 135                 140

Asp Gly Asn Thr Lys Asp Glu Thr Cys Tyr Phe Val Lys Ala Leu Ile
145                 150                 155                 160

Arg Cys Asn Leu Lys Ser Leu Ala Asp Val Ser Glu Arg Met Ala Val
                165                 170                 175

Gln Asp Arg Val Glu Pro Val Asn Gln Phe
            180                 185

<210> SEQ ID NO 57
<211> LENGTH: 188
<212> TYPE: PRT
<213> ORGANISM: Pisum sativum

<400> SEQUENCE: 57

Met Asn Asn Gly Gly Glu Gln Tyr Ser Ala Ile Glu Thr Gln Tyr Ile
1               5                   10                  15

Arg Arg Arg His Lys His Asp Leu Arg Asp Asn Gln Cys Ser Ser Ala
                20                  25                  30

Leu Val Lys His Ile Lys Ala Pro Val His Leu Val Trp Ser Leu Val
            35                  40                  45

Arg Arg Phe Asp Gln Pro Gln Lys Tyr Lys Pro Phe Val Ser Arg Cys
        50                  55                  60

Ile Met Gln Gly Asp Leu Gly Ile Gly Ser Val Arg Glu Val Asn Val
65                  70                  75                  80

Lys Ser Gly Leu Pro Ala Thr Thr Ser Thr Glu Arg Leu Glu Gln Leu
                85                  90                  95

Asp Asp Glu Glu His Ile Leu Gly Ile Arg Ile Val Gly Gly Asp His
```

```
                100                 105                 110
Arg Leu Arg Asn Tyr Ser Ser Val Ile Thr Val His Pro Glu Val Ile
            115                 120                 125

Asp Gly Arg Pro Gly Thr Met Val Ile Glu Ser Phe Val Asp Val
130                 135                 140

Pro Glu Gly Asn Thr Arg Asp Glu Thr Cys Tyr Phe Val Glu Ala Leu
145                 150                 155                 160

Ile Arg Gly Asn Leu Ser Ser Leu Ala Asp Val Ser Glu Arg Met Ala
                165                 170                 175

Val Gln Gly Arg Thr Asp Pro Ile Asn Val Asn Pro
            180                 185

<210> SEQ ID NO 58
<211> LENGTH: 177
<212> TYPE: PRT
<213> ORGANISM: Vitis vinifera

<400> SEQUENCE: 58

Met Glu Ala Gln Val Ile Cys Arg His His Ala His Glu Pro Arg Glu
1               5                   10                  15

Asn Gln Cys Ser Ser Val Leu Val Arg His Val Lys Ala Pro Ala Asn
            20                  25                  30

Leu Val Trp Ser Leu Val Arg Arg Phe Asp Gln Pro Gln Lys Tyr Lys
        35                  40                  45

Pro Phe Val Ser Arg Cys Val Val Gln Gly Asp Leu Arg Ile Gly Ser
    50                  55                  60

Val Arg Glu Val Asn Val Lys Thr Gly Leu Pro Ala Thr Thr Ser Thr
65                  70                  75                  80

Glu Arg Leu Glu Leu Phe Asp Asp Glu His Val Leu Gly Ile Lys
                85                  90                  95

Ile Leu Asp Gly Asp His Arg Leu Arg Asn Tyr Ser Ser Val Ile Thr
            100                 105                 110

Val His Pro Glu Ile Ile Asp Gly Arg Pro Gly Thr Leu Val Ile Glu
        115                 120                 125

Ser Phe Val Val Asp Val Pro Glu Gly Asn Thr Lys Asp Asp Thr Cys
    130                 135                 140

Tyr Phe Val Arg Ala Leu Ile Asn Cys Asn Leu Lys Cys Leu Ala Glu
145                 150                 155                 160

Val Ser Glu Arg Met Ala Met Leu Gly Arg Val Glu Pro Ala Asn Ala
                165                 170                 175

Val

<210> SEQ ID NO 59
<211> LENGTH: 178
<212> TYPE: PRT
<213> ORGANISM: Vitis vinifera

<400> SEQUENCE: 59

Met Met Glu Ala Gln Val Ile Cys Arg His His Ala His Glu Pro Arg
1               5                   10                  15

Glu Asn Gln Cys Ser Ser Val Leu Val Arg His Val Lys Ala Pro Ala
            20                  25                  30

Asn Leu Val Trp Ser Leu Val Arg Arg Phe Asp Gln Pro Gln Lys Tyr
        35                  40                  45

Lys Pro Phe Val Ser Arg Cys Val Val Gln Gly Asp Leu Arg Ile Gly
    50                  55                  60
```

```
Ser Val Arg Glu Val Asn Val Lys Thr Gly Leu Pro Ala Thr Thr Ser
 65                  70                  75                  80

Thr Glu Arg Leu Glu Leu Phe Asp Asp Glu His Val Leu Gly Ile
                 85                  90                  95

Lys Ile Leu Asp Gly Asp His Arg Leu Arg Asn Tyr Ser Ser Val Ile
                100                 105                 110

Thr Val His Pro Glu Ile Ile Asp Gly Arg Pro Gly Thr Leu Val Ile
                115                 120                 125

Glu Ser Phe Val Val Asp Val Pro Glu Gly Asn Thr Lys Asp Asp Thr
        130                 135                 140

Cys Tyr Phe Val Arg Ala Leu Ile Asn Cys Asn Leu Lys Cys Leu Ala
145                 150                 155                 160

Glu Val Ser Glu Arg Met Ala Met Leu Gly Arg Val Glu Pro Ala Asn
                165                 170                 175

Ala Val
```

```
<210> SEQ ID NO 60
<211> LENGTH: 193
<212> TYPE: PRT
<213> ORGANISM: Arachis hypogaea
<220> FEATURE:
<221> NAME/KEY: misc_feature
<222> LOCATION: (162)..(162)
<223> OTHER INFORMATION: Xaa can be any naturally occurring amino acid

<400> SEQUENCE: 60

Met Met Asn Gly Ser Cys Gly Gly Gly Gly Gly Glu Ala Tyr Gly
  1               5                  10                  15

Ala Ile Glu Ala Gln Tyr Ile Arg Arg His His Arg His Glu Pro Arg
                 20                  25                  30

Asp Asn Gln Cys Thr Ser Ala Leu Val Lys His Ile Arg Ala Pro Val
                 35                  40                  45

His Leu Val Trp Ser Leu Val Arg Arg Phe Asp Gln Pro Gln Lys Tyr
 50                  55                  60

Lys Pro Phe Val Ser Arg Cys Ile Met Gln Gly Asp Leu Gly Ile Gly
 65                  70                  75                  80

Ser Val Arg Glu Val Asn Val Lys Ser Gly Leu Pro Ala Thr Thr Ser
                 85                  90                  95

Thr Glu Arg Leu Glu Gln Leu Asp Asp Glu His Ile Leu Gly Ile
                100                 105                 110

Arg Ile Val Gly Gly Asp His Arg Leu Arg Asn Tyr Ser Ser Ile Ile
                115                 120                 125

Thr Val His Pro Glu Val Ile Glu Gly Arg Pro Gly Thr Met Val Ile
                130                 135                 140

Glu Ser Phe Val Val Asp Val Pro Asp Gly Asn Thr Lys Asp Glu Thr
145                 150                 155                 160

Cys Xaa Phe Val Glu Ala Leu Ile Arg Cys Asn Leu Ser Ser Leu Ala
                165                 170                 175

Asp Val Ser Glu Arg Met Ala Val Gln Gly Arg Thr Asp Pro Ile Asn
                180                 185                 190

Gln
```

```
<210> SEQ ID NO 61
<211> LENGTH: 217
<212> TYPE: PRT
<213> ORGANISM: Zea mays
```

```
<400> SEQUENCE: 61

Met Val Val Glu Met Asp Gly Gly Val Gly Val Ala Ala Gly Gly Gly
1               5                   10                  15

Gly Gly Ala Gln Thr Pro Ala Pro Pro Pro Arg Arg Trp Arg Leu
            20                  25                  30

Ala Asp Glu Arg Cys Asp Leu Arg Ala Met Glu Thr Asp Tyr Val Arg
            35                  40                  45

Arg Phe His Arg His Glu Pro Arg Asp His Gln Cys Ser Ser Ala Val
        50                  55                  60

Ala Lys His Ile Lys Ala Pro Val His Leu Val Trp Ser Leu Val Arg
65              70                  75                  80

Arg Phe Asp Gln Pro Gln Leu Phe Lys Pro Phe Val Ser Arg Cys Glu
                85                  90                  95

Met Lys Gly Asn Ile Glu Ile Gly Ser Val Arg Glu Val Asn Val Lys
            100                 105                 110

Ser Gly Leu Pro Ala Thr Arg Ser Thr Glu Arg Leu Glu Leu Leu Asp
        115                 120                 125

Asp Asp Glu Arg Ile Leu Ser Val Arg Phe Val Gly Gly Asp His Arg
130                 135                 140

Leu Gln Asn Tyr Ser Ser Ile Leu Thr Val His Pro Glu Val Ile Asp
145                 150                 155                 160

Gly Arg Pro Gly Thr Leu Val Ile Glu Ser Phe Val Val Asp Val Pro
                165                 170                 175

Asp Gly Asn Thr Lys Asp Glu Thr Cys Tyr Phe Val Glu Ala Leu Leu
            180                 185                 190

Lys Cys Asn Leu Arg Ser Leu Ala Glu Val Ser Glu Gly Gln Val Ile
        195                 200                 205

Met Asp Gln Thr Glu Pro Leu Asp Arg
    210                 215

<210> SEQ ID NO 62
<211> LENGTH: 217
<212> TYPE: PRT
<213> ORGANISM: Zea mays

<400> SEQUENCE: 62

Met Val Val Glu Met Asp Gly Gly Val Gly Val Ala Ala Ala Gly Gly
1               5                   10                  15

Gly Gly Ala Gln Thr Pro Ala Pro Pro Pro Arg Arg Trp Arg Leu
            20                  25                  30

Ala Asp Glu Arg Cys Asp Leu Arg Ala Met Glu Thr Asp Tyr Val Arg
            35                  40                  45

Arg Phe His Arg His Glu Pro Arg Asp His Gln Cys Ser Ser Ala Val
        50                  55                  60

Ala Lys His Ile Lys Ala Pro Val His Leu Val Trp Ser Leu Val Arg
65              70                  75                  80

Arg Phe Asp Gln Pro Gln Leu Phe Lys Pro Phe Val Ser Arg Cys Glu
                85                  90                  95

Met Lys Gly Asn Ile Glu Ile Gly Ser Val Arg Glu Val Asn Val Lys
            100                 105                 110

Ser Gly Leu Pro Ala Thr Arg Ser Thr Glu Arg Leu Glu Leu Leu Asp
        115                 120                 125

Asp Asp Glu Arg Ile Leu Ser Val Arg Phe Val Gly Gly Asp His Arg
130                 135                 140
```

-continued

Leu Gln Asn Tyr Ser Ser Ile Leu Thr Val His Pro Glu Val Ile Asp
145                 150                 155                 160

Gly Arg Pro Gly Thr Leu Val Ile Glu Ser Phe Val Asp Val Pro
                165                 170                 175

Asp Gly Asn Thr Lys Asp Glu Thr Cys Tyr Phe Val Glu Ala Leu Leu
            180                 185                 190

Lys Cys Asn Leu Arg Ser Leu Ala Glu Val Ser Glu Gly Gln Val Ile
        195                 200                 205

Met Asp Gln Thr Glu Pro Leu Asp Arg
    210                 215

<210> SEQ ID NO 63
<211> LENGTH: 206
<212> TYPE: PRT
<213> ORGANISM: Oryza sativa

<400> SEQUENCE: 63

Met Asn Gly Val Gly Gly Ala Gly Gly Ala Ala Ala Gly Lys Leu Pro
1               5                   10                  15

Met Val Ser His Arg Arg Val Gln Trp Arg Leu Ala Asp Glu Arg Cys
            20                  25                  30

Glu Leu Arg Glu Glu Met Glu Tyr Ile Arg Arg Phe His Arg His
        35                  40                  45

Glu Pro Ser Ser Asn Gln Cys Thr Ser Phe Ala Ala Lys His Ile Lys
    50                  55                  60

Ala Pro Leu His Thr Val Trp Ser Leu Val Arg Arg Phe Asp Gln Pro
65                  70                  75                  80

Gln Leu Phe Lys Pro Phe Val Arg Asn Cys Val Met Arg Glu Asn Ile
                85                  90                  95

Ile Ala Thr Gly Cys Ile Arg Glu Val Asn Val Gln Ser Gly Leu Pro
            100                 105                 110

Ala Thr Arg Ser Thr Glu Arg Leu Glu Leu Leu Asp Asp Asn Glu His
        115                 120                 125

Ile Leu Lys Val Asn Phe Ile Gly Gly Asp His Met Leu Lys Asn Tyr
    130                 135                 140

Ser Ser Ile Leu Thr Val His Ser Glu Val Ile Asp Gly Gln Leu Gly
145                 150                 155                 160

Thr Leu Val Val Glu Ser Phe Ile Val Asp Val Pro Glu Gly Asn Thr
                165                 170                 175

Lys Asp Asp Ile Ser Tyr Phe Ile Glu Asn Val Leu Arg Cys Asn Leu
            180                 185                 190

Arg Thr Leu Ala Asp Val Ser Glu Arg Leu Ala Asn Pro
        195                 200                 205

<210> SEQ ID NO 64
<211> LENGTH: 206
<212> TYPE: PRT
<213> ORGANISM: Oryza sativa

<400> SEQUENCE: 64

Met Asn Gly Ala Gly Gly Ala Gly Gly Ala Ala Ala Gly Lys Leu Pro
1               5                   10                  15

Met Val Ser His Arg Gln Val Gln Trp Arg Leu Ala Asp Glu Arg Cys
            20                  25                  30

Glu Leu Arg Glu Glu Met Glu Tyr Ile Arg Gln Phe His Arg His
        35                  40                  45

Glu Pro Ser Ser Asn Gln Cys Thr Ser Phe Val Ala Lys His Ile Lys
            50                  55                  60

Ala Pro Leu Gln Thr Val Trp Ser Leu Val Arg Arg Phe Asp Gln Pro
 65                  70                  75                  80

Gln Leu Phe Lys Pro Phe Val Arg Lys Cys Val Met Arg Glu Asn Ile
                 85                  90                  95

Ile Ala Thr Gly Cys Val Arg Glu Val Asn Val Gln Ser Gly Leu Pro
                100                 105                 110

Ala Thr Arg Ser Thr Glu Arg Leu Glu Leu Leu Asp Asp Asn Glu His
            115                 120                 125

Ile Leu Lys Val Lys Phe Ile Gly Gly Asp His Met Leu Lys Asn Tyr
        130                 135                 140

Ser Ser Ile Leu Thr Ile His Ser Glu Val Ile Asp Gly Gln Leu Gly
145                 150                 155                 160

Thr Leu Val Val Glu Ser Phe Val Val Asp Ile Pro Glu Gly Asn Thr
                165                 170                 175

Lys Asp Asp Ile Cys Tyr Phe Ile Glu Asn Ile Leu Arg Cys Asn Leu
                180                 185                 190

Met Thr Leu Ala Asp Val Ser Glu Glu Arg Leu Ala Asn Pro
            195                 200                 205

<210> SEQ ID NO 65
<211> LENGTH: 205
<212> TYPE: PRT
<213> ORGANISM: Oryza sativa

<400> SEQUENCE: 65

Met Val Glu Val Gly Gly Gly Ala Ala Glu Ala Ala Ala Gly Arg Arg
  1               5                  10                  15

Trp Arg Leu Ala Asp Glu Arg Cys Asp Leu Arg Ala Ala Glu Thr Glu
             20                  25                  30

Tyr Val Arg Arg Phe His Arg His Glu Pro Arg Asp His Gln Cys Ser
         35                  40                  45

Ser Ala Val Ala Lys His Ile Lys Ala Pro Val His Leu Val Trp Ser
 50                  55                  60

Leu Val Arg Arg Phe Asp Gln Pro Gln Leu Phe Lys Pro Phe Val Ser
 65                  70                  75                  80

Arg Cys Glu Met Lys Gly Asn Ile Glu Ile Gly Ser Val Arg Glu Val
                 85                  90                  95

Asn Val Lys Ser Gly Leu Pro Ala Thr Arg Ser Thr Glu Arg Leu Glu
                100                 105                 110

Leu Leu Asp Asp Asn Glu His Ile Leu Ser Val Arg Phe Val Gly Gly
            115                 120                 125

Asp His Arg Leu Lys Asn Tyr Ser Ser Ile Leu Thr Val His Pro Glu
        130                 135                 140

Val Ile Asp Gly Arg Pro Gly Thr Leu Val Ile Glu Ser Phe Val Val
145                 150                 155                 160

Asp Val Pro Glu Gly Asn Thr Lys Asp Glu Thr Cys Tyr Phe Val Glu
                165                 170                 175

Ala Leu Leu Lys Cys Asn Leu Lys Ser Leu Ala Glu Val Ser Glu Arg
                180                 185                 190

Leu Val Cys Gln Gly Pro Asn Arg Ala Pro Ser Thr Arg
            195                 200                 205

<210> SEQ ID NO 66
<211> LENGTH: 204
<212> TYPE: PRT
<213> ORGANISM: Oryza sativa

<400> SEQUENCE: 66

Met Val Glu Val Gly Gly Gly Ala Ala Glu Ala Ala Gly Arg Arg
1               5                   10                  15

Trp Arg Leu Ala Asp Glu Arg Cys Asp Leu Arg Ala Ala Glu Thr Glu
            20                  25                  30

Tyr Val Arg Arg Phe His Arg His Glu Pro Arg Asp His Gln Cys Ser
                35                  40                  45

Ser Ala Val Ala Lys His Ile Lys Ala Pro Val His Leu Val Trp Ser
        50                  55                  60

Leu Val Arg Arg Phe Asp Gln Pro Gln Leu Phe Lys Pro Phe Val Ser
65                  70                  75                  80

Arg Cys Glu Met Lys Gly Asn Ile Glu Ile Gly Ser Val Arg Glu Val
                85                  90                  95

Asn Val Lys Ser Gly Leu Pro Ala Thr Arg Ser Thr Glu Arg Leu Glu
            100                 105                 110

Leu Leu Asp Asp Asn Glu His Ile Leu Ser Val Arg Phe Val Gly Gly
                115                 120                 125

Asp His Arg Leu Lys Asn Tyr Ser Ser Ile Leu Thr Val His Pro Glu
        130                 135                 140

Val Ile Asp Gly Arg Pro Gly Thr Leu Val Ile Glu Ser Phe Val Val
145                 150                 155                 160

Asp Val Pro Glu Gly Asn Thr Lys Asp Glu Thr Cys Tyr Phe Val Glu
                165                 170                 175

Ala Leu Leu Lys Cys Asn Leu Lys Ser Leu Ala Glu Val Ser Glu Arg
            180                 185                 190

Leu Val Val Lys Asp Gln Thr Glu Pro Leu Asp Arg
            195                 200

<210> SEQ ID NO 67
<211> LENGTH: 199
<212> TYPE: PRT
<213> ORGANISM: Medicago truncatula

<400> SEQUENCE: 67

Met Glu Lys Met Asn Gly Thr Glu Asn Asn Gly Val Phe Asn Ser Thr
1               5                   10                  15

Glu Met Glu Tyr Ile Arg Arg His His Asn Gln Gln Pro Gly Glu Asn
            20                  25                  30

Gln Cys Ser Ser Ala Leu Val Lys His Ile Arg Ala Pro Val Pro Leu
            35                  40                  45

Val Trp Ser Leu Val Arg Arg Phe Asp Gln Pro Gln Lys Tyr Lys Pro
        50                  55                  60

Phe Val Ser Arg Cys Val Val Arg Gly Asn Leu Glu Ile Gly Ser Leu
65                  70                  75                  80

Arg Glu Val Asp Val Lys Ser Gly Leu Pro Ala Thr Thr Ser Thr Glu
                85                  90                  95

Arg Leu Glu Val Leu Asp Asp Asn Glu His Ile Leu Ser Ile Arg Ile
            100                 105                 110

Ile Gly Gly Asp His Arg Leu Arg Asn Tyr Ser Ser Ile Met Ser Leu
            115                 120                 125

His Pro Glu Ile Ile Asp Gly Arg Pro Gly Thr Leu Val Ile Glu Ser

```
                130                 135                 140
Phe Val Asp Val Pro Glu Gly Asn Thr Lys Asp Glu Thr Cys Tyr
145                 150                 155                 160

Phe Val Glu Ala Leu Ile Lys Cys Asn Leu Lys Ser Leu Ser Asp Val
                165                 170                 175

Ser Glu Gly His Ala Val Gln Asp Leu Thr Glu Pro Leu Asp Arg Val
                180                 185                 190

His Glu Leu Leu Ile Ser Gly
            195

<210> SEQ ID NO 68
<211> LENGTH: 199
<212> TYPE: PRT
<213> ORGANISM: Medicago truncatula

<400> SEQUENCE: 68

Met Glu Lys Met Asn Gly Thr Glu Asn Asn Gly Val Phe Asn Ser Thr
1               5                   10                  15

Glu Met Glu Tyr Ile Arg Arg His His Asn Gln Gln Pro Gly Glu Asn
                20                  25                  30

Gln Cys Ser Ser Ala Leu Val Lys His Ile Arg Ala Pro Val Pro Leu
            35                  40                  45

Val Trp Ser Leu Val Arg Arg Phe Asp Gln Pro Gln Lys Tyr Lys Pro
        50                  55                  60

Phe Val Ser Arg Cys Val Val Arg Gly Asn Leu Glu Ile Gly Ser Leu
65                  70                  75                  80

Arg Glu Val Asp Val Lys Ser Gly Leu Pro Ala Thr Thr Ser Thr Glu
                85                  90                  95

Arg Leu Glu Val Leu Asp Asp Asn Glu His Ile Leu Ser Ile Arg Ile
                100                 105                 110

Ile Gly Gly Asp His Arg Leu Arg Asn Tyr Ser Ser Ile Met Ser Leu
            115                 120                 125

His Pro Glu Ile Ile Asp Gly Arg Pro Gly Thr Leu Val Ile Glu Ser
        130                 135                 140

Phe Val Val Asp Val Pro Glu Gly Asn Thr Lys Asp Glu Thr Cys Tyr
145                 150                 155                 160

Phe Val Glu Ala Leu Ile Lys Cys Asn Leu Lys Ser Leu Ser Asp Val
                165                 170                 175

Ser Glu Gly His Ala Ala Gln Asp Leu Thr Glu Pro Leu Asp Arg Met
                180                 185                 190

His Glu Leu Leu Ile Ser Gly
            195

<210> SEQ ID NO 69
<211> LENGTH: 197
<212> TYPE: PRT
<213> ORGANISM: Zea mays

<400> SEQUENCE: 69

Met Val Gly Leu Val Gly Gly Ser Thr Ala Arg Ala Glu His Val Val
1               5                   10                  15

Ala Asn Ala Gly Gly Glu Ala Glu Tyr Val Arg Arg Met His Arg His
                20                  25                  30

Ala Pro Thr Glu His Gln Cys Thr Ser Thr Leu Val Lys His Ile Lys
            35                  40                  45

Ala Pro Val His Leu Val Trp Gln Leu Val Arg Arg Phe Asp Gln Pro
```

Gln Arg Tyr Lys Pro Phe Val Arg Asn Cys Val Val Arg Gly Asp Gln
65                  70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Leu His
            100                 105                 110

Ile Leu Gly Val Lys Phe Val Gly Gly Asp His Arg Leu Gln Asn Tyr
        115                 120                 125

Ser Ser Ile Ile Thr Val His Pro Glu Ser Ile Asp Gly Arg Pro Gly
    130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Asn Ser Leu Ala Glu Val Ser Glu Gln Leu Ala Val Glu Ser Pro Thr
            180                 185                 190

Ser Leu Ile Asp Gln
        195

<210> SEQ ID NO 70
<211> LENGTH: 197
<212> TYPE: PRT
<213> ORGANISM: Zea mays

<400> SEQUENCE: 70

Met Val Gly Leu Val Gly Gly Ser Thr Ala Arg Ala Glu His Val Val
1               5                   10                  15

Ala Asn Ala Gly Gly Glu Ala Glu Tyr Val Arg Arg Met His Arg His
            20                  25                  30

Ala Pro Thr Glu His Gln Cys Thr Ser Thr Leu Val Lys His Ile Lys
        35                  40                  45

Ala Pro Val His Leu Val Trp Glu Leu Val Arg Arg Phe Asp Gln Pro
    50                  55                  60

Gln Arg Tyr Lys Pro Phe Val Arg Asn Cys Val Val Arg Gly Asp Gln
65                  70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Leu His
            100                 105                 110

Ile Leu Gly Val Lys Phe Val Gly Gly Asp His Arg Leu Gln Asn Tyr
        115                 120                 125

Ser Ser Ile Ile Thr Val His Pro Glu Ser Ile Asp Gly Arg Pro Gly
    130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Asn Ser Leu Ala Glu Val Ser Glu Gln Leu Ala Val Glu Ser Pro Thr
            180                 185                 190

Ser Leu Ile Asp Gln
        195

<210> SEQ ID NO 71
<211> LENGTH: 212

<212> TYPE: PRT
<213> ORGANISM: Zea mays

<400> SEQUENCE: 71

Met Val Met Val Glu Met Asp Gly Gly Val Gly Gly Gly Gly Gly
1               5                   10                  15

Gly Gln Thr Pro Ala Pro Arg Arg Trp Arg Leu Ala Asp Glu Arg Cys
            20                  25                  30

Asp Leu Arg Ala Met Glu Thr Asp Tyr Val Arg Arg Phe His Arg His
            35                  40                  45

Glu Pro Arg Glu His Gln Cys Ser Ser Ala Val Ala Lys His Ile Lys
        50                  55                  60

Ala Pro Val His Leu Val Trp Ser Leu Val Arg Arg Phe Asp Gln Pro
65                  70                  75                  80

Gln Leu Phe Lys Pro Phe Val Ser Arg Cys Glu Met Lys Gly Asn Ile
                85                  90                  95

Glu Ile Gly Ser Val Arg Glu Val Asn Val Lys Ser Gly Leu Pro Ala
            100                 105                 110

Thr Arg Ser Thr Glu Arg Leu Glu Leu Leu Asp Asp Asn Glu His Ile
        115                 120                 125

Leu Ser Val Arg Phe Val Gly Gly Asp His Arg Leu Gln Asn Tyr Ser
130                 135                 140

Ser Ile Leu Thr Val His Pro Glu Val Ile Asp Gly Arg Pro Gly Thr
145                 150                 155                 160

Leu Val Ile Glu Ser Phe Val Val Asp Val Pro Asp Gly Asn Thr Lys
                165                 170                 175

Asp Glu Thr Cys Tyr Phe Val Glu Ala Leu Leu Lys Cys Asn Leu Lys
            180                 185                 190

Ser Leu Ala Glu Val Ser Glu Arg Gln Val Val Lys Asp Gln Thr Glu
        195                 200                 205

Pro Leu Asp Arg
    210

<210> SEQ ID NO 72
<211> LENGTH: 205
<212> TYPE: PRT
<213> ORGANISM: Oryza sativa

<400> SEQUENCE: 72

Met Asn Gly Ala Gly Gly Ala Gly Gly Ala Ala Gly Lys Leu Pro
1               5                   10                  15

Met Val Ser His Arg Arg Val Gln Cys Arg Leu Ala Asp Lys Arg Cys
            20                  25                  30

Glu Leu Arg Glu Glu Met Glu Tyr Ile Arg Gln Phe His Arg His
            35                  40                  45

Glu Pro Ser Ser Asn Gln Cys Thr Ser Phe Val Ala Lys His Ile Lys
        50                  55                  60

Ala Pro Leu Gln Thr Val Trp Ser Leu Val Arg Arg Phe Asp Gln Pro
65                  70                  75                  80

Gln Leu Phe Lys Pro Phe Val Arg Lys Cys Val Met Arg Glu Asn Ile
                85                  90                  95

Ile Val Thr Gly Cys Val Arg Glu Val Asn Val Gln Ser Gly Leu Pro
            100                 105                 110

Ala Thr Arg Ser Thr Glu Arg Leu Glu Leu Leu Asp Asp Asn Glu His
        115                 120                 125

```
Ile Leu Lys Val Lys Phe Ile Gly Gly Asp His Met Leu Lys Asn Tyr
    130                 135                 140

Ser Ser Ile Leu Thr Ile His Ser Glu Val Ile Asp Gly Gln Leu Gly
145                 150                 155                 160

Thr Leu Val Val Glu Ser Phe Val Val Asp Ile Pro Asp Gly Asn Thr
                165                 170                 175

Lys Asp Asp Ile Cys Tyr Phe Ile Glu Asn Val Leu Arg Cys Asn Leu
                180                 185                 190

Met Thr Leu Ala Asp Val Ser Glu Glu Arg Leu Ala Asn
        195                 200                 205

<210> SEQ ID NO 73
<211> LENGTH: 197
<212> TYPE: PRT
<213> ORGANISM: Zea mays

<400> SEQUENCE: 73

Met Val Gly Leu Val Gly Gly Ser Thr Ala Arg Ala Glu His Val Val
1               5                   10                  15

Ala Asn Ala Gly Gly Glu Thr Glu Tyr Val Arg Arg Leu His Arg His
                20                  25                  30

Ala Pro Ala Glu His Gln Cys Thr Ser Thr Leu Val Lys His Ile Lys
            35                  40                  45

Ala Pro Val His Leu Val Trp Glu Leu Val Arg Ser Phe Asp Gln Pro
        50                  55                  60

Gln Arg Tyr Lys Pro Phe Val Arg Asn Cys Val Val Arg Gly Asp Gln
65                  70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Asp Leu His
                100                 105                 110

Ile Leu Gly Val Lys Phe Val Gly Gly Asp His Arg Leu Gln Asn Tyr
            115                 120                 125

Ser Ser Ile Ile Thr Val His Pro Glu Ser Ile Asp Gly Arg Pro Gly
130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Lys Ser Leu Ala Glu Val Ser Glu Gln Leu Ala Val Glu Ser Pro Thr
                180                 185                 190

Ser Pro Ile Asp Gln
        195

<210> SEQ ID NO 74
<211> LENGTH: 206
<212> TYPE: PRT
<213> ORGANISM: Oryza sativa

<400> SEQUENCE: 74

Met Asn Gly Val Gly Gly Ala Gly Gly Ala Ala Gly Lys Leu Pro
1               5                   10                  15

Met Val Ser His Arg Arg Val Gln Trp Arg Leu Ala Asp Glu Arg Cys
                20                  25                  30

Glu Leu Arg Glu Glu Met Glu Tyr Ile Arg Arg Phe His Arg His
            35                  40                  45
```

```
Glu Pro Ser Ser Asn Gln Cys Thr Ser Phe Ala Ala Lys His Ile Lys
            50                  55                  60

Ala Pro Leu His Thr Val Trp Ser Leu Val Arg Arg Phe Asp Gln Pro
 65                  70                  75                  80

Gln Leu Phe Lys Pro Phe Val Arg Asn Cys Val Met Arg Glu Asn Ile
                 85                  90                  95

Ile Ala Thr Gly Cys Ile Arg Glu Val Asn Val Gln Ser Gly Leu Pro
            100                 105                 110

Ala Thr Arg Ser Thr Glu Arg Leu Glu Leu Leu Asp Asp Asn Glu His
            115                 120                 125

Ile Leu Lys Val Lys Phe Ile Gly Gly Asp His Met Leu Lys Asn Tyr
130                 135                 140

Ser Ser Ile Leu Thr Val His Ser Glu Val Ile Asp Gly Gln Leu Gly
145                 150                 155                 160

Thr Leu Val Val Glu Ser Phe Ile Val Asp Val Leu Glu Gly Asn Thr
                165                 170                 175

Lys Asp Asp Ile Ser Tyr Phe Ile Glu Asn Val Leu Arg Cys Asn Leu
            180                 185                 190

Arg Thr Leu Ala Asp Val Ser Glu Glu Arg Leu Ala Asn Pro
            195                 200                 205

<210> SEQ ID NO 75
<211> LENGTH: 209
<212> TYPE: PRT
<213> ORGANISM: Oryza sativa

<400> SEQUENCE: 75

Met Val Gly Leu Val Gly Gly Gly Gly Trp Arg Val Gly Asp Asp Ala
1               5                   10                  15

Ala Gly Gly Gly Gly Gly Ala Val Ala Ala Gly Ala Ala Ala Ala
            20                  25                  30

Ala Glu Ala Glu His Met Arg Arg Leu His Ser His Ala Pro Gly Glu
            35                  40                  45

His Gln Cys Ser Ser Ala Leu Val Lys His Ile Lys Ala Pro Val His
     50                  55                  60

Leu Val Trp Ser Leu Val Arg Ser Phe Asp Gln Pro Gln Arg Tyr Lys
65                  70                  75                  80

Pro Phe Val Ser Arg Cys Val Val Arg Gly Gly Asp Leu Glu Ile Gly
                85                  90                  95

Ser Val Arg Glu Val Asn Val Lys Thr Gly Leu Pro Ala Thr Thr Ser
            100                 105                 110

Thr Glu Arg Leu Glu Leu Leu Asp Asp Glu His Ile Leu Ser Val
            115                 120                 125

Lys Phe Val Gly Gly Asp His Arg Leu Arg Asn Tyr Ser Ser Ile Val
130                 135                 140

Thr Val His Pro Glu Ser Ile Asp Gly Arg Pro Gly Thr Leu Val Ile
145                 150                 155                 160

Glu Ser Phe Val Val Asp Val Pro Asp Gly Asn Thr Lys Asp Glu Thr
                165                 170                 175

Cys Tyr Phe Val Glu Ala Val Ile Lys Cys Asn Leu Thr Ser Leu Ala
            180                 185                 190

Glu Val Ser Glu Arg Leu Ala Val Gln Ser Pro Thr Ser Pro Leu Glu
            195                 200                 205

Gln
```

<210> SEQ ID NO 76
<211> LENGTH: 180
<212> TYPE: PRT
<213> ORGANISM: Oryza sativa

<400> SEQUENCE: 76

Met Val Glu Met Asp Ala Gly Gly Arg Pro Glu Pro Ser Pro Pro Ser
1               5                   10                  15

Gly Gln Cys Ser Ser Ala Val Thr Met Arg Ile Asn Ala Pro Val His
            20                  25                  30

Leu Val Trp Ser Ile Val Arg Arg Phe Glu Glu Pro His Ile Phe Gln
        35                  40                  45

Pro Phe Val Arg Gly Cys Thr Met Arg Gly Ser Thr Ser Leu Ala Val
    50                  55                  60

Gly Cys Val Arg Glu Val Asp Phe Lys Ser Gly Phe Pro Ala Lys Ser
65                  70                  75                  80

Ser Val Glu Arg Leu Glu Ile Leu Asp Asp Lys Glu His Val Phe Gly
                85                  90                  95

Val Arg Ile Ile Gly Gly Asp His Arg Leu Lys Asn Tyr Ser Ser Val
            100                 105                 110

Leu Thr Ala Lys Pro Glu Val Ile Asp Gly Glu Pro Ala Thr Leu Val
        115                 120                 125

Ser Glu Ser Phe Val Val Asp Val Pro Glu Gly Asn Thr Ala Asp Glu
    130                 135                 140

Thr Arg His Phe Val Glu Phe Leu Ile Arg Cys Asn Leu Arg Ser Leu
145                 150                 155                 160

Ala Met Val Ser Gln Arg Leu Leu Leu Ala Gln Gly Asp Leu Ala Glu
                165                 170                 175

Pro Pro Ala Gln
            180

<210> SEQ ID NO 77
<211> LENGTH: 176
<212> TYPE: PRT
<213> ORGANISM: Vitis vinifera

<400> SEQUENCE: 77

Met Asn Gly Asn Gly Leu Ser Ser Met Glu Ser Glu Tyr Ile Arg Arg
1               5                   10                  15

His His Arg His Glu Pro Ala Glu Asn Gln Cys Ser Ser Ala Leu Val
            20                  25                  30

Lys His Ile Lys Ala Pro Val Pro Leu Val Trp Ser Leu Val Arg Arg
        35                  40                  45

Phe Asp Gln Pro Gln Lys Tyr Lys Pro Phe Ile Ser Arg Cys Val Val
    50                  55                  60

Gln Gly Asn Leu Glu Ile Gly Ser Leu Arg Glu Val Asp Val Lys Ser
65                  70                  75                  80

Gly Leu Pro Ala Thr Thr Ser Thr Glu Arg Leu Glu Leu Leu Asp Asp
                85                  90                  95

Asp Glu His Ile Leu Ser Met Arg Ile Ile Gly Gly Asp His Arg Leu
            100                 105                 110

Arg Asn Tyr Ser Ser Ile Ile Ser Leu His Pro Glu Ile Ile Asp Gly
        115                 120                 125

Arg Pro Gly Thr Met Val Ile Glu Ser Tyr Val Val Asp Val Pro Glu
    130                 135                 140

```
Gly Asn Thr Lys Asp Glu Thr Cys Tyr Phe Ser Leu Ala Asp Val Ser
145                 150                 155                 160

Glu Arg Leu Ala Val Ala Gly Thr Val Thr Glu Pro Ile Asp Arg Met
                165                 170                 175

<210> SEQ ID NO 78
<211> LENGTH: 180
<212> TYPE: PRT
<213> ORGANISM: Oryza sativa

<400> SEQUENCE: 78

Met Val Glu Met Asp Ala Gly Gly Arg Pro Glu Pro Ser Pro Pro Ser
1               5                   10                  15

Gly Gln Cys Ser Ser Ala Val Thr Met Arg Ile Asn Ala Pro Val His
                20                  25                  30

Leu Val Trp Ser Ile Val Arg Arg Phe Glu Pro His Ile Phe Gln
            35                  40                  45

Pro Phe Val Arg Gly Cys Thr Met Arg Gly Ser Thr Ser Leu Ala Val
        50                  55                  60

Gly Cys Val Arg Glu Val Asp Phe Lys Ser Gly Phe Ser Ala Lys Ser
65                  70                  75                  80

Ser Val Glu Arg Leu Glu Ile Leu Asp Asp Lys Glu His Val Phe Gly
                85                  90                  95

Val Arg Ile Ile Gly Gly Asp His Arg Leu Lys Asn Tyr Ser Ser Val
                100                 105                 110

Leu Thr Ala Lys Pro Glu Val Ile Asp Gly Glu Pro Ala Thr Leu Val
            115                 120                 125

Ser Glu Ser Phe Val Ile Asp Val Pro Glu Gly Asn Thr Ala Asp Glu
        130                 135                 140

Thr Arg His Phe Val Glu Phe Leu Ile Arg Cys Asn Leu Arg Ser Leu
145                 150                 155                 160

Ala Met Val Ser Gln Arg Leu Leu Leu Ala Gln Gly Asp Leu Ala Glu
                165                 170                 175

Pro Pro Ala Gln
            180

<210> SEQ ID NO 79
<211> LENGTH: 215
<212> TYPE: PRT
<213> ORGANISM: Oryza sativa

<400> SEQUENCE: 79

Met Pro Cys Ile Pro Ala Ser Ser Pro Gly Ile Pro His Gln His Gln
1               5                   10                  15

His Gln His His Arg Ala Leu Ala Gly Val Gly Met Ala Val Gly Cys
                20                  25                  30

Ala Ala Glu Ala Ala Val Ala Ala Ala Gly Val Ala Gly Thr Arg Cys
            35                  40                  45

Gly Ala His Asp Gly Glu Val Pro Met Glu Val Ala Arg His His Glu
        50                  55                  60

His Ala Glu Pro Gly Ser Gly Arg Cys Cys Ser Ala Val Val Gln His
65                  70                  75                  80

Val Ala Ala Pro Ala Ala Ala Val Trp Ser Val Val Arg Arg Phe Asp
                85                  90                  95

Gln Pro Gln Ala Tyr Lys Arg Phe Val Arg Ser Cys Ala Leu Leu Ala
            100                 105                 110
```

```
Gly Asp Gly Gly Leu Gly Lys Val Arg Glu Arg Leu Glu Ile Leu Asp
            115                 120                 125

Asp Glu Ser His Val Leu Ser Phe Arg Val Val Gly Gly Glu His Arg
            130                 135                 140

Leu Lys Asn Tyr Leu Ser Val Thr Thr Val His Pro Ser Pro Ser Ala
145                 150                 155                 160

Pro Thr Ala Ala Thr Val Val Glu Ser Tyr Val Val Asp Val Pro
                165                 170                 175

Pro Gly Asn Thr Pro Glu Asp Thr Arg Val Phe Val Asp Thr Ile Val
            180                 185                 190

Lys Cys Asn Leu Gln Ser Leu Ala Lys Thr Ala Glu Lys Leu Ala Ala
            195                 200                 205

Gly Ala Arg Ala Ala Gly Ser
    210                 215

<210> SEQ ID NO 80
<211> LENGTH: 186
<212> TYPE: PRT
<213> ORGANISM: Rheum australe

<400> SEQUENCE: 80

Met Asn Gly Asp Gly Tyr Gly Gly Ser Glu Glu Phe Val Lys Arg
1               5                   10                  15

Tyr His Glu His Val Leu Ala Asp His Gln Cys Ser Ser Val Leu Val
            20                  25                  30

Glu His Ile Asn Ala Pro Leu His Leu Val Trp Ser Leu Val Arg Ser
            35                  40                  45

Phe Asp Gln Pro Gln Lys Tyr Lys Pro Phe Val Ser Arg Cys Val Val
50                  55                  60

Gln Gly Gly Asp Leu Glu Ile Gly Ser Val Arg Glu Val Asp Val Lys
65                  70                  75                  80

Ser Gly Leu Pro Ala Thr Thr Ser Met Glu Glu Leu Glu Leu Leu Asp
                85                  90                  95

Asp Lys Glu His Val Leu Arg Val Lys Phe Val Gly Gly Asp His Arg
            100                 105                 110

Leu Lys Asn Tyr Ser Ser Ile Val Ser Leu His Pro Glu Ile Ile Gly
            115                 120                 125

Gly Arg Ser Gly Thr Met Val Ile Glu Ser Phe Ile Val Asp Ile Ala
            130                 135                 140

Asp Gly Asn Thr Lys Glu Glu Thr Cys Tyr Phe Ile Glu Ser Leu Ile
145                 150                 155                 160

Asn Cys Asn Leu Lys Ser Leu Ser Cys Val Ser Glu Arg Leu Ala Val
                165                 170                 175

Glu Asp Ile Ala Glu Arg Ile Ala Gln Met
            180                 185

<210> SEQ ID NO 81
<211> LENGTH: 254
<212> TYPE: PRT
<213> ORGANISM: Oryza sativa

<400> SEQUENCE: 81

Met Val Gly Leu Val Gly Gly Gly Gly Trp Arg Val Gly Asp Asp Ala
1               5                   10                  15

Ala Gly Gly Gly Gly Gly Ala Val Ala Ala Gly Ala Ala Ala Ala
            20                  25                  30
```

Ala Glu Ala Glu His Met Arg Arg Leu His Ser Gln Gly Pro Arg Arg
            35                  40                  45

Ala Pro Val Gln Leu Arg Ala Arg Gln Ala His Gln Gly Ser Cys Ser
    50                  55                  60

Pro Pro Arg Ile Glu Cys Ala Asn Phe Ala Val Phe Leu Ala Ala Arg
65                  70                  75                  80

Asp Pro Lys Ile Val Trp Ser Leu Val Arg Ser Phe Asp Gln Pro Gln
                85                  90                  95

Arg Tyr Lys Pro Phe Val Ser Arg Cys Val Val Arg Gly Gly Asp Leu
            100                 105                 110

Glu Ile Gly Ser Val Arg Glu Val Asn Val Lys Thr Gly Leu Pro Ala
        115                 120                 125

Thr Thr Ser Thr Glu Arg Leu Glu Leu Leu Asp Asp Asp Glu His Ile
130                 135                 140

Leu Ser Val Lys Phe Val Gly Gly Asp His Arg Leu Arg Asn Tyr Ser
145                 150                 155                 160

Ser Ile Val Thr Val His Pro Glu Ser Ile Asp Gly Arg Pro Gly Thr
                165                 170                 175

Leu Val Ile Glu Ser Phe Val Val Asp Val Pro Asp Gly Asn Thr Lys
            180                 185                 190

Asp Glu Thr Cys Tyr Phe Val Glu Ala Val Ile Lys Cys Asn Leu Thr
        195                 200                 205

Ser Leu Ala Glu Met Val Arg Met Ile Ser Leu Val Leu Pro Phe Met
210                 215                 220

Leu Val Asp Arg Met Ser Gly Ile Thr Cys Glu Ser His Leu Glu Thr
225                 230                 235                 240

Thr Leu Val Arg Cys Gly Glu Tyr Ala Val Leu Ala His Val
                245                 250

<210> SEQ ID NO 82
<211> LENGTH: 186
<212> TYPE: PRT
<213> ORGANISM: Oryza sativa

<400> SEQUENCE: 82

Met Glu Pro His Met Glu Arg Ala Leu Arg Glu Ala Val Ala Ser Glu
1               5                   10                  15

Ala Glu Arg Arg Glu Leu Glu Gly Val Val Arg Ala His His Thr Gly
            20                  25                  30

Trp Asn Ala Pro Leu Ala Ala Val Trp Pro His Arg Ala Arg Val Arg
            35                  40                  45

Pro Thr Arg Ser Gly Thr Ser Thr Ser Ser Arg Ala Ser Ser Pro
    50                  55                  60

Pro Gly Asp Gly Ala Thr Val Gly Ser Val Arg Glu Val Ala Val Val
65                  70                  75                  80

Ser Gly Leu Pro Ala Ser Thr Ser Thr Glu Arg Leu Glu Ile Leu Asp
                85                  90                  95

Asp Asp Arg His Val Leu Ser Phe Arg Val Gly Gly Asp His Arg
            100                 105                 110

Leu Arg Asn Tyr Arg Ser Val Thr Ser Val Thr Glu Phe Ser Ser Pro
        115                 120                 125

Ser Ser Pro Pro Arg Pro Tyr Cys Val Val Val Glu Ser Tyr Val Val
130                 135                 140

Asp Val Pro Glu Gly Asn Thr Glu Glu Asp Thr Arg Met Phe Thr Asp
145                 150                 155                 160

```
Thr Val Val Lys Leu Asn Leu Gln Lys Leu Ala Ala Val Ala Thr Ser
            165                 170                 175

Ser Ser Pro Pro Ala Ala Gly Asn His His
            180                 185

<210> SEQ ID NO 83
<211> LENGTH: 150
<212> TYPE: PRT
<213> ORGANISM: Oryza sativa

<400> SEQUENCE: 83

Met Glu Val Val Trp Ser Ile Val Arg Arg Phe Glu Glu Pro His Ile
1               5                   10                  15

Phe Gln Pro Phe Val Arg Gly Cys Thr Met Arg Gly Ser Thr Ser Leu
            20                  25                  30

Ala Val Gly Cys Val Arg Glu Val Asp Phe Lys Ser Gly Phe Pro Ala
        35                  40                  45

Lys Ser Ser Val Glu Arg Leu Glu Ile Leu Asp Asp Lys Glu His Val
    50                  55                  60

Phe Gly Val Arg Ile Ile Gly Gly Asp His Arg Leu Lys Asn Tyr Ser
65                  70                  75                  80

Ser Val Leu Thr Ala Lys Pro Glu Val Ile Asp Gly Glu Pro Ala Thr
                85                  90                  95

Leu Val Ser Glu Ser Phe Val Val Asp Val Pro Glu Gly Asn Thr Ala
            100                 105                 110

Asp Glu Thr Arg His Phe Val Glu Phe Leu Ile Arg Cys Asn Leu Arg
        115                 120                 125

Ser Leu Ala Met Val Ser Gln Arg Leu Leu Leu Ala Gln Gly Asp Leu
    130                 135                 140

Ala Glu Pro Pro Gly Gln
145                 150

<210> SEQ ID NO 84
<211> LENGTH: 206
<212> TYPE: PRT
<213> ORGANISM: Oryza sativa

<400> SEQUENCE: 84

Met Pro Tyr Thr Ala Pro Arg Pro Ser Pro Gln His Ser Arg Ile
1               5                   10                  15

Gly Gly Cys Gly Gly Gly Val Leu Lys Ala Ala Gly Ala Ala Gly
            20                  25                  30

His Ala Ala Ser Cys Val Ala Val Pro Ala Glu Val Ala Arg His His
        35                  40                  45

Glu His Ala Ala Gly Val Gly Gln Cys Cys Ser Ala Val Val Gln Ala
    50                  55                  60

Ile Ala Ala Pro Val Asp Ala Val Trp Arg Thr Ser Thr Ser Ser Gly
65                  70                  75                  80

Ala Ala Ala Ser Trp Thr Ala Thr Ala Thr Ala Gly Pro Leu Pro Val
                85                  90                  95

Gly Ser Val Arg Glu Phe Arg Val Leu Ser Gly Leu Pro Gly Thr Ser
            100                 105                 110

Ser Arg Glu Arg Leu Glu Ile Leu Asp Asp Glu Arg Arg Val Leu Ser
        115                 120                 125

Phe Arg Val Val Gly Gly Glu His Arg Leu Ser Asn Tyr Arg Ser Val
    130                 135                 140
```

```
Thr Thr Val His Glu Thr Ala Ala Gly Ala Ala Ala Val Val Val
145                 150                 155                 160

Glu Ser Tyr Val Val Asp Val Pro His Gly Asn Thr Ala Asp Glu Thr
                165                 170                 175

Arg Met Phe Val Asp Thr Ile Val Arg Cys Asn Leu Gln Ser Leu Ala
            180                 185                 190

Arg Thr Ala Glu Gln Leu Ala Leu Ala Ala Pro Arg Ala Ala
        195                 200                 205

<210> SEQ ID NO 85
<211> LENGTH: 396
<212> TYPE: PRT
<213> ORGANISM: Vitis vinifera
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (168)..(168)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (277)..(277)
<223> OTHER INFORMATION: Xaa can be any naturally occurring amino acid

<400> SEQUENCE: 85

Met Pro Ile Ser Ser Leu Pro Phe Ser Leu Tyr Thr Val Thr Pro Asn
1               5                   10                  15

Pro Leu Lys Leu Ile Thr Thr His Ala His Ala Phe Thr Pro His Thr
            20                  25                  30

His Ile Phe Thr Leu Lys Phe Met Ser His Thr Tyr Cys Pro His Ile
        35                  40                  45

His His Ile Thr Ser Ile His Tyr Thr His Leu Leu Xaa Pro Ile Pro
    50                  55                  60

His Met Pro Leu Gln Pro Pro Leu Pro His Pro Ile Leu Pro Ser
65                  70                  75                  80

Met Pro Ala Phe Gln His Leu Tyr Ser Thr Asn Gln His Leu Gln Val
                85                  90                  95

Ala Leu Phe Ser Ala Arg Gly Pro Asn Ile Arg Asp Phe Asn Phe Gln
            100                 105                 110

Asp Ala Asp Leu Leu Lys Leu Asp Ile Leu Ala Pro Gly Ser Leu Ile
        115                 120                 125

Trp Ala Ala Trp Ser Pro Asn Gly Thr Asp Glu Ala Asn Tyr Val Gly
    130                 135                 140

Glu Gly Ser Pro Thr Val Ala Met Ile Ala Lys Arg Gly Pro Arg His
145                 150                 155                 160

Gly Lys Tyr Met Ala Phe Cys Xaa Met Tyr Arg Asp Asn Val Ala Pro
                165                 170                 175

Lys Gly Val Asn Xaa Ala Val Ala Thr Val Lys Thr Lys Arg Thr Ile
            180                 185                 190

Gln Leu Lys Thr Ser Leu Glu Ile Ala Cys His Tyr Ala Gly Ile Asn
        195                 200                 205

Ile Ser Gly Ile Asn Gly Glu Val Met Pro Gly Gln Trp Glu Tyr Gln
    210                 215                 220
```

```
Val Gly Pro Gly Gln Cys Ser Ser Leu Leu Ala Gln Arg Val His Val
225                 230                 235                 240

Pro Leu Ser Ala Val Gly Ser Val Val His Arg Phe Asp Lys Pro Gln
            245                 250                 255

Arg Tyr Gln His Val Ile Lys Ser Cys Arg Ile Glu Asp Gly Phe Glu
        260                 265                 270

Met Arg Met Gly Xaa Leu Arg Asp Val Asn Ile Ile Ser Gly Leu Pro
    275                 280                 285

Thr Ala Thr Asn Thr Gly Arg Leu Asp Met Gln Asp Asp Glu Arg His
290                 295                 300

Val Thr Arg Cys Pro His Gln Arg Gln Ser Glu Ser Lys Tyr Thr Glu
305                 310                 315                 320

Asn Asn Asn Ser Asp Ala Ser Ser Ile Lys Ser Pro Ile Asn Gly Pro
                325                 330                 335

Ser Glu His Leu Lys Thr Ala Ala Ser Pro Lys Thr Glu Ser Ile Ile
            340                 345                 350

Val Ile Asp Thr Ser Lys Phe Leu Asn Glu Asp Phe Glu Gly Lys
        355                 360                 365

Asp Glu Thr Ser Ser Ser Asn Gln Val Gln Ile Glu Asp Glu Asn Trp
    370                 375                 380

Glu Thr Arg Phe Pro Asn Thr Asp Ala Gly Ile Trp
385                 390                 395
```

<210> SEQ ID NO 86
<211> LENGTH: 443
<212> TYPE: PRT
<213> ORGANISM: Vitis vinifera
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (129)..(129)
<223> OTHER INFORMATION: Xaa can be any naturally occurring amino acid
<220> FEATURE:
<221> NAME/KEY: misc_feature
<222> LOCATION: (220)..(220)
<223> OTHER INFORMATION: Xaa can be any naturally occurring amino acid
<220> FEATURE:
<221> NAME/KEY: misc_feature
<222> LOCATION: (401)..(401)
<223> OTHER INFORMATION: Xaa can be any naturally occurring amino acid
<220> FEATURE:
<221> NAME/KEY: misc_feature
<222> LOCATION: (443)..(443)
<223> OTHER INFORMATION: Xaa can be any naturally occurring amino acid

<400> SEQUENCE: 86

```
Met Pro Ser Ala Xaa Lys Ser Ser Thr Val Pro Leu Ser Leu Xaa Gln
1               5                   10                  15

Phe Lys Leu Gly Leu Arg His Gly His Arg Val Ile Pro Trp Gly Asp
            20                  25                  30

Leu Asp Ser Leu Ala Met Leu Gln Arg Gln Leu Asp Val Asp Ile Leu
        35                  40                  45

Val Thr Gly His Thr His Arg Phe Thr Ala Tyr Lys His Glu Gly Gly
    50                  55                  60

Val Val Ile Asn Pro Gly Ser Ala Thr Gly Ala Phe Gly Ser Ile Thr
65                  70                  75                  80
```

Tyr Asp Val Asn Pro Ser Phe Val Leu Met Asp Ile Asp Gly Leu Arg
                85                  90                  95

Val Val Val Cys Val Tyr Glu Leu Ile Asp Glu Thr Ala Asn Ile Ile
            100                 105                 110

Lys Glu Leu His Ala Arg Lys Ile Ser Phe Gly Thr Lys Ser Met Ile
        115                 120                 125

Xaa Cys Leu Leu Leu Lys Arg Arg Ser Thr Pro Lys Phe Arg Arg Lys
    130                 135                 140

Lys Leu Phe Leu Phe Gln Cys Arg Val Gln Met Thr Leu Thr Leu Thr
145                 150                 155                 160

Asn Leu Ala Val Ser Gly Ile Ala Gln Thr Leu Gln Val Asp Gln Trp
                165                 170                 175

Thr Val Cys Ala Leu Ile Phe Met Thr Arg Arg Asp Ile His Leu Asp
            180                 185                 190

Lys Ala Arg Phe Leu Asp Phe Lys Asp Met Gly Lys Leu Leu Ala Asp
        195                 200                 205

Ala Ser Gly Leu Arg Lys Ala Leu Ser Gly Gly Xaa Val Thr Ala Gly
    210                 215                 220

Met Ala Ile Phe Asp Thr Met Arg His Ile Arg Pro Asp Val Pro Thr
225                 230                 235                 240

Val Cys Val Gly Leu Ala Ala Val Ala Met Ile Ala Lys Arg Gly Pro
                245                 250                 255

Arg His Gly Lys Tyr Met Ala Phe Cys Pro Met Tyr Arg Asp Asn Val
            260                 265                 270

Ala Pro Lys Gly Val Asn Val Ala Val Val Thr Val Lys Thr Lys Arg
        275                 280                 285

Thr Ile Gln Leu Lys Thr Ser Leu Glu Ile Ala Cys His Tyr Ala Gly
    290                 295                 300

Ile Asn Ile Ser Gly Ile Asn Gly Glu Val Met Pro Gly Gln Trp Glu
305                 310                 315                 320

Tyr Gln Val Gly Pro Gly Gln Cys Ser Ser Leu Leu Ala Gln Arg Val
                325                 330                 335

His Val Pro Leu Ser Ala Val Gly Ser Val Val His Arg Phe Asp Lys
            340                 345                 350

Pro Gln Arg Tyr Gln His Val Ile Lys Ser Cys Arg Ile Glu Asp Gly
        355                 360                 365

Phe Glu Met Arg Met Gly Arg Leu Arg Asp Val Asn Ile Ile Ser Gly
370                 375                 380

Leu Pro Thr Ala Thr Asn Thr Gly Arg Leu Asp Met Gln Asp Asp Glu
385                 390                 395                 400

Xaa His Val Thr Arg Cys Pro His Gln Arg Gln Ser Glu Ser Lys Tyr
                405                 410                 415

Thr Glu Asn Asn Asn Ser Asp Ala Ser Ser Val Lys Ser Pro Ile Asn
            420                 425                 430

Gly Pro Ser Glu His Leu Lys Thr Ala Ala Xaa
        435                 440

<210> SEQ ID NO 87
<211> LENGTH: 95
<212> TYPE: PRT
<213> ORGANISM: Oryza sativa

<400> SEQUENCE: 87

Glu Ile Gly Ser Val Arg Glu Val Asn Val Lys Thr Gly Leu Pro Ala

```
1               5                    10                   15
Thr Thr Ser Thr Glu Arg Leu Glu Leu Leu Asp Asp Asp Glu His Ile
                20                   25                   30

Leu Ser Val Lys Phe Val Gly Gly Asp His Arg Leu Arg Asn Tyr Ser
                35                   40                   45

Ser Ile Val Thr Val His Pro Glu Ser Ile Asp Gly Arg Pro Gly Thr
            50                  55                   60

Leu Val Ile Glu Ser Phe Val Asp Val Pro Asp Gly Asn Thr Lys
65                  70                   75                   80

Asp Glu Thr Cys Tyr Phe Val Glu Ala Val Ile Lys Cys Asn Leu
                85                   90                   95
```

<210> SEQ ID NO 88
<211> LENGTH: 191
<212> TYPE: PRT
<213> ORGANISM: Zea mays

<400> SEQUENCE: 88

```
Met Val Val Glu Met Asp Gly Gly Val Gly Val Ala Ala Ala Gly Gly
1               5                   10                  15

Gly Gly Ala Gln Thr Pro Ala Pro Pro Pro Arg Arg Trp Arg Leu
                20                  25                  30

Ala Asp Glu Arg Cys Asp Leu Arg Ala Met Glu Thr Asp Tyr Val Arg
                35                  40                  45

Arg Phe His Arg His Glu Pro Arg Asp His Gln Cys Ser Ser Ala Val
            50                  55                  60

Ala Lys His Ile Lys Ala Pro Val His Leu Val Trp Ser Leu Val Arg
65                  70                  75                  80

Arg Phe Asp Gln Pro Gln Leu Phe Lys Pro Phe Val Ser Arg Cys Glu
                85                  90                  95

Met Lys Gly Asn Ile Glu Ile Gly Ser Val Arg Glu Val Asn Val Lys
                100                 105                 110

Ser Gly Leu Pro Ala Thr Arg Ser Thr Glu Arg Leu Glu Leu Leu Asp
                115                 120                 125

Asp Asp Glu Arg Ile Leu Ser Val Arg Phe Val Gly Gly Asp His Arg
        130                 135                 140

Leu Gln Val Cys Ser Val Leu His Leu Ser Ile Phe Cys Ala Ala His
145                 150                 155                 160

Ala Arg Tyr Phe Ala His His Leu Lys Cys Val Leu Glu Phe Leu Cys
                165                 170                 175

Gln Met His Leu Asp Val Leu Pro Cys Asp Asp Ala Ile Leu Glu
                180                 185                 190
```

<210> SEQ ID NO 89
<211> LENGTH: 239
<212> TYPE: PRT
<213> ORGANISM: Oryza sativa

<400> SEQUENCE: 89

```
Met Asn Gly Cys Thr Gly Gly Ala Gly Gly Val Ala Ala Gly Arg Leu
1               5                   10                  15

Pro Ala Val Ser Leu Gln Gln Ala Gln Trp Lys Leu Val Asp Glu Arg
                20                  25                  30

Cys Glu Leu Arg Glu Glu Glu Met Glu Tyr Val Arg Arg Phe His Arg
                35                  40                  45

His Glu Ile Gly Ser Asn Gln Cys Asn Ser Phe Ile Ala Lys His Val
```

```
                50                  55                  60
Arg Ala Pro Leu Gln Asn Val Trp Ser Leu Val Arg Arg Phe Asp Gln
 65                  70                  75                  80

Pro Gln Ile Tyr Lys Pro Phe Val Arg Lys Cys Val Met Arg Gly Asn
                 85                  90                  95

Val Glu Thr Gly Ser Val Arg Glu Ile Val Gln Ser Gly Leu Pro
                100                 105                 110

Ala Thr Arg Ser Ile Glu Arg Leu Glu Phe Leu Asp Asp Asn Glu Tyr
                115                 120                 125

Ile Leu Arg Val Lys Phe Ile Gly Gly Asp His Met Leu Lys Lys Arg
130                 135                 140

Ile Pro Lys Lys Thr Tyr Ala Ile Ser Ser Arg Thr Cys Ser Asp Ser
145                 150                 155                 160

Ala Ile Ile Ala Val Gly Gln Ser Asn Cys Ala Pro Glu Ile Thr Ala
                165                 170                 175

Met Asn Gly Gly Val Ser Ile Gln Pro Trp Leu Ile Leu Leu Ala Phe
                180                 185                 190

Phe Ser Ser Pro Ser Asn Gln Thr Asn Pro Asp Ser Leu Arg Asp Met
                195                 200                 205

His Pro Gly Ser Trp Phe Gln Ile Leu Leu Val Leu Ala Met Phe Thr
                210                 215                 220

Cys Ser Lys Gly Ser Val Leu Pro Pro Ser Glu Lys Val Asn Val
225                 230                 235

<210> SEQ ID NO 90
<211> LENGTH: 36
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(10)
<223> OTHER INFORMATION: Xaa can be any naturally occurring amino acid
<220> FEATURE:
<221> NAME/KEY: misc_feature
<222> LOCATION: (13)..(16)
<223> OTHER INFORMATION: Xaa can be any naturally occurring amino acid
<220> FEATURE:
<221> NAME/KEY: misc_feature
<222> LOCATION: (18)..(22)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (27)..(31)
<223> OTHER INFORMATION: Xaa can be any naturally occurring amino acid
<220> FEATURE:
<221> NAME/KEY: misc_feature
<222> LOCATION: (33)..(35)
<223> OTHER INFORMATION: Xaa can be any naturally occurring amino acid

<400> SEQUENCE: 90

Cys Xaa Ser Xaa Xaa Xaa Xaa Xaa Xaa Xaa Ala Pro Xaa Xaa Xaa Xaa
 1               5                  10                  15

Trp Xaa Xaa Xaa Xaa Xaa Phe Xaa Xaa Pro Xaa Xaa Xaa Xaa Xaa Phe
                 20                  25                  30
```

Xaa Xaa Xaa Cys
       35

<210> SEQ ID NO 91
<211> LENGTH: 25
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(24)
<223> OTHER INFORMATION: Xaa can be any naturally occurring amino acid

<400> SEQUENCE: 91

Gly Xaa Xaa Arg Xaa Val Xaa Xaa Xaa Ser Xaa Xaa Pro Ala Xaa Xaa
1               5                   10                  15

Ser Xaa Glu Xaa Leu Xaa Xaa Xaa Asp
            20                  25

<210> SEQ ID NO 92
<211> LENGTH: 31
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:

```
<221> NAME/KEY: misc_feature
<222> LOCATION: (20)..(26)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid

<400> SEQUENCE: 92

Glu Ser Xaa Xaa Val Asp Xaa Pro Xaa Gly Xaa Xaa Xaa Xaa Xaa Thr
1               5                   10                  15

Xaa Xaa Phe Xaa Xaa Xaa Xaa Xaa Xaa Asn Leu Xaa Xaa Leu
            20                  25                  30

<210> SEQ ID NO 93
<211> LENGTH: 45
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (2)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(19)
<223> OTHER INFORMATION: Xaa can be any naturally occurring amino acid
<220> FEATURE:
<221> NAME/KEY: misc_feature
<222> LOCATION: (22)..(25)
<223> OTHER INFORMATION: Xaa can be any naturally occurring amino acid
<220> FEATURE:
<221> NAME/KEY: misc_feature
<222> LOCATION: (27)..(31)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (36)..(37)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (42)..(44)
<223> OTHER INFORMATION: Xaa can be any naturally occurring amino acid

<400> SEQUENCE: 93

His Xaa Xaa Xaa Xaa Xaa Xaa Xaa Xaa Cys Xaa Ser Xaa Xaa Xaa Xaa
1               5                   10                  15

Xaa Xaa Xaa Ala Pro Xaa Xaa Xaa Xaa Trp Xaa Xaa Xaa Xaa Xaa Phe
            20                  25                  30

Xaa Xaa Pro Xaa Xaa Tyr Lys Xaa Phe Xaa Xaa Xaa Cys
            35                  40                  45

<210> SEQ ID NO 94
<211> LENGTH: 48
<212> TYPE: PRT
<213> ORGANISM: Unknown
<220> FEATURE:
<223> OTHER INFORMATION: Consensus sequence
<220> FEATURE:
```

-continued

```
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(23)
<223> OTHER INFORMATION: Xaa can be any naturally occurring amino acid
<220> FEATURE:
<221> NAME/KEY: misc_feature
<222> LOCATION: (25)..(31)
<223> OTHER INFORMATION: Xaa can be any naturally occurring amino acid
<220> FEATURE:
<221> NAME/KEY: misc_feature
<222> LOCATION: (33)..(35)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid

<400> SEQUENCE: 94

Val Gly Arg Xaa Val Xaa Val Xaa Ser Gly Leu Pro Ala Xaa Xaa Ser
1               5                   10                  15

Xaa Glu Xaa Leu Xaa Xaa Xaa Asp Xaa Xaa Xaa Xaa Xaa Xaa Xaa Phe
            20                  25                  30

Xaa Xaa Xaa Gly Gly Xaa His Arg Leu Xaa Asn Tyr Xaa Ser Val Thr
        35                  40                  45

<210> SEQ ID NO 95
<211> LENGTH: 33
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
```

```
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(28)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 95

Val Xaa Glu Ser Tyr Xaa Val Asp Xaa Pro Xaa Gly Asn Xaa Xaa Xaa
1               5                   10                  15

Xaa Thr Xaa Xaa Phe Xaa Asp Xaa Xaa Xaa Xaa Xaa Asn Leu Gln Xaa
            20                  25                  30

Leu

<210> SEQ ID NO 96
<211> LENGTH: 50
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
```

```
<222> LOCATION: (34)..(34)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid

<400> SEQUENCE: 96

His Xaa His Xaa Xaa Xaa Xaa Xaa Gln Cys Xaa Ser Xaa Leu Val Lys
1               5                   10                  15

Xaa Ile Xaa Ala Pro Xaa His Xaa Val Trp Ser Xaa Val Arg Arg Phe
            20                  25                  30

Asp Xaa Pro Gln Lys Tyr Lys Pro Phe Xaa Ser Arg Cys Xaa Val Xaa
        35                  40                  45

Gly Xaa
    50

<210> SEQ ID NO 97
<211> LENGTH: 65
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (38)..(38)
```

-continued

```
<223> OTHER INFORMATION: Xaa can be any naturally occurring amino acid
<220> FEATURE:
<221> NAME/KEY: misc_feature
<222> LOCATION: (50)..(53)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (61)..(62)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid

<400> SEQUENCE: 97

Glu Xaa Gly Xaa Xaa Arg Glu Val Xaa Xaa Lys Ser Gly Leu Pro Ala
1               5                   10                  15

Thr Xaa Ser Thr Glu Xaa Leu Glu Xaa Leu Asp Asp Xaa Glu His Ile
            20                  25                  30

Leu Xaa Ile Xaa Ile Xaa Gly Gly Asp His Arg Leu Lys Asn Tyr Ser
        35                  40                  45

Ser Xaa Xaa Xaa Xaa His Xaa Glu Xaa Ile Xaa Gly Xaa Xaa Gly Thr
    50                  55                  60

Xaa
65

<210> SEQ ID NO 98
<211> LENGTH: 40
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
```

```
<221> NAME/KEY: misc_feature
<222> LOCATION: (35)..(37)
<223> OTHER INFORMATION: Xaa can be any naturally occurring amino acid

<400> SEQUENCE: 98

Xaa Xaa Glu Ser Phe Val Val Asp Val Pro Xaa Gly Asn Thr Lys Xaa
1               5                   10                  15

Xaa Thr Cys Xaa Phe Val Glu Xaa Leu Ile Xaa Cys Asn Leu Xaa Ser
            20                  25                  30

Leu Ala Xaa Xaa Xaa Glu Arg Leu
        35                  40

<210> SEQ ID NO 99
<211> LENGTH: 44
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(31)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(39)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid

<400> SEQUENCE: 99

Cys Xaa Ser Xaa Xaa Val Xaa Thr Ile Xaa Ala Pro Leu Xaa Leu Val
1               5                   10                  15

Trp Ser Ile Leu Arg Xaa Phe Asp Xaa Pro Xaa Xaa Xaa Xaa Xaa Phe
            20                  25                  30

Val Lys Xaa Cys Xaa Xaa Xaa Ser Gly Xaa Gly Gly
        35                  40
```

```
<210> SEQ ID NO 100
<211> LENGTH: 49
<212> TYPE: PRT
<213> ORGANISM: Unknown
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid

<400> SEQUENCE: 100

Gly Ser Val Arg Xaa Val Thr Xaa Val Ser Xaa Xaa Pro Ala Xaa Phe
1               5                   10                  15

Ser Xaa Glu Arg Leu Xaa Glu Leu Asp Asp Glu Ser His Val Met Xaa
            20                  25                  30

Xaa Ser Ile Ile Gly Gly Xaa His Arg Leu Val Asn Tyr Xaa Ser Lys
        35                  40                  45

Thr
```